US010570440B2

(12) United States Patent
White

(10) Patent No.: US 10,570,440 B2
(45) Date of Patent: Feb. 25, 2020

(54) METHOD FOR MODIFYING A TEMPLATE DOUBLE STRANDED POLYNUCLEOTIDE USING A MUA TRANSPOSASE

(71) Applicant: Oxford Nanopore Technologies Ltd., Oxford (GB)

(72) Inventor: James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 20 days.

(21) Appl. No.: 15/519,287

(22) PCT Filed: Feb. 18, 2015

(86) PCT No.: PCT/GB2015/050461
§ 371 (c)(1),
(2) Date: Apr. 14, 2017

(87) PCT Pub. No.: WO2016/059363
PCT Pub. Date: Apr. 21, 2016

(65) Prior Publication Data

US 2017/0240955 A1 Aug. 24, 2017

(30) Foreign Application Priority Data

Oct. 14, 2014 (GB) .................................. 1418159.8

(51) Int. Cl.
*C12Q 1/68* (2018.01)
*C07H 21/00* (2006.01)
*C12Q 1/6806* (2018.01)
*C12Q 1/6869* (2018.01)

(52) U.S. Cl.
CPC ......... *C12Q 1/6806* (2013.01); *C12Q 1/6869* (2013.01)

(58) Field of Classification Search
CPC ................................ C12Q 1/68; C12Q 1/6869
See application file for complete search history.

(56) References Cited

U.S. PATENT DOCUMENTS 5,215,899 A * 6/1993 Dattagupta ............ C12Q 1/682 435/320.1
5,424,413 A * 6/1995 Hogan ............... C12N 15/1068 435/6.1
5,561,043 A 10/1996 Cantor et al.
5,777,078 A 7/1998 Bayley et al.
5,795,782 A 8/1998 Church et al.
5,817,771 A 10/1998 Bayley et al.
5,866,328 A 2/1999 Bensimon et al.
5,866,336 A * 2/1999 Nazarenko ........... C12Q 1/6818 435/6.12
5,985,834 A 11/1999 Engel et al.
6,015,714 A 1/2000 Baldarelli et al.
6,087,099 A 7/2000 Gupte et al.
6,123,819 A 9/2000 Peeters
6,127,166 A 10/2000 Bayley et al.
6,251,610 B1 6/2001 Gupte et al.
6,362,002 B1 3/2002 Denison et al.
6,426,231 B1 7/2002 Bayley et al.
6,451,563 B1 9/2002 Wittig et al.
6,627,067 B1 9/2003 Branton et al.
6,787,308 B2 9/2004 Balasubramanian et al.
6,824,659 B2 11/2004 Bayley et al.
6,863,833 B1 3/2005 Bloom et al.
6,916,665 B2 7/2005 Bayley et al.
6,927,070 B1 8/2005 Bayley et al.
7,087,729 B1 8/2006 Prive
7,189,503 B2 3/2007 Akeson et al.
7,361,466 B2 4/2008 Korlach et al.
7,507,575 B2 3/2009 Bedingham et al.
8,105,846 B2 1/2012 Bayley et al.
8,143,030 B2 3/2012 Maxham et al.
8,343,746 B2 1/2013 Rank et al.
8,383,369 B2 2/2013 Maxham et al.
8,628,940 B2 1/2014 Sorenson et al.
8,652,779 B2 2/2014 Turner et al.
8,785,211 B2 7/2014 Bayley et al.
8,822,160 B2 9/2014 Bayley et al.
8,889,348 B2 11/2014 Ju
9,057,102 B2 6/2015 Turner et al.
9,116,118 B2 8/2015 Turner et al.
9,145,623 B2 9/2015 Kavanagh et al.
(Continued)

FOREIGN PATENT DOCUMENTS

CN 101495656 7/2009
CN 102245760 11/2011
(Continued)

OTHER PUBLICATIONS

Caruccio, N. Preparation of Next-Generation Sequencing Libraries Using Nextera Technology : Simultaneous DNA Fragmentation and Adaptor Tagging by in vitro Transposition. Ch. 17 in Methods in Molecular Biology 733 :24 Eds. Kwon and Riche.Springer Year (2011).*
Feng et al., Nanopore-based Fourth-generation DNA Sequencing Technology. Genomics Proteomics Bioinformatics 12 : 4-16 (Year: 2015).*
Kozarewa et al., Amplification-Free Library Preparation for paired-End Illumina Sequencing. Ch. 18 in Methods in Molecular Biology 733 :24 Eds. Kwon and Riche.Springer (Year: 2011).*
Singh et al., Target-Enrichment Through Amplification of Hairpin-Ligated Universal Targets for Next-Generation Sequencing Analysis. Ch. 19 in Methods in Molecular Biology 733 :24 Eds. Kwon and Riche.Springer (Year: 2011).*
(Continued)

*Primary Examiner* — Ethan C Whisenant
(74) *Attorney, Agent, or Firm* — Wolf, Greenfield & Sacks, P.C.

(57) ABSTRACT

The invention relates to a method for modifying a template double stranded polynucleotide, especially for characterisation using nanopore sequencing. The method produces from the template a plurality of modified double stranded polynucleotides. These modified polynucleotides can then be characterised.

19 Claims, 8 Drawing Sheets

Specification includes a Sequence Listing.

(56) References Cited

U.S. PATENT DOCUMENTS

| | | | |
|---|---|---|---|
| 9,150,918 | B2 | 10/2015 | Turner et al. |
| 9,542,527 | B2 | 1/2017 | Travers et al. |
| 9,546,400 | B2 | 1/2017 | Turner et al. |
| 9,551,023 | B2 | 1/2017 | Turner et al. |
| 9,556,480 | B2 | 1/2017 | Turner et al. |
| 9,678,056 | B2 | 6/2017 | Turner et al. |
| 9,738,929 | B2 | 8/2017 | Turner et al. |
| 9,957,560 | B2 | 5/2018 | Brown et al. |
| 10,221,450 | B2 | 3/2019 | Heron et al. |
| 2002/0028458 | A1 | 3/2002 | Lexow |
| 2002/0094526 | A1 | 7/2002 | Bayley et al. |
| 2002/0098530 | A1 | 7/2002 | Pfeifer et al. |
| 2002/0197618 | A1 | 12/2002 | Sampson |
| 2003/0044816 | A1 | 3/2003 | Denison et al. |
| 2003/0059778 | A1 | 3/2003 | Berlin et al. |
| 2003/0087232 | A1 | 5/2003 | Christians et al. |
| 2003/0099951 | A1 | 5/2003 | Akeson et al. |
| 2003/0108902 | A1 | 6/2003 | Abarzua |
| 2003/0118595 | A1 | 6/2003 | Niemeyer et al. |
| 2003/0165936 | A1 | 9/2003 | Rabbani et al. |
| 2003/0166137 | A1 | 9/2003 | Zuker et al. |
| 2003/0211502 | A1 | 11/2003 | Sauer et al. |
| 2003/0215881 | A1 | 11/2003 | Bayley et al. |
| 2004/0055901 | A1 | 3/2004 | Petersen et al. |
| 2004/0214177 | A1 | 10/2004 | Bension |
| 2004/0229315 | A1 | 11/2004 | Lee et al. |
| 2005/0053961 | A1 | 3/2005 | Akeson et al. |
| 2005/0142559 | A1 | 6/2005 | Makrigiorgos |
| 2005/0221316 | A1 | 10/2005 | Pedersen et al. |
| 2005/0227239 | A1 | 10/2005 | Joyce |
| 2005/0260655 | A1 | 11/2005 | Liu et al. |
| 2006/0063171 | A1 | 3/2006 | Akeson et al. |
| 2006/0086626 | A1 | 4/2006 | Joyce |
| 2006/0141516 | A1 | 6/2006 | Kobold et al. |
| 2006/0292611 | A1 | 12/2006 | Berka et al. |
| 2007/0015182 | A1 | 1/2007 | Abarzua |
| 2007/0031857 | A1* | 2/2007 | Makarov ................. C12P 19/34 435/6.18 |
| 2007/0122885 | A1 | 5/2007 | Reeves et al. |
| 2007/0224613 | A1 | 9/2007 | Strathmann |
| 2008/0166724 | A1 | 7/2008 | Gerber et al. |
| 2008/0206252 | A1 | 8/2008 | Pennica et al. |
| 2008/0311582 | A1 | 12/2008 | Bayley et al. |
| 2009/0256116 | A1 | 10/2009 | Shumaker-Parry et al. |
| 2009/0280538 | A1 | 11/2009 | Patel et al. |
| 2009/0298075 | A1 | 12/2009 | Travers et al. |
| 2010/0003560 | A1 | 1/2010 | Shibata |
| 2010/0035260 | A1 | 2/2010 | Olasagasti et al. |
| 2010/0075309 | A1 | 3/2010 | Maxham et al. |
| 2010/0092960 | A1 | 4/2010 | Fehr |
| 2010/0120098 | A1 | 5/2010 | Grunenwald et al. |
| 2010/0221212 | A1 | 9/2010 | Stagliano et al. |
| 2010/0276588 | A1 | 11/2010 | Syms |
| 2010/0331194 | A1 | 12/2010 | Turner et al. |
| 2011/0019186 | A1 | 1/2011 | Himmelhaus et al. |
| 2011/0136676 | A1 | 6/2011 | Greene |
| 2011/0214991 | A1 | 9/2011 | Kim et al. |
| 2011/0224106 | A1 | 9/2011 | Eshoo et al. |
| 2011/0281768 | A1 | 11/2011 | Travers et al. |
| 2011/0311965 | A1 | 12/2011 | Maglia et al. |
| 2012/0010085 | A1 | 1/2012 | Rava et al. |
| 2012/0058468 | A1 | 3/2012 | Mckeown |
| 2012/0100530 | A1 | 4/2012 | Moysey et al. |
| 2012/0107802 | A1 | 5/2012 | Stoddart et al. |
| 2013/0017978 | A1 | 1/2013 | Kavanagh et al. |
| 2013/0078624 | A1 | 3/2013 | Holmes et al. |
| 2013/0143802 | A1 | 6/2013 | Chilkoti |
| 2013/0195908 | A1 | 8/2013 | Leonetti et al. |
| 2013/0327644 | A1 | 12/2013 | Turner et al. |
| 2014/0134629 | A1 | 5/2014 | Turner et al. |
| 2014/0206842 | A1 | 7/2014 | Majeed et al. |
| 2014/0262784 | A1 | 9/2014 | Clarke et al. |
| 2014/0296089 | A1 | 10/2014 | Holmes et al. |
| 2014/0308661 | A1 | 10/2014 | Holmes et al. |
| 2015/0008126 | A1 | 1/2015 | Maglia et al. |
| 2015/0045257 | A1 | 2/2015 | Kavanagh et al. |
| 2015/0152492 | A1 | 6/2015 | Brown et al. |
| 2015/0167075 | A1 | 6/2015 | Turner et al. |
| 2015/0175663 | A1 | 6/2015 | Yokoi et al. |
| 2015/0197796 | A1 | 7/2015 | White et al. |
| 2015/0218629 | A1 | 8/2015 | Heron et al. |
| 2015/0265994 | A1 | 9/2015 | Hyde et al. |
| 2015/0285781 | A1 | 10/2015 | Heron et al. |
| 2015/0307934 | A1 | 10/2015 | Turner et al. |
| 2016/0010147 | A1 | 1/2016 | Heron et al. |
| 2016/0010148 | A1 | 1/2016 | Turner et al. |
| 2016/0011169 | A1 | 1/2016 | Turner et al. |
| 2016/0194677 | A1 | 7/2016 | Stoddart et al. |
| 2016/0257942 | A1 | 9/2016 | Bruce et al. |
| 2016/0281159 | A1 | 9/2016 | Brown et al. |
| 2016/0362739 | A1 | 12/2016 | Brown et al. |
| 2017/0002406 | A1 | 1/2017 | Bowen et al. |
| 2017/0067101 | A1 | 3/2017 | Clarke et al. |
| 2017/0321266 | A1 | 11/2017 | Mckeown |
| 2018/0291440 | A1 | 10/2018 | Mckeown |
| 2018/0291441 | A1 | 10/2018 | Brown et al. |

FOREIGN PATENT DOCUMENTS

| | | | |
|---|---|---|---|
| EP | 2682460 | A1 | 1/2014 |
| GB | 2130219 | | 5/1984 |
| GB | 2237390 | | 5/1991 |
| GB | 2453377 | | 4/2009 |
| JP | H11-137260 | | 5/1999 |
| JP | 2012-506704 | A | 3/2012 |
| WO | WO 1994/023065 | | 10/1994 |
| WO | WO 1999/005167 | | 2/1999 |
| WO | WO 2000/028312 | | 5/2000 |
| WO | WO 2001/040516 | | 6/2001 |
| WO | WO 2001/042782 | | 6/2001 |
| WO | WO 2001/059453 | | 8/2001 |
| WO | WO 2002/042496 | | 5/2002 |
| WO | WO 2003/095669 | | 11/2003 |
| WO | WO 2005/056750 | | 6/2005 |
| WO | WO 2005/118877 | | 12/2005 |
| WO | WO 2005/124888 | | 12/2005 |
| WO | WO 2006/020775 | | 2/2006 |
| WO | WO 2006/028508 | | 3/2006 |
| WO | WO 2006/100484 | | 9/2006 |
| WO | WO 2007/057668 | | 5/2007 |
| WO | WO 2007/075987 | | 7/2007 |
| WO | WO 2007/084103 | | 7/2007 |
| WO | WO 2007/146158 | | 12/2007 |
| WO | WO 2008/045575 | | 4/2008 |
| WO | WO 2008/083554 | | 7/2008 |
| WO | WO 2008/102120 | | 8/2008 |
| WO | WO 2008/102121 | | 8/2008 |
| WO | WO 2008/124107 | | 10/2008 |
| WO | WO 2009/035647 | | 3/2009 |
| WO | WO 2009/044170 | A1 | 4/2009 |
| WO | WO 2009/077734 | A2 | 6/2009 |
| WO | WO 2010/004265 | | 1/2010 |
| WO | WO 2010/004273 | | 1/2010 |
| WO | WO 2010/034018 | | 3/2010 |
| WO | WO 2010/048605 | A1 | 4/2010 |
| WO | WO 2010/051773 | | 5/2010 |
| WO | WO 2010/086602 | A1 | 8/2010 |
| WO | WO 2010/086603 | | 8/2010 |
| WO | WO 2010/086622 | | 8/2010 |
| WO | WO 2010/094040 | | 8/2010 |
| WO | WO 2010/109107 | A1 | 9/2010 |
| WO | WO 2010/109197 | | 9/2010 |
| WO | WO 2010/122293 | | 10/2010 |
| WO | WO 2011/067559 | | 6/2011 |
| WO | WO 2012/033524 | A2 | 3/2012 |
| WO | WO 2012/061832 | | 5/2012 |
| WO | WO 2012/083249 | A2 | 6/2012 |
| WO | WO 2012/098561 | A2 | 7/2012 |
| WO | WO 2012/098562 | A2 | 7/2012 |
| WO | WO 2012/103545 | A1 | 8/2012 |
| WO | WO 2012/107778 | A2 | 8/2012 |
| WO | WO 2012/164270 | A1 | 12/2012 |
| WO | WO 2013/014451 | A1 | 1/2013 |
| WO | WO 2013/041878 | A1 | 3/2013 |

(56) References Cited

FOREIGN PATENT DOCUMENTS

WO WO 2013/057495 A2 4/2013
WO WO 2013/098561 A1 7/2013
WO WO 2013/098562 A2 7/2013
WO WO 2013/131962 A1 9/2013
WO WO 2013/153359 A1 10/2013
WO WO 2013/185137 A1 12/2013
WO WO 2014/013259 A1 1/2014
WO WO 2014/013260 A1 1/2014
WO WO 2014/013262 A1 1/2014
WO WO 2014/108810 A2 7/2014
WO WO 2014/135838 A1 9/2014
WO WO 2014/153408 9/2014
WO WO 2015/022544 A1 2/2015
WO WO 2015/031909 A1 3/2015
WO WO 2015/055981 A2 4/2015
WO WO 2015/056028 A1 4/2015
WO WO 2015/110777 A1 7/2015
WO WO 2015/110813 A1 7/2015
WO WO 2015/189636 A1 12/2015
WO WO 2015/200609 A1 12/2015
WO WO 2016/003814 A1 1/2016

OTHER PUBLICATIONS

UniProt Database accession No. a4s1e1 sequence. May 15, 2007.
UniProt Database accession No. b4kac8 sequence. Sep. 23, 2008.
UniProt Database accession No. e1qus6 sequence. Nov. 30, 2010.
UniProt Database accession No. i3d0e7 sequence. Jul. 11, 2012.
UniProt Database accession No. k0im99 sequence. Nov. 28, 2012.
GenPept Accession No. XP 003728286. Jun. 7, 2012.
Press release: Oxford Nanopore introduces DNA 'strand sequencing' on the high-throughput GridION platform and presents MinION, a sequencer the size of a USB; memory stick, Feb. 2012.
[No Author Listed] HyperMu(TM)TransposonTools HyperMu(TM)<CHL-1>InsertionKit. Jan. 1, 2011. Retrieved from http://arb-ls.com/download/epi protocol/search/document/197p10611.pdf on Oct. 8, 2014.
[No Author Listed] Nucleic acid double helix, Wikipedia.com (accessed May 24, 2016).
[No Author Listed] PreCR Repair Mix—Product Information, FAQs, Protocols, Other Tools & Resources, Related Products etc. Jan. 1, 2010. Retrieved from https://www.neb.com/products/m0309-preer-repair-mix on Oct. 8, 2014.
[No Author Listed] Thermo Scientific Mutation Generation System Kit. Technical Manual. 2012.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Altschul et al., Basic local alignment search tool. J Mol Biol. Oct. 5, 1990 5;215(3):403-10.
Altschul, A protein alignment scoring system sensitive at all evolutionary distances. J Mol Evol. Mar. 1993;36(3):290-300.
Alzubutas et al., MuA Transposase enzyme enables fast and easy DNA library preparation for next generation sequencing. Thermo Fisher Scientific. Jan. 1, 2012. Retrieved from URL:http://www.gene-quantification.de/qper-ngs-2013/posters/P013-qPCR-NGS-2013.pdf on May 18, 2017.
Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Avrameas, Coupling of enzymes to proteins with glutaraldehyde. Use of the conjugates for the detection of antigens and antibodies. Immunochemistry. Jan. 1969;6(1):43-52.
Baker, De novo genome assembly: what every biologist should know. Nature methods. Apr. 2012;9(4):333-337.
Bayley et al., Stochastic sensors inspired by biology. Nature. Sep. 13, 2001;413(6852):226-30.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bowie et al., Deciphering the message in protein sequences: tolerance to amino acid substitutions. Science. Mar. 16, 1990;247(4948):1306-10.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.

(56) References Cited

OTHER PUBLICATIONS

Case 1:17-cv-01353-RGA Document 10. Oxford's opening brief in support of its motion to partially dismiss Pacbio's complaint for patent infringement. Nov. 16, 2017.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Coros et al., Effect of mutations in the Mu-host junction region on transpososome assembly. J Mol Biol. Jul. 6, 2001;310(2):299-309.
Cudic et al., Binding of Nucleotides in Water by Phenathridinium Bis(intercaland) Receptor Molecules. J. Chem. Soc., Chem. Commun., pp. 1073-1075 (1995).
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Deamer et al., Three decades of nanopore sequencing. Nat Biotechnol. May 6, 2016;34(5):518-24. doi: 10.1038/nbt.3423.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.
Eoff et al., Chemically modified DNA substrates implicate the importance of electrostatic interactions for DNA unwinding by Dda helicase. Biochemistry. Jan. 18, 2005;44(2):666-74.
Erie et al., A dumbbell-shaped, double-hairpin structure of DNA: a thermodynamic investigation. Biochemistry. Nov. 3, 1987;26(22):7150-9.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Flicek et al., Sense from sequence reads: methods for alignment and assembly. Nat Methods. Nov. 2009;6(11 Suppl):S6-S12. doi: 10.1038/nmeth.1376.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Fu et al., Selective bypass of a lagging strand roadblock by the eukaryotic replicative DNA helicase. Cell. Sep. 16, 2011;146(6):931-41. doi:10.1016/j.cell.2011.07.045.
Garcillán-Barcia et al., The diversity of conjugative relaxases and its application in plasmid classification. FEMS Microbiol Rev. May 2009 ;33(3):657-87.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Green et al., Quantitative evaluation of the lengths of homobifunctional protein cross-linking reagents used as molecular rulers. Protein Sci. Jul. 2001;10(7):1293-304.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Gui-Jiang et al., Advances in next-generation sequencing technologies. Progress in Modern Biomedicine. 2012;12(19):3789-3793.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.

(56) References Cited

OTHER PUBLICATIONS

Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Haque et al., Solid-State and Biological Nanopore for Real-Time Sensing of Single Chemical and Sequencing of DNA. Nano Today. Feb. 2013;8(1):56-74.
Heger, Nanopore Sequencing Makes Strides in 2010 as Technology Improves, Investment Grows. GenomeWeb. Jan. 11, 2011. Retrieved from https://www.genomeweb.com/sequencing/nanopore-sequencing-makes-strides-2010-technology-improves-investment-grows on Oct. 4, 2017.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Hobbs et al., SSB protein limits RecOR binding onto single-stranded DNA. J Biol Chem. Apr. 13, 2007;282(15):11058-67. Epub Feb. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.
Ivanov et al., DNA tunneling detector embedded in a nanopore. Nano Lett. Jan. 12, 2011;11(1):279-85. doi: 10.1021/n1103873a. Epub Dec. 6, 2010.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kalisch et al., Covalently linked sequencing primer linkers (splinkers) for sequence analysis of restriction fragments. Gene. 1986;44(2-3):263-70.
Kanan et al., Reaction discovery enabled by DNA-templated synthesis and in vitro selection. Nature. Sep. 30, 2004;431(7008):545-9.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222. Epub Jun. 29, 2011.
Khulbe et al., DNA translocation through a-hemolysin nanopores with potential application to macromolecular data storage. Journal Applied Physics, vol. 97(104317):1-7 (2005).
Kocalka et al., Rapid and efficient DNA strand cross-linking by click chemistry. Chembiochem. May 23, 2008;9(8):1280-5. doi:10.1002/cbic.200800006.
Kolb et al., Click Chemistry: Diverse Chemical Function from a Few Good Reactions. Angew Chem Int Ed Engl. Jun. 1, 2001;40(11):2004-2021.
Kovall et al., Toroidal structure of lambda-exonuclease. Science. Sep. 19, 1997;277(5333):1824-7.
Kozlov et al., Regulation of single-stranded DNA binding by the C termini of *Escherichia coli* single-stranded DNA-binding (SSB) protein. J Biol Chem. May 28, 2010;285(22):17246-52. doi: 10.1074/jbc.M110.118273. Epub Apr. 1, 2010.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Langecker et al., Synthetic lipid membrane channels formed by designed DNA nanostructures. Science. Nov. 16, 2012;338(6109):932-6. doi: 10.1126/science.1225624.
Lazar et al., Transforming growth factor alpha: mutation of aspartic acid 47 and leucine 48 results in different biological activities. Mol Cell Biol. Mar. 1988;8(3):1247-52.
Lee et al., Importance of the conserved CA dinucleotide at Mu termini. J Mol Biol. Nov. 30, 2001;314(3):433-44.
Li et al., DNA molecules and configurations in a solid-state nanopore microscope. Nat Mater. Sep. 2003;2(9):611-5. Epub Aug. 24, 2003.
Li et al., DNA Sequencing Method Based on Electro-Mechanical Effects Between DNA and Nano-Structures. Advances in Mechanics. Nov. 25, 2011;41(6):722-729.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008;133(5):801-12. doi: 10.1016/j.cell.2008.04.029.
Lodish et al., Molecular Cell Biology. Fourth Edition. New York: W.H. Freeman; 2000. Section 4.1, Structure of Nucleic Acids, pp. 101-110.
Lohman et al., Mechanisms of helicase-catalyzed DNA unwinding. Annu Rev Biochem. 1996;65:169-214.
Lohman et al., Non-hexameric DNA helicases and translocases:mechanisms and regulation. Nat Rev Mol Cell Biol. May 2008;9(5):391-401. doi:10.1038/nrm2394.
Lovett et al., Identification and purification of a single-stranded-DNA-specific exonuclease encoded by the recJ gene of *Escherichia coli*. Proc Natl Acad Sci U S A. Apr. 1989;86(8):2627-31.
Lovrinovic et al., Rapid synthesis of DNA-cysteine conjugates for expressed protein ligation. Biochem Biophys Res Commun. Sep. 2005 30;335(3):943-8.
Luo et al., Influence of polymer-pore interactions on translocation. Phys Rev Lett. Oct. 5, 2007;99(14):148102. Epub Oct. 1, 2007.
Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
Ma et al., Bright functional rotaxanes. Chem Soc Rev. Jan. 2010;39(1):70-80. doi: 10.1039/b901710k. Epub Jul. 21, 2009.
Maglia et al., Analysis of single nucleic acid molecules with protein nanopores. Methods Enzymol. 2010;475:591-623. doi: 10.1016/S0076-6879(10)75022-9.

(56) References Cited

OTHER PUBLICATIONS

Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub 2008 Dec 5.
Martin et al., Nanoscale protein pores modified with PAMAM dendrimers. J Am Chem Soc. Aug. 8, 2007;129(31):9640-9. Epub Jul. 18, 2007.
Martînez et al., The mRNA cap structure stimulates rate of poly(A) removal and amplifies processivity of degradation. J Biol Chem. Jul. 27, 2001;276(30):27923-9. Epub May 18, 2001.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometrescale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Mol et al., Structure and function of the multifunctional DNA-repair enzyme exonuclease III. Nature. Mar. 23, 1995;374(6520):381-6.
Montal et al., Formation of bimolecular membranes from lipid monolayers and a study of their electrical properties. Proc Natl Acad Sci U S A. Dec. 1972;69(12):3561-6.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
O'Shea et al., X-ray structure of the GCN4 leucine zipper, a two-stranded, parallel coiled coil. Science. Oct. 25, 1991;254(5031):539-44.
Paner et al., Studies of DNA dumbbells. III. Theoretical analysis of optical melting curves of dumbbells with a 16 base-pair duplex stem and Tn end loops (n = 2, 3, 4, 6, 8, 10, 14). Biopolymers. Jul. 1992;32(7):881-92.
Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Pfeiffer et al., Bivalent cholesterol-based coupling of oligonucletides to lipid membrane assemblies. J Am Chem Soc. Aug. 25, 2004;126(33):10224-5.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Pinero-Fernandez et al., Indole transport across *Escherichia coli* membranes. J Bacteriol. Apr. 2011;193(8):1793-8. doi:10.1128/JB.01477-10. Epub Feb. 4, 2011.
Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.
Remaut et al., Protein-protein interaction through beta-strand addition. Trends Biochem Sci. Aug. 2006;31(8):436-44. Epub Jul. 7, 2006.
Richards et al., Structure of the DNA repair helicase he1308 reveals DNA binding and autoinhibitory domains. J Biol Chem. Feb. 22, 2008;283(8):5118-26. Epub Dec. 4, 2007.
Saariaho et al., Characteristics of MuA transposase-catalyzed processing of model transposon end DNA hairpin substrates. Nucleic Acids Res. Jun. 6, 2006;34(10):3139-49. Print 2006.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.
Sauer-Budge et al., Unzipping kinetics of double-stranded DNA in a nanopore. Phys Rev Lett. Jun. 13, 2003;90(23):238101. Epub Jun. 9, 2003.
Savilahti et al., The phage Mu transpososome core: DNA requirements for assembly and function. EMBO J. Oct. 2, 1995;14(19):4893-903.
Schneider et al., DNA sequencing with nanopores. Nat Biotechnol. Apr. 10, 2012;30(4):326-8. doi: 10.1038/nbt.2181.
Seeman, Nucleic acid junctions and lattices. J Theor Biol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and base-stacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shin et al., Kinetics of a reversible covalent-bond-forming reaction observed at the single-molecule level. Angew Chem Int Ed Engl. Oct. 4, 2002;41(19):3707-9; 3523.
Smeets et al., Salt dependence of ion transport and DNA translocation through solid-state nanopores. Nano Lett. Jan. 2006;6(1):89-95.
Song et al., Structure of staphylococcal alpha-hemolysin, a heptameric transmembrane pore. Science. Dec. 13, 1996;274(5294):1859-66.
Soni et al., Synchronous optical and electrical detection of biomolecules traversing through solid-state nanopores. Rev Sci Instrum. Jan. 2010;81(1):014301. doi: 10.1063/1.3277116.

(56) References Cited

OTHER PUBLICATIONS

Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Suhasini et al., Mechanistic and biological aspects of helicase action on damaged DNA. Cell Cycle. Jun. 15, 2010;9(12):2317-29. Epub Jun. 15, 2010.
Sutherland et al., An analysis of mismatched duplex DNA unzipping through a bacterial nanopore. Biochem Cell Biol. Jun. 2004;82(3):407-12.
Tackett et al., Unwinding of unnatural substrates by a DNA helicase. Biochemistry. Jan. 16, 2001;40(2):543-8.
Tadey et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 25, 1978;253(2):424-9.
Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
United States District Court for the District of Delaware Order. *Pacific Biosciences of California, Inc.* v. *Oxford Nanopore Technolgoies, Inc.* Civil Action No. 17-275-RGA. Nov. 9, 2017.
Van De Goor, Nanopore Detection: Threading DNA Through a Tiny Hole. PharmaGenomics, vol. 4 (3):28-30 (2004).
Van Heel et al., Single-particle electron cryo-microscopy:towards atomic resolution. Q Rev Biophys. Nov. 2000;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Vinson, Proteins in motion. Introduction. Science. Apr. 10, 2009;324(5924):197. doi: 10.1126/science.324.5924.197.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., Bioconjugation by copper(I)-catalyzed azide-alkyne [3 + 2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007, 2;129(45):14034-41. Epub Oct. 19, 2007.
Wong et al., Polymer capture by electro-osmotic flow of oppositely charged nanopores. J Chem Phys. Apr. 28, 2007;126(16):164903.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Wu et al., Protein nanopores with covalently attached molecular adapters. J Am Chem Soc. 2007 Dec. 26, 2007;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
Yoshina-Ishii et al., Arrays of mobile tethered vesicles on supported lipid bilayers. J Am Chem Soc. Apr. 2, 2003;125(13):3696-7.
Berger et al., Universal bases for hybridization, replication and chain termination. Nucleic Acids Res. Aug. 1, 2000;28(15):2911-4.
Heredia et al., In vitro double transposition for DNA identification. Anal Biochem. Apr. 1, 2010;399(1):78-83. doi:10.1016/j.ab.2009.11.030. Epub Nov. 26, 2009.
Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.

* cited by examiner

SEQUENCE LISTING

```
<160> NUMBER OF SEQ ID NOS: 37

<210> SEQ ID NO 1
<211> LENGTH: 558
<212> TYPE: DNA
<213> ORGANISM: Artificial Sequence
<220> FEATURE:
```

<223> OTHER INFORMATION: Synthetic polynucleotide

<400> SEQUENCE: 1

```
atgggtctgg ataatgaact gagcctggtg gacggtcaag atcgtaccct gacggtgcaa     60
caatgggata cctttctgaa tggcgttttt ccgctggatc gtaatcgcct gacccgtgaa    120
tggtttcatt ccggtcgcgc aaaatatatc gtcgcaggcc cgggtgctga cgaattcgaa    180
ggcacgctgg aactgggtta tcagattggc tttccgtggt cactgggcgt tggtatcaac    240
ttctcgtaca ccacgccgaa tattctgatc aacaatggta acattaccgc accgccgttt    300
ggcctgaaca gcgtgattac gccgaacctg tttccgggtg ttagcatctc tgcccgtctg    360
ggcaatggtc cgggcattca agaagtggca acctttagtg tgcgcgtttc cggcgctaaa    420
ggcggtgtcg cggtgtctaa cgcccacggt accgttacgg gcgcggccgg cggtgtcctg    480
ctgcgtccgt tcgcgcgcct gattgcctct accggcgaca gcgttacgac ctatggcgaa    540
ccgtggaata tgaactaa                                                  558
```

<210> SEQ ID NO 2
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial Sequence
<220> FEATURE:
<223> OTHER INFORMATION: Synthetic polynucleotide

<400> SEQUENCE: 3

-continued

```
atggcagatt ctgatattaa tattaaaacc ggtactacag atattggaag caatactaca     60

gtaaaaacag gtgatttagt cacttatgat aaagaaaatg gcatgcacaa aaaagtattt    120

tatagtttta tcgatgataa aaatcacaat aaaaaactgc tagttattag aacaaaaggt    180

accattgctg gtcaatatag agtttatagc gaagaaggtg ctaacaaaag tggtttagcc    240

tggccttcag cctttaaggt acagttgcaa ctacctgata atgaagtagc tcaaatatct    300

gattactatc caagaaattc gattgataca aaaaactata tgagtacttt aacttatgga    360

ttcaacggta atgttactgg tgatgataca ggaaaaattg gcggccttat tggtgcaaat    420

gtttcgattg gtcatacact gaactatgtt caacctgatt tcaaaacaat tttagagagc    480

ccaactgata aaaaagtagg ctggaaagtg atatttaaca atatggtgaa tcaaaattgg    540

ggaccatacg atcgagattc ttggaacccg gtatatggca atcaactttt catgaaaact    600

agaaatggtt ctatgaaagc agcagataac ttccttgatc ctaacaaagc aagttctcta    660

ttatcttcag ggttttcacc agacttcgct acagttatta ctatggatag aaaagcatcc    720

aaacaacaaa caaatataga tgtaatatac gaacgagttc gtgatgatta ccaattgcat    780

tggacttcaa caaattggaa aggtaccaat actaaagata aatggacaga tcgttcttca    840

gaaagatata aaatcgattg ggaaaaagaa gaaatgacaa attaa                    885
```

<210> SEQ ID NO 4
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205
```

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

```
Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180


<210> SEQ ID NO 8
<211> LENGTH: 1830
<212> TYPE: DNA
<213> ORGANISM: Bacillus subtilis phage phi29

<400> SEQUENCE: 8
```

atgaaacaca tgccgcgtaa aatgtatagc tgcgcgtttg aaaccacgac caaagtggaa 60
gattgtcgcg tttgggccta tggctacatg aacatcgaag atcattctga atacaaaatc 120
ggtaacagtc tggatgaatt tatggcatgg gtgctgaaag ttcaggcgga tctgtacttc 180
cacaacctga aatttgatgg cgcattcatt atcaactggc tggaacgtaa tggctttaaa 240
tggagcgcgg atggtctgcc gaacacgtat aataccatta tctctcgtat gggccagtgg 300
tatatgattg atatctgcct gggctacaaa ggtaaacgca aaattcatac cgtgatctat 360
gatagcctga aaaaactgcc gtttccggtg aagaaaattg cgaaagattt caaactgacg 420
gttctgaaag gcgatattga ttatcacaaa gaacgtccgg ttggttacaa aatcaccccg 480
gaagaatacg catacatcaa aaacgatatc cagatcatcg cagaagcgct gctgattcag 540
tttaaacagg gcctggatcg catgaccgcg ggcagtgata gcctgaaagg tttcaaagat 600
atcatcacga ccaaaaaatt caaaaaagtg ttcccgacgc tgagcctggg tctggataaa 660
gaagttcgtt atgcctaccg cggcggtttt acctggctga acgatcgttt caaagaaaaa 720
gaaattggcg agggtatggt gtttgatgtt aatagtctgt atccggcaca gatgtacagc 780
cgcctgctgc cgtatggcga accgatcgtg ttcgagggta aatatgtttg ggatgaagat 840
tacccgctgc atattcagca catccgttgt gaatttgaac tgaaagaagg ctatattccg 900
accattcaga tcaaacgtag tcgcttctat aagggtaacg aatacctgaa aagctctggc 960
ggtgaaatcg cggatctgtg gctgagtaac gtggatctgg aactgatgaa agaacactac 1020
gatctgtaca acgttgaata catcagcggc ctgaaattta aagccacgac cggtctgttc 1080
aaagatttca tcgataaatg gacctacatc aaaacgacct ctgaaggcgc gattaaacag 1140
ctggccaaac tgatgctgaa cagcctgtat ggcaaattcg cctctaatcc ggatgtgacc 1200
ggtaaagttc cgtacctgaa agaaaatggc gcactgggtt ttcgcctggg cgaagaagaa 1260
acgaaagatc cggtgtatac cccgatgggt gttttcatta cggcctgggc acgttacacg 1320
accatcaccg cggcccaggc atgctatgat cgcattatct actgtgatac cgattctatt 1380
catctgacgg gcaccgaaat cccggatgtg attaaagata tcgttgatcc gaaaaaactg 1440
ggttattggg cccacgaaag tacgtttaaa cgtgcaaaat acctgcgcca gaaaacctac 1500
atccaggata tctacatgaa agaagtggat ggcaaactgg ttgaaggttc tccggatgat 1560
tacaccgata tcaaattcag tgtgaaatgc gccggcatga cggataaaat caaaaaagaa 1620
gtgaccttcg aaaacttcaa agttggtttc agccgcaaaa tgaaaccgaa accggtgcag 1680
gttccgggcg gtgtggttct ggtggatgat acgtttacca ttaaatctgg cggtagtgcg 1740
tggagccatc cgcagttcga aaaaggcggt ggctctggtg gcggttctgg cggtagtgcc 1800
tggagccacc cgcagtttga aaaataataa 1830

<210> SEQ ID NO 9
<211> LENGTH: 608
<212> TYPE: PRT
<213> ORGANISM: Bacillus subtilis phage phi29

<400> SEQUENCE: 9

Met Lys His Met Pro Arg Lys Met Tyr Ser Cys Ala Phe Glu Thr Thr
1 5 10 15

Thr Lys Val Glu Asp Cys Arg Val Trp Ala Tyr Gly Tyr Met Asn Ile
20 25 30

Glu Asp His Ser Glu Tyr Lys Ile Gly Asn Ser Leu Asp Glu Phe Met
35 40 45

-continued

```
Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460
```

-continued

```
Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605
```

<210> SEQ ID NO 10
<211> LENGTH: 1390
<212> TYPE: DNA
<213> ORGANISM: Escherichia coli

<400> SEQUENCE: 10

```
atgatgaacg atggcaaaca gcagagcacc ttcctgtttc atgattatga aaccttcggt     60

acccatccgg ccctggatcg tccggcgcag tttgcggcca ttcgcaccga tagcgaattc    120

aatgtgattg gcgaaccgga agtgttttat tgcaaaccgg ccgatgatta tctgccgcag    180

ccgggtgcgg tgctgattac cggtattacc ccgcaggaag cgcgcgcgaa aggtgaaaac    240

gaagcggcgt ttgccgcgcg cattcatagc ctgtttaccg tgccgaaaac ctgcattctg    300

ggctataaca atgtgcgctt cgatgatgaa gttacccgta atatctttta tcgtaacttt    360

tatgatccgt atgcgtggag ctggcagcat gataacagcc gttgggatct gctggatgtg    420

atgcgcgcgt gctatgcgct gcgcccggaa ggcattaatt ggccggaaaa cgatgatggc    480

ctgccgagct ttcgtctgga acatctgacc aaagccaacg gcattgaaca tagcaatgcc    540

catgatgcga tggccgatgt ttatgcgacc attgcgatgg cgaaactggt taaaacccgt    600

cagccgcgcc tgtttgatta tctgtttacc caccgtaaca aacacaaact gatggcgctg    660

attgatgttc cgcagatgaa accgctggtg catgtgagcg gcatgtttgg cgcctggcgc    720

ggcaacacca gctgggtggc cccgctggcc tggcacccgg aaaatcgtaa cgccgtgatt    780

atggttgatc tggccggtga tattagcccg ctgctggaac tggatagcga taccctgcgt    840

gaacgcctgt ataccgccaa aaccgatctg ggcgataatg ccgccgtgcc ggtgaaactg    900

gttcacatta acaaatgccc ggtgctggcc caggcgaaca ccctgcgccc ggaagatgcg    960

gatcgtctgg gtattaatcg ccagcattgt ctggataatc tgaaaatcct gcgtgaaaac   1020

ccgcaggtgc gtgaaaaagt ggtggcgatc ttcgcggaag cggaaccgtt caccccgagc   1080

gataacgtgg atgcgcagct gtataacggc ttctttagcg atgccgatcg cgcggcgatg   1140

aaaatcgttc tggaaaccga accgcgcaat ctgccggcgc tggatattac ctttgttgat   1200

aaacgtattg aaaaactgct gtttaattat cgtgcgcgca attttccggg taccctggat   1260

tatgccgaac agcagcgttg gctggaacat cgtcgtcagg ttttcacccc ggaatttctg   1320
```

-continued

```
cagggttatg cggatgaact gcagatgctg gttcagcagt atgccgatga taaagaaaaa   1380

gtggcgctgc                                                          1390


<210> SEQ ID NO 11
<211> LENGTH: 485
<212> TYPE: PRT
<213> ORGANISM: Escherichia coli

<400> SEQUENCE: 11

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
```

```
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
                485


<210> SEQ ID NO 12
<211> LENGTH: 804
<212> TYPE: DNA
<213> ORGANISM: Escherichia coli

<400> SEQUENCE: 12

atgaaatttg tctcttttaa tatcaacggc ctgcgcgcca gacctcacca gcttgaagcc      60

atcgtcgaaa agcaccaacc ggatgtgatt ggcctgcagg agacaaaagt tcatgacgat     120

atgtttccgc tcgaagaggt ggcgaagctc ggctacaacg tgttttatca cgggcagaaa     180

ggccattatg gcgtggcgct gctgaccaaa gagacgccga ttgccgtgcg tcgcggcttt     240

cccggtgacg acgaagaggc gcagcggcgg attattatgg cggaaatccc ctcactgctg     300

ggtaatgtca ccgtgatcaa cggttacttc ccgcagggtg aaagccgcga ccatccgata     360

aaattcccgg caaaagcgca gttttatcag aatctgcaaa actacctgga aaccgaactc     420

aaacgtgata atccggtact gattatgggc gatatgaata tcagccctac agatctggat     480

atcggcattg gcgaagaaaa ccgtaagcgc tggctgcgta ccggtaaatg ctctttcctg     540

ccggaagagc gcgaatggat ggacaggctg atgagctggg ggttggtcga taccttccgc     600

catgcgaatc cgcaaacagc agatcgtttc tcatggtttg attaccgctc aaaaggtttt     660

gacgataacc gtggtctgcg catcgacctg ctgctcgcca gccaaccgct ggcagaatgt     720

tgcgtagaaa ccggcatcga ctatgaaatc cgcagcatgg aaaaaccgtc cgatcacgcc     780

cccgtctggg cgaccttccg ccgc                                            804


<210> SEQ ID NO 13
<211> LENGTH: 268
<212> TYPE: PRT
<213> ORGANISM: Escherichia coli

<400> SEQUENCE: 13

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45
```

```
Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60

cgcgaagccg ccgcactgct ggaagaagcg ctgcgtcaag gtaaacgcat tcgtgttcac     120

ggcgactatg atgcggatgg cctgaccggc accgcgatcc tggttcgtgg tctggccgcc     180

ctgggtgcgg atgttcatcc gtttatcccg caccgcctgg aagaaggcta tggtgtcctg     240

atggaacgcg tcccggaaca tctggaagcc tcggacctgt ttctgaccgt tgactgcggc     300

attaccaacc atgcggaact gcgcgaactg ctggaaaatg gcgtggaagt cattgttacc     360

gatcatcata cgccgggcaa aacgccgccg ccgggtctgg tcgtgcatcc ggcgctgacg     420

ccggatctga aagaaaaacc gaccggcgca ggcgtggcgt ttctgctgct gtgggcactg     480

catgaacgcc tgggcctgcc gccgccgctg gaatacgcgg acctggcagc cgttggcacc     540

attgccgacg ttgccccgct gtggggttgg aatcgtgcac tggtgaaaga aggtctggca     600

cgcatcccgg cttcatcttg ggtgggcctg cgtctgctgg ctgaagccgt gggctatacc     660

ggcaaagcgg tcgaagtcgc tttccgcatc gcgccgcgca tcaatgcggc ttcccgcctg     720

ggcgaagcgg aaaaagccct gcgcctgctg ctgacggatg atgcggcaga agctcaggcg     780

ctggtcggcg aactgcaccg tctgaacgcc cgtcgtcaga ccctggaaga agcgatgctg     840

cgcaaactgc tgccgcaggc cgacccggaa gcgaaagcca tcgttctgct ggacccggaa     900
```

```
ggccatccgg gtgttatggg tattgtggcc tctcgcatcc tggaagcgac cctgcgcccg    960

gtctttctgg tggcccaggg caaaggcacc gtgcgttcgc tggctccgat ttccgccgtc   1020

gaagcactgc gcagcgcgga agatctgctg ctgcgttatg gtggtcataa agaagcggcg   1080

ggtttcgcaa tggatgaagc gctgtttccg gcgttcaaag cacgcgttga agcgtatgcc   1140

gcacgtttcc cggatccggt tcgtgaagtg gcactgctgg atctgctgcc ggaaccgggc   1200

ctgctgccgc aggtgttccg tgaactggca ctgctggaac cgtatggtga aggtaacccg   1260

gaaccgctgt tcctg                                                   1275


<210> SEQ ID NO 15
<211> LENGTH: 425
<212> TYPE: PRT
<213> ORGANISM: Thermus thermophilus

<400> SEQUENCE: 15

Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300
```

```
Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425
```

<210> SEQ ID NO 16
<211> LENGTH: 738
<212> TYPE: DNA
<213> ORGANISM: Bacteriophage lambda

<400> SEQUENCE: 16

```
tccggaagcg gctctggtag tggttctggc atgacaccgg acattatcct gcagcgtacc      60

gggatcgatg tgagagctgt cgaacagggg gatgatgcgt ggcacaaatt acggctcggc     120

gtcatcaccg cttcagaagt tcacaacgtg atagcaaaac cccgctccgg aaagaagtgg     180

cctgacatga aaatgtccta cttccacacc ctgcttgctg aggtttgcac cggtgtggct     240

ccggaagtta acgctaaagc actggcctgg ggaaaacagt acgagaacga cgccagaacc     300

ctgtttgaat tcacttccgg cgtgaatgtt actgaatccc cgatcatcta tcgcgacgaa     360

agtatgcgta ccgcctgctc tcccgatggt ttatgcagtg acggcaacgg ccttgaactg     420

aaatgcccgt ttacctcccg ggatttcatg aagttccggc tcggtggttt cgaggccata     480

aagtcagctt acatggccca ggtgcagtac agcatgtggg tgacgcgaaa aaatgcctgg     540

tactttgcca actatgaccc gcgtatgaag cgtgaaggcc tgcattatgt cgtgattgag     600

cgggatgaaa agtacatggc gagttttgac gagatcgtgc cggagttcat cgaaaaaatg     660

gacgaggcac tggctgaaat tggttttgta tttggggagc aatggcgatc tggctctggt     720

tccggcagcg gttccgga                                                   738
```

<210> SEQ ID NO 17
<211> LENGTH: 226
<212> TYPE: PRT
<213> ORGANISM: Bacteriophage lambda

<400> SEQUENCE: 17

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60
```

```
Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225


<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205
```

-continued

```
Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
    610                 615                 620
```

```
Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
    690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760


<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Gly Pro Ala Val Asp
225                 230                 235                 240
```

-continued

```
Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
                325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
    610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655
```

```
Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
    690                 695                 700

Lys Gly Gly
705


<210> SEQ ID NO 20
<211> LENGTH: 720
<212> TYPE: PRT
<213> ORGANISM: Thermococcus gammatolerans

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320
```

```
Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
    450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
    610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
        675                 680                 685

Lys Ile Leu Asp Gly Ile Tyr Arg His Leu Gly Ile Glu Lys Arg Val
    690                 695                 700

Thr Glu Glu Lys Pro Lys Arg Lys Gly Thr Leu Glu Asp Phe Leu Arg
705                 710                 715                 720
```

<210> SEQ ID NO 21
<211> LENGTH: 799

<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1 5 10 15

His Ala Lys Gly Ile Arg Ser Leu Tyr Pro Pro Gln Ala Glu Cys Ile
20 25 30

Glu Lys Gly Leu Leu Glu Gly Lys Asn Leu Leu Ile Ser Ile Pro Thr
35 40 45

Ala Ser Gly Lys Thr Leu Leu Ala Glu Met Ala Met Trp Ser Arg Ile
50 55 60

Ala Ala Gly Gly Lys Cys Leu Tyr Ile Val Pro Leu Arg Ala Leu Ala
65 70 75 80

Ser Glu Lys Tyr Asp Glu Phe Ser Lys Lys Gly Val Ile Arg Val Gly
85 90 95

Ile Ala Thr Gly Asp Leu Asp Arg Thr Asp Ala Tyr Leu Gly Glu Asn
100 105 110

Asp Ile Ile Val Ala Thr Ser Glu Lys Thr Asp Ser Leu Leu Arg Asn
115 120 125

Arg Thr Pro Trp Leu Ser Gln Ile Thr Cys Ile Val Leu Asp Glu Val
130 135 140

His Leu Ile Gly Ser Glu Asn Arg Gly Ala Thr Leu Glu Met Val Ile
145 150 155 160

Thr Lys Leu Arg Tyr Thr Asn Pro Val Met Gln Ile Ile Gly Leu Ser
165 170 175

Ala Thr Ile Gly Asn Pro Ala Gln Leu Ala Glu Trp Leu Asp Ala Thr
180 185 190

Leu Ile Thr Ser Thr Trp Arg Pro Val Asp Leu Arg Gln Gly Val Tyr
195 200 205

Tyr Asn Gly Lys Ile Arg Phe Ser Asp Ser Glu Arg Pro Ile Gln Gly
210 215 220

Lys Thr Lys His Asp Asp Leu Asn Leu Cys Leu Asp Thr Ile Glu Glu
225 230 235 240

Gly Gly Gln Cys Leu Val Phe Val Ser Ser Arg Arg Asn Ala Glu Gly
245 250 255

Phe Ala Lys Lys Ala Ala Gly Ala Leu Lys Ala Gly Ser Pro Asp Ser
260 265 270

Lys Ala Leu Ala Gln Glu Leu Arg Arg Leu Arg Asp Arg Asp Glu Gly
275 280 285

Asn Val Leu Ala Asp Cys Val Glu Arg Gly Ala Ala Phe His His Ala
290 295 300

Gly Leu Ile Arg Gln Glu Arg Thr Ile Ile Glu Glu Gly Phe Arg Asn
305 310 315 320

Gly Tyr Ile Glu Val Ile Ala Ala Thr Pro Thr Leu Ala Ala Gly Leu
325 330 335

Asn Leu Pro Ala Arg Arg Val Ile Ile Arg Asp Tyr Asn Arg Phe Ala
340 345 350

Ser Gly Leu Gly Met Val Pro Ile Pro Val Gly Glu Tyr His Gln Met
355 360 365

Ala Gly Arg Ala Gly Arg Pro His Leu Asp Pro Tyr Gly Glu Ala Val
370 375 380

Leu Leu Ala Lys Asp Ala Pro Ser Val Glu Arg Leu Phe Glu Thr Phe
385 390 395 400

```
Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
        515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
        755                 760                 765

Ser Glu Lys Glu Asn Ser Ser Ser Asp Lys Thr Glu Glu Ile Pro Asp
    770                 775                 780

Thr Gln Lys Ile Arg Gly Gln Ser Ser Trp Glu Asp Phe Gly Cys
785                 790                 795
```

<210> SEQ ID NO 22
<211> LENGTH: 1756

<212> TYPE: PRT
<213> ORGANISM: Escherichia coli

<400> SEQUENCE: 22

```
Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400
```

-continued

```
Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815
```

```
Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr  Gln Phe Arg Ala Val  Met Ser Ala
        995                 1000                1005

Val Asn  Met Leu Pro Ala Ser  Glu Arg Pro Arg Val  Val Gly Leu
    1010                1015                1020

Gly Pro  Thr His Arg Ala Val  Gly Glu Met Arg Ser  Ala Gly Val
    1025                1030                1035

Asp Ala  Gln Thr Leu Ala Ser  Phe Leu His Asp Thr  Gln Leu Gln
    1040                1045                1050

Gln Arg  Ser Gly Glu Thr Pro  Asp Phe Ser Asn Thr  Leu Phe Leu
    1055                1060                1065

Leu Asp  Glu Ser Ser Met Val  Gly Asn Thr Glu Met  Ala Arg Ala
    1070                1075                1080

Tyr Ala  Leu Ile Ala Ala Gly  Gly Gly Arg Ala Val  Ala Ser Gly
    1085                1090                1095

Asp Thr  Asp Gln Leu Gln Ala  Ile Ala Pro Gly Gln  Ser Phe Arg
    1100                1105                1110

Leu Gln  Gln Thr Arg Ser Ala  Ala Asp Val Val Ile  Met Lys Glu
    1115                1120                1125

Ile Val  Arg Gln Thr Pro Glu  Leu Arg Glu Ala Val  Tyr Ser Leu
    1130                1135                1140

Ile Asn  Arg Asp Val Glu Arg  Ala Leu Ser Gly Leu  Glu Ser Val
    1145                1150                1155

Lys Pro  Ser Gln Val Pro Arg  Leu Glu Gly Ala Trp  Ala Pro Glu
    1160                1165                1170

His Ser  Val Thr Glu Phe Ser  His Ser Gln Glu Ala  Lys Leu Ala
    1175                1180                1185

Glu Ala  Gln Gln Lys Ala Met  Leu Lys Gly Glu Ala  Phe Pro Asp
    1190                1195                1200

Ile Pro  Met Thr Leu Tyr Glu  Ala Ile Val Arg Asp  Tyr Thr Gly
    1205                1210                1215

Arg Thr  Pro Glu Ala Arg Glu  Gln Thr Leu Ile Val  Thr His Leu
```

-continued

```
    1220                1225                1230

Asn Glu  Asp Arg Arg Val Leu  Asn Ser Met Ile His  Asp Ala Arg
    1235                1240                1245

Glu Lys  Ala Gly Glu Leu Gly  Lys Glu Gln Val Met  Val Pro Val
    1250                1255                1260

Leu Asn  Thr Ala Asn Ile Arg  Asp Gly Glu Leu Arg  Arg Leu Ser
    1265                1270                1275

Thr Trp  Glu Lys Asn Pro Asp  Ala Leu Ala Leu Val  Asp Asn Val
    1280                1285                1290

Tyr His  Arg Ile Ala Gly Ile  Ser Lys Asp Asp Gly  Leu Ile Thr
    1295                1300                1305

Leu Gln  Asp Ala Glu Gly Asn  Thr Arg Leu Ile Ser  Pro Arg Glu
    1310                1315                1320

Ala Val  Ala Glu Gly Val Thr  Leu Tyr Thr Pro Asp  Lys Ile Arg
    1325                1330                1335

Val Gly  Thr Gly Asp Arg Met  Arg Phe Thr Lys Ser  Asp Arg Glu
    1340                1345                1350

Arg Gly  Tyr Val Ala Asn Ser  Val Trp Thr Val Thr  Ala Val Ser
    1355                1360                1365

Gly Asp  Ser Val Thr Leu Ser  Asp Gly Gln Gln Thr  Arg Val Ile
    1370                1375                1380

Arg Pro  Gly Gln Glu Arg Ala  Glu Gln His Ile Asp  Leu Ala Tyr
    1385                1390                1395

Ala Ile  Thr Ala His Gly Ala  Gln Gly Ala Ser Glu  Thr Phe Ala
    1400                1405                1410

Ile Ala  Leu Glu Gly Thr Glu  Gly Asn Arg Lys Leu  Met Ala Gly
    1415                1420                1425

Phe Glu  Ser Ala Tyr Val Ala  Leu Ser Arg Met Lys  Gln His Val
    1430                1435                1440

Gln Val  Tyr Thr Asp Asn Arg  Gln Gly Trp Thr Asp  Ala Ile Asn
    1445                1450                1455

Asn Ala  Val Gln Lys Gly Thr  Ala His Asp Val Leu  Glu Pro Lys
    1460                1465                1470

Pro Asp  Arg Glu Val Met Asn  Ala Gln Arg Leu Phe  Ser Thr Ala
    1475                1480                1485

Arg Glu  Leu Arg Asp Val Ala  Ala Gly Arg Ala Val  Leu Arg Gln
    1490                1495                1500

Ala Gly  Leu Ala Gly Gly Asp  Ser Pro Ala Arg Phe  Ile Ala Pro
    1505                1510                1515

Gly Arg  Lys Tyr Pro Gln Pro  Tyr Val Ala Leu Pro  Ala Phe Asp
    1520                1525                1530

Arg Asn  Gly Lys Ser Ala Gly  Ile Trp Leu Asn Pro  Leu Thr Thr
    1535                1540                1545

Asp Asp  Gly Asn Gly Leu Arg  Gly Phe Ser Gly Glu  Gly Arg Val
    1550                1555                1560

Lys Gly  Ser Gly Asp Ala Gln  Phe Val Ala Leu Gln  Gly Ser Arg
    1565                1570                1575

Asn Gly  Glu Ser Leu Leu Ala  Asp Asn Met Gln Asp  Gly Val Arg
    1580                1585                1590

Ile Ala  Arg Asp Asn Pro Asp  Ser Gly Val Val Val  Arg Ile Ala
    1595                1600                1605

Gly Glu  Gly Arg Pro Trp Asn  Pro Gly Ala Ile Thr  Gly Gly Arg
    1610                1615                1620
```

```
Val Trp  Gly Asp Ile Pro Asp  Asn Ser Val Gln Pro  Gly Ala Gly
    1625                 1630                 1635

Asn Gly  Glu Pro Val Thr Ala  Glu Val Leu Ala Gln  Arg Gln Ala
    1640                 1645                 1650

Glu Glu  Ala Ile Arg Arg Glu  Thr Glu Arg Arg Ala  Asp Glu Ile
    1655                 1660                 1665

Val Arg  Lys Met Ala Glu Asn  Lys Pro Asp Leu Pro  Asp Gly Lys
    1670                 1675                 1680

Thr Glu  Leu Ala Val Arg Asp  Ile Ala Gly Gln Glu  Arg Asp Arg
    1685                 1690                 1695

Ser Ala  Ile Ser Glu Arg Glu  Thr Ala Leu Pro Glu  Ser Val Leu
    1700                 1705                 1710

Arg Glu  Ser Gln Arg Glu Arg  Glu Ala Val Arg Glu  Val Ala Arg
    1715                 1720                 1725

Glu Asn  Leu Leu Gln Glu Arg  Leu Gln Gln Met Glu  Arg Asp Met
    1730                 1735                 1740

Val Arg  Asp Leu Gln Lys Glu  Lys Thr Leu Gly Gly  Asp
    1745                 1750                 1755


<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
```

-continued

```
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365

Gln Ile Leu Leu Ser Glu Ala Ser Glu Leu Gly Ala Lys Leu Asp Glu
    370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
    450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655
```

```
Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725


<210> SEQ ID NO 24
<211> LENGTH: 439
<212> TYPE: PRT
<213> ORGANISM: Enterobacteria phage T4

<400> SEQUENCE: 24

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
```

```
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435


<210> SEQ ID NO 25
<211> LENGTH: 970
<212> TYPE: PRT
<213> ORGANISM: Clostridium botulinum

<400> SEQUENCE: 25

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220
```

-continued

```
Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Ala Gln Ala Gly Asp Val
625                 630                 635                 640

Arg Lys Ala Leu Arg His Leu Lys Ser His Thr Val Glu Ala Arg Gly
```

```
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
    770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
    930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970
```

<210> SEQ ID NO 26
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 26
gttttcgcat ttatcgtgaa acgctttcgc gtttttcgtg cgccgcttca 50

<210> SEQ ID NO 27
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 27
caaaagcgta aatagcactt tgcgaaagcg caaaaagcac gcggcgaagt 50

<210> SEQ ID NO 28
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 28
caaaagcgta aatagcactt tgcgaaagcg caaaaagcac gcggcgaagt ctag 54

<210> SEQ ID NO 29
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 29
gcgttctgtt tcggatgtat gttttcatac atccgaaaca gaacgctttt gttttcgcat 60
ttatcgtgaa acgctttcgc gtttttcgtg cgccgcttca 100

<210> SEQ ID NO 30
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 30
gaagcggcgc acgaaaaacg cgaaagcgtt tcacgataat gcgaaaac 48

<210> SEQ ID NO 31
<211> LENGTH: 48502
<212> TYPE: DNA
<213> ORGANISM: Artificial Sequence
<220> FEATURE:
<223> OTHER INFORMATION: Synthetic polynucleotide

<400> SEQUENCE: 31
gggcggcgac ctcgcgggtt ttcgctattt atgaaaattt tccggtttaa ggcgtttccg 60
ttcttcttcg tcataactta atgtttttat ttaaaatacc ctctgaaaag aaaggaaacg 120
acaggtgctg aaagcgaggc tttttggcct ctgtcgtttc ctttctctgt ttttgtccgt 180
ggaatgaaca atggaagtca acaaaaagca gctggctgac attttcggtg cgagtatccg 240
taccattcag aactggcagg aacagggaat gcccgttctg cgaggcggtg gcaagggtaa 300
tgaggtgctt tatgactctg ccgccgtcat aaaatggtat gccgaaaggg atgctgaaat 360
tgagaacgaa aagctgcgcc gggaggttga agaactgcgg caggccagcg aggcagatct 420
ccagccagga actattgagt acgaacgcca tcgacttacg cgtgcgcagg ccgacgcaca 480
ggaactgaag aatgccagag actccgctga agtggtggaa accgcattct gtactttcgt 540
gctgtcgcgg atcgcaggtg aaattgccag tattctcgac gggctccccc tgtcggtgca 600
gcggcgtttt ccggaactgg aaaaccgaca tgttgatttc ctgaaacggg atatcatcaa 660
agccatgaac aaagcagccg cgctggatga actgataccg ggggttgctga gtgaatatat 720

-continued

```
cgaacagtca ggttaacagg ctgcggcatt ttgtccgcgc cgggcttcgc tcactgttca    780
ggccggagcc acagaccgcc gttgaatggg cggatgctaa ttactatctc ccgaaagaat    840
ccgcatacca ggaagggcgc tgggaaacac tgccctttca gcgggccatc atgaatgcga    900
tgggcagcga ctacatccgt gaggtgaatg tggtgaagtc tgcccgtgtc ggttattcca    960
aaatgctgct gggtgtttat gcctacttta tagagcataa gcagcgcaac acccttatct   1020
ggttgccgac ggatggtgat gccgagaact ttatgaaaac ccacgttgag ccgactattc   1080
gtgatattcc gtcgctgctg gcgctggccc cgtggtatgg caaaaagcac cgggataaca   1140
cgctcaccat gaagcgtttc actaatgggc gtggcttctg gtgcctgggc ggtaaagcgg   1200
caaaaaacta ccgtgaaaag tcggtggatg tggcgggtta tgatgaactt gctgcttttg   1260
atgatgatat tgaacaggaa ggctctccga cgttcctggg tgacaagcgt attgaaggct   1320
cggtctggcc aaagtccatc cgtggctcca cgccaaaagt gagaggcacc tgtcagattg   1380
agcgtgcagc cagtgaatcc ccgcatttta tgcgttttca tgttgcctgc ccgcattgcg   1440
gggaggagca gtatcttaaa tttggcgaca aagagacgcc gtttggcctc aaatggacgc   1500
cggatgaccc ctccagcgtg ttttatctct gcgagcataa tgcctgcgtc atccgccagc   1560
aggagctgga ctttactgat gcccgttata tctgcgaaaa gaccgggatc tggacccgtg   1620
atggcattct ctggttttcg tcatccggtg aagagattga gccacctgac agtgtgacct   1680
ttcacatctg gacagcgtac agcccgttca ccacctgggt gcagattgtc aaagactgga   1740
tgaaaacgaa aggggatacg ggaaaacgta aaaccttcgt aaacaccacg ctcggtgaga   1800
cgtgggaggc gaaaattggc gaacgtccgg atgctgaagt gatggcagag cggaaagagc   1860
attattcagc gcccgttcct gaccgtgtgg cttacctgac cgccggtatc gactcccagc   1920
tggaccgcta cgaaatgcgc gtatggggat gggggccggg tgaggaaagc tggctgattg   1980
accggcagat tattatgggc cgccacgacg atgaacagac gctgctgcgt gtggatgagg   2040
ccatcaataa aacctatacc cgccggaatg gtgcagaaat gtcgatatcc cgtatctgct   2100
gggatactgg cgggattgac ccgaccattg tgtatgaacg ctcgaaaaaa catgggctgt   2160
tccgggtgat ccccattaaa ggggcatccg tctacggaaa gccggtggcc agcatgccac   2220
gtaagcgaaa caaaaacggg gtttacctta ccgaaatcgg tacggatacc gcgaaagagc   2280
agatttataa ccgcttcaca ctgacgccgg aaggggatga accgcttccc ggtgccgttc   2340
acttcccgaa taacccggat atttttgatc tgaccgaagc gcagcagctg actgctgaag   2400
agcaggtcga aaaatgggtg gatggcagga aaaaaatact gtgggacagc aaaaagcgac   2460
gcaatgaggc actcgactgc ttcgtttatg cgctggcggc gctgcgcatc agtatttccc   2520
gctggcagct ggatctcagt gcgctgctgg cgagcctgca ggaagaggat ggtgcagcaa   2580
ccaacaagaa aacactggca gattacgccc gtgccttatc cggagaggat gaatgacgcg   2640
acaggaagaa cttgccgctg cccgtgcggc actgcatgac ctgatgacag gtaaacgggt   2700
ggcaacagta cagaaagacg gacgaagggt ggagtttacg gccacttccg tgtctgacct   2760
gaaaaaatat attgcagagc tggaagtgca gaccggcatg acacagcgac gcaggggacc   2820
tgcaggattt tatgtatgaa aacgcccacc attcccaccc ttctggggcc ggacggcatg   2880
acatcgctgc gcgaatatgc cggttatcac ggcggtggca gcggatttgg agggcagttg   2940
cggtcgtgga acccaccgag tgaaagtgtg gatgcagccc tgttgcccaa ctttacccgt   3000
ggcaatgccc gcgcagacga tctggtacgc aataacggct atgccgccaa cgccatccag   3060
ctgcatcagg atcatatcgt cgggtctttt ttccggctca gtcatcgccc aagctggcgc   3120
```

```
tatctgggca tcggggagga agaagcccgt gccttttccc gcgaggttga agcggcatgg   3180
aaagagtttg ccgaggatga ctgctgctgc attgacgttg agcgaaaacg cacgtttacc   3240
atgatgattc gggaaggtgt ggccatgcac gcctttaacg gtgaactgtt cgttcaggcc   3300
acctgggata ccagttcgtc gcggcttttc cggacacagt tccggatggt cagcccgaag   3360
cgcatcagca acccgaacaa taccggcgac agccggaact gccgtgccgg tgtgcagatt   3420
aatgacagcg gtgcggcgct gggatattac gtcagcgagg acgggtatcc tggctggatg   3480
ccgcagaaat ggacatggat accccgtgag ttacccggcg ggcgcgcctc gttcattcac   3540
gtttttgaac ccgtggagga cgggcagact cgcggtgcaa atgtgtttta cagcgtgatg   3600
gagcagatga agatgctcga cacgctgcag aacacgcagc tgcagagcgc cattgtgaag   3660
gcgatgtatg ccgccaccat tgagagtgag ctggatacgc agtcagcgat ggattttatt   3720
ctgggcgcga acagtcagga gcagcgggaa aggctgaccg gctggattgg tgaaattgcc   3780
gcgtattacg ccgcagcgcc ggtccggctg ggaggcgcaa aagtaccgca cctgatgccg   3840
ggtgactcac tgaacctgca gacggctcag gatacggata acggctactc cgtgtttgag   3900
cagtcactgc tgcggtatat cgctgccggg ctgggtgtct cgtatgagca gctttcccgg   3960
aattacgccc agatgagcta ctccacggca cgggccagtg cgaacgagtc gtgggcgtac   4020
tttatggggc ggcgaaaatt cgtcgcatcc cgtcaggcga gccagatgtt tctgtgctgg   4080
ctggaagagg ccatcgttcg ccgcgtggtg acgttacctt caaaagcgcg cttcagtttt   4140
caggaagccc gcagtgcctg gggaactgc gactggatag gctccggtcg tatggccatc    4200
gatggtctga aagaagttca ggaagcggtg atgctgatag aagccggact gagtacctac   4260
gagaaagagt gcgcaaaacg cggtgacgac tatcaggaaa tttttgccca gcaggtccgt   4320
gaaacgatgg agcgccgtgc agccggtctt aaaccgcccg cctgggcggc tgcagcattt   4380
gaatccgggc tgcgacaatc aacagaggag gagaagagtg acagcagagc tgcgtaatct   4440
cccgcatatt gccagcatgg cctttaatga gccgctgatg cttgaacccg cctatgcgcg   4500
ggttttcttt tgtgcgcttg caggccagct tgggatcagc agcctgacgg atgcggtgtc   4560
cggcgacagc ctgactgccc aggaggcact cgcgacgctg gcattatccg gtgatgatga   4620
cggaccacga caggcccgca gttatcaggt catgaacggc atcgccgtgc tgccggtgtc   4680
cggcacgctg gtcagccgga cgcgggcgct gcagccgtac tcggggatga ccggttacaa   4740
cggcattatc gcccgtctgc aacaggctgc cagcgatccg atggtggacg gcattctgct   4800
cgatatggac acgcccggcg ggatggtggc gggggcattt gactgcgctg acatcatcgc   4860
ccgtgtgcgt gacataaaac cggtatgggc gcttgccaac gacatgaact gcagtgcagg   4920
tcagttgctt gccagtgccg cctcccggcg tctggtcacg cagaccgccc ggacaggctc   4980
catcggcgtc atgatggctc acagtaatta cggtgctgcg ctggagaaac agggtgtgga   5040
aatcacgctg atttacagcg gcagccataa ggtggatggc aaccccctaca gccatcttcc  5100
ggatgacgtc cgggagacac tgcagtcccg gatggacgca acccgccaga tgtttgcgca   5160
gaaggtgtcg gcatataccg gcctgtccgt gcaggttgtg ctggataccg aggctgcagt   5220
gtacagcggt caggaggcca ttgatgccgg actggctgat gaacttgtta acagcaccga   5280
tgcgatcacc gtcatgcgtg atgcactgga tgcacgtaaa tcccgtctct caggagggcg   5340
aatgaccaaa gagactcaat caacaactgt ttcagccact gcttcgcagg ctgacgttac   5400
tgacgtggtg ccagcgacgg agggcgagaa cgccagcgcg gcgcagccgg acgtgaacgc   5460
```

-continued gcagatcacc gcagcggttg cggcagaaaa cagccgcatt atggggatcc tcaactgtga 5520
ggaggctcac ggacgcgaag aacaggcacg cgtgctggca gaaacccccg gtatgaccgt 5580
gaaaacggcc cgccgcattc tggccgcagc accacagagt gcacaggcgc gcagtgacac 5640
tgcgctggat cgtctgatgc agggggcacc ggcaccgctg gctgcaggta acccggcatc 5700
tgatgccgtt aacgatttgc tgaacacacc agtgtaaggg atgtttatga cgagcaaaga 5760
aacctttacc cattaccagc cgcagggcaa cagtgacccg gctcataccg caaccgcgcc 5820
cggcggattg agtgcgaaag cgcctgcaat gaccccgctg atgctggaca cctccagccg 5880
taagctggtt gcgtgggatg gcaccaccga cggtgctgcc gttggcattc ttgcggttgc 5940
tgctgaccag accagcacca cgctgacgtt ctacaagtcc ggcacgttcc gttatgagga 6000
tgtgctctgg ccggaggctg ccagcgacga gacgaaaaaa cggaccgcgt ttgccggaac 6060
ggcaatcagc atcgtttaac tttacccttc atcactaaag gccgcctgtg cggctttttt 6120
tacgggattt ttttatgtcg atgtacacaa ccgcccaact gctggcggca aatgagcaga 6180
aatttaagtt tgatccgctg tttctgcgtc tctttttccg tgagagctat cccttcacca 6240
cggagaaagt ctatctctca caaattccgg gactggtaaa catggcgctg tacgtttcgc 6300
cgattgtttc cggtgaggtt atccgttccc gtggcggctc cacctctgaa tttacgccgg 6360
gatatgtcaa gccgaagcat gaagtgaatc cgcagatgac cctgcgtcgc ctgccggatg 6420
aagatccgca gaatctggcg gacccggctt accgccgccg tcgcatcatc atgcagaaca 6480
tgcgtgacga agagctggcc attgctcagg tcgaagagat gcaggcagtt tctgccgtgc 6540
ttaagggcaa atacaccatg accggtgaag ccttcgatcc ggttgaggtg gatatgggcc 6600
gcagtgagga gaataacatc acgcagtccg gcggcacgga gtggagcaag cgtgacaagt 6660
ccacgtatga cccgaccgac gatatcgaag cctacgcgct gaacgccagc ggtgtggtga 6720
atatcatcgt gttcgatccg aaaggctggg cgctgttccg ttccttcaaa gccgtcaagg 6780
agaagctgga tacccgtcgt ggctctaatt ccgagctgga gacagcggtg aaagacctgg 6840
gcaaagcggt gtcctataag gggatgtatg gcgatgtggc catcgtcgtg tattccggac 6900
agtacgtgga aaacggcgtc aaaaagaact tcctgccgga caacacgatg gtgctgggga 6960
acactcaggc acgcggtctg cgcacctatg gctgcattca ggatgcggac gcacagcgcg 7020
aaggcattaa cgcctctgcc cgttacccga aaaactgggt gaccaccggc gatccggcgc 7080
gtgagttcac catgattcag tcagcaccgc tgatgctgct ggctgaccct gatgagttcg 7140
tgtccgtaca actggcgtaa tcatggccct tcggggccat tgtttctctg tggaggagtc 7200
catgacgaaa gatgaactga ttgcccgtct ccgctcgctg ggtgaacaac tgaaccgtga 7260
tgtcagcctg acggggacga aagaagaact ggcgctccgt gtggcagagc tgaaagagga 7320
gcttgatgac acggatgaaa ctgccggtca ggacacccct ctcagccggg aaaatgtgct 7380
gaccggacat gaaaatgagg tgggatcagc gcagccggat accgtgattc tggatacgtc 7440
tgaactggtc acggtcgtgg cactggtgaa gctgcatact gatgcacttc acgccacgcg 7500
ggatgaacct gtggcatttg tgctgccggg aacggcgttt cgtgtctctg ccggtgtggc 7560
agccgaaatg acagagcgcg gcctggccag aatgcaataa cgggaggcgc tgtggctgat 7620
ttcgataacc tgttcgatgc tgccattgcc cgcgccgatg aaacgatacg cgggtacatg 7680
ggaacgtcag ccaccattac atccggtgag cagtcaggtg cggtgatacg tggtgttttt 7740
gatgaccctg aaaatatcag ctatgccgga cagggcgtgc gcgttgaagg ctccagcccg 7800
tccctgtttg tccggactga tgaggtgcgg cagctgcggc gtggagacac gctgaccatc 7860
ggtgaggaaa atttctgggt agatcgggtt tcgccggatg atggcggaag ttgtcatctc 7920
tggcttggac ggggcgtacc gcctgccgtt aaccgtcgcc gctgaaaggg ggatgtatgg 7980
ccataaaagg tcttgagcag gccgttgaaa acctcagccg tatcagcaaa acggcggtgc 8040
ctggtgccgc cgcaatggcc attaaccgcg ttgcttcatc cgcgatatcg cagtcggcgt 8100
cacaggttgc ccgtgagaca aaggtacgcc ggaaactggt aaaggaaagg gccaggctga 8160
aaagggccac ggtcaaaaat ccgcaggcca gaatcaaagt taaccggggg gatttgcccg 8220
taatcaagct gggtaatgcg cgggttgtcc tttcgcgccg caggcgtcgt aaaaaggggc 8280
agcgttcatc cctgaaaggt ggcggcagcg tgcttgtggt gggtaaccgt cgtattcccg 8340
gcgcgtttat tcagcaactg aaaaatggcc ggtggcatgt catgcagcgt gtggctggga 8400
aaaaccgtta ccccattgat gtggtgaaaa tcccgatggc ggtgccgctg accacggcgt 8460
ttaaacaaaa tattgagcgg atacggcgtg aacgtcttcc gaaagagctg ggctatgcgc 8520
tgcagcatca actgaggatg gtaataaagc gatgaaacat actgaactcc gtgcagccgt 8580
actggatgca ctggagaagc atgacaccgg ggcgacgttt tttgatggtc gccccgctgt 8640
ttttgatgag gcggattttc cggcagttgc cgtttatctc accggcgctg aatacacggg 8700
cgaagagctg gacagcgata cctggcaggc ggagctgcat atcgaagttt tcctgcctgc 8760
tcaggtgccg gattcagagc tggatgcgtg gatggagtcc cggatttatc cggtgatgag 8820
cgatatcccg gcactgtcag atttgatcac cagtatggtg gccagcggct atgactaccg 8880
gcgcgacgat gatgcgggct tgtggagttc agccgatctg acttatgtca ttacctatga 8940
aatgtgagga cgctatgcct gtaccaaatc ctacaatgcc ggtgaaaggt gccgggacca 9000
ccctgtgggt ttataagggg agcggtgacc cttacgcgaa tccgctttca gacgttgact 9060
ggtcgcgtct ggcaaaagtt aaagacctga cgcccggcga actgaccgct gagtcctatg 9120
acgacagcta tctcgatgat gaagatgcag actggactgc gaccgggcag gggcagaaat 9180
ctgccggaga taccagcttc acgctggcgt ggatgcccgg agagcagggg cagcaggcgc 9240
tgctggcgtg gtttaatgaa ggcgataccc gtgcctataa aatccgcttc ccgaacggca 9300
cggtcgatgt gttccgtggc tgggtcagca gtatcggtaa ggcggtgacg gcgaaggaag 9360
tgatcacccg cacggtgaaa gtcaccaatg tgggacgtcc gtcgatggca gaagatcgca 9420
gcacggtaac agcggcaacc ggcatgaccg tgacgcctgc cagcacctcg gtggtgaaag 9480
ggcagagcac cacgctgacc gtggccttcc agccggaggg cgtaaccgac aagagctttc 9540
gtgcggtgtc tgcggataaa acaaaagcca ccgtgtcggt cagtggtatg accatcaccg 9600
tgaacggcgt tgctgcaggc aaggtcaaca ttccggttgt atccggtaat ggtgagtttg 9660
ctgcggttgc agaaattacc gtcaccgcca gttaatccgg agagtcagcg atgttcctga 9720
aaaccgaatc atttgaacat aacggtgtga ccgtcacgct ttctgaactg tcagccctgc 9780
agcgcattga gcatctcgcc ctgatgaaac ggcaggcaga acaggcggag tcagacagca 9840
accggaagtt tactgtggaa gacgccatca gaaccggcgc gtttctggtg gcgatgtccc 9900
tgtggcataa ccatccgcag aagacgcaga tgccgtccat gaatgaagcc gttaaacaga 9960
ttgagcagga agtgcttacc acctggccca cggaggcaat ttctcatgct gaaaacgtgg 10020
tgtaccggct gtctggtatg tatgagtttg tggtgaataa tgcccctgaa cagacagagg 10080
acgccgggcc cgcagagcct gtttctgcgg gaaagtgttc gacggtgagc tgagttttgc 10140
cctgaaactg gcgcgtgaga tggggcgacc cgactggcgt gccatgcttg ccgggatgtc 10200

-continued atccacggag tatgccgact ggcaccgctt ttacagtacc cattattttc atgatgttct 10260
gctggatatg cacttttccg ggctgacgta caccgtgctc agcctgtttt tcagcgatcc 10320
ggatatgcat ccgctggatt tcagtctgct gaaccggcgc gaggctgacg aagagcctga 10380
agatgatgtg ctgatgcaga aagcggcagg gcttgccgga ggtgtccgct ttggcccgga 10440
cgggaatgaa gttatccccg cttccccgga tgtggcggac atgacggagg atgacgtaat 10500
gctgatgaca gtatcagaag ggatcgcagg aggagtccgg tatggctgaa ccggtaggcg 10560
atctggtcgt tgatttgagt ctggatgcgg ccagatttga cgagcagatg gccagagtca 10620
ggcgtcattt ttctggtacg gaaagtgatg cgaaaaaaac agcggcagtc gttgaacagt 10680
cgctgagccg acaggcgctg gctgcacaga aagcggggat ttccgtcggg cagtataaag 10740
ccgccatgcg tatgctgcct gcacagttca ccgacgtggc cacgcagctt gcaggcgggc 10800
aaagtccgtg gctgatcctg ctgcaacagg gggggcaggt gaaggactcc ttcggcggga 10860
tgatccccat gttcaggggg cttgccggtg cgatcaccct gccgatggtg ggggccacct 10920
cgctggcggt ggcgaccggt gcgctggcgt atgcctggta tcagggcaac tcaaccctgt 10980
ccgatttcaa caaaacgctg gtcctttccg gcaatcaggc gggactgacg gcagatcgta 11040
tgctggtcct gtccagagcc gggcaggcgg cagggctgac gtttaaccag accagcgagt 11100
cactcagcgc actggttaag gcgggggtaa gcggtgaggc tcagattgcg tccatcagcc 11160
agagtgtggc gcgtttctcc tctgcatccg gcgtggaggt ggacaaggtc gctgaagcct 11220
tcgggaagct gaccacagac ccgacgtcgg ggctgacggc gatggctcgc cagttccata 11280
acgtgtcggc ggagcagatt gcgtatgttg ctcagttgca gcgttccggc gatgaagccg 11340
gggcattgca ggcggcgaac gaggccgcaa cgaaagggtt tgatgaccag acccgccgcc 11400
tgaaagagaa catgggcacg ctggagacct gggcagacag gactgcgcgg gcattcaaat 11460
ccatgtggga tgcggtgctg gatattggtc gtcctgatac cgcgcaggag atgctgatta 11520
aggcagaggc tgcgtataag aaagcagacg acatctggaa tctgcgcaag gatgattatt 11580
ttgttaacga tgaagcgcgg gcgcgttact gggatgatcg tgaaaaggcc cgtcttgcgc 11640
ttgaagccgc ccgaaagaag gctgagcagc agactcaaca ggacaaaaat gcgcagcagc 11700
agagcgatac cgaagcgtca cggctgaaat ataccgaaga ggcgcagaag gcttacgaac 11760
ggctgcagac gccgctggag aaatataccg cccgtcagga agaactgaac aaggcactga 11820
aagacgggaa aatcctgcag gcggattaca acacgctgat ggcggcggcg aaaaaggatt 11880
atgaagcgac gctgaaaaag ccgaaacagt ccagcgtgaa ggtgtctgcg ggcgatcgtc 11940
aggaagacag tgctcatgct gccctgctga cgcttcaggc agaactccgg acgctggaga 12000
agcatgccgg agcaaatgag aaaatcagcc agcagcgccg ggatttgtgg aaggcggaga 12060
gtcagttcgc ggtactggag gaggcggcgc aacgtcgcca gctgtctgca caggagaaat 12120
ccctgctggc gcataaagat gagacgctgg agtacaaacg ccagctggct gcacttggcg 12180
acaaggttac gtatcaggag cgcctgaacg cgctggcgca gcaggcggat aaattcgcac 12240
agcagcaacg ggcaaaacgg gccgccattg atgcgaaaag ccgggggctg actgaccggc 12300
aggcagaacg ggaagccacg gaacagcgcc tgaaggaaca gtatggcgat aatccgctgg 12360
cgctgaataa cgtcatgtca gagcagaaaa agacctgggc ggctgaagac cagcttcgcg 12420
ggaactggat ggcaggcctg aagtccggct ggagtgagtg ggaagagagc gccacggaca 12480
gtatgtcgca ggtaaaaagt gcagccacgc agacctttga tggtattgca cagaatatgg 12540
cggcgatgct gaccggcagt gagcagaact ggcgcagctt cacccgttcc gtgctgtcca 12600

```
tgatgacaga aattctgctt aagcaggcaa tggtggggat tgtcgggagt atcggcagcg  12660
ccattggcgg ggctgttggt ggcggcgcat ccgcgtcagg cggtacagcc attcaggccg  12720
ctgcggcgaa attccatttt gcaaccggag gatttacggg aaccggcggc aaatatgagc  12780
cagcggggat tgttcaccgt ggtgagtttg tcttcacgaa ggaggcaacc agccggattg  12840
gcgtggggaa tctttaccgg ctgatgcgcg gctatgccac cggcggttat gtcggtacac  12900
cgggcagcat ggcagacagc cggtcgcagg cgtccgggac gtttgagcag aataaccatg  12960
tggtgattaa caacgacggc acgaacgggc agataggtcc ggctgctctg aaggcggtgt  13020
atgacatggc ccgcaagggt gcccgtgatg aaattcagac acagatgcgt gatggtggcc  13080
tgttctccgg aggtggacga tgaagacctt ccgctggaaa gtgaaacccg gtatggatgt  13140
ggcttcggtc ccttctgtaa gaaaggtgcg ctttggtgat ggctattctc agcgagcgcc  13200
tgccgggctg aatgccaacc tgaaaacgta cagcgtgacg ctttctgtcc cccgtgagga  13260
ggccacggta ctggagtcgt ttctggaaga gcacgggggc tggaaatcct ttctgtggac  13320
gccgccttat gagtggcggc agataaaggt gacctgcgca aaatggtcgt cgcgggtcag  13380
tatgctgcgt gttgagttca gcgcagagtt tgaacaggtg gtgaactgat gcaggatatc  13440
cggcaggaaa cactgaatga atgcacccgt gcggagcagt cggccagcgt ggtgctctgg  13500
gaaatcgacc tgacagaggt cggtggagaa cgttattttt tctgtaatga gcagaacgaa  13560
aaaggtgagc cggtcacctg gcaggggcga cagtatcagc cgtatcccat tcaggggagc  13620
ggttttgaac tgaatggcaa aggcaccagt acgcgcccca cgctgacggt ttctaacctg  13680
tacggtatgg tcaccgggat ggcggaagat atgcagagtc tggtcggcgg aacggtggtc  13740
cggcgtaagg tttacgcccg ttttctggat gcggtgaact tcgtcaacgg aaacagttac  13800
gccgatccgg agcaggaggt gatcagccgc tggcgcattg agcagtgcag cgaactgagc  13860
gcggtgagtg cctcctttgt actgtccacg ccgacggaaa cggatggcgc tgtttttccg  13920
ggacgtatca tgctggccaa cacctgcacc tggacctatc gcggtgacga gtgcggttat  13980
agcggtccgg ctgtcgcgga tgaatatgac cagccaacgt ccgatatcac gaaggataaa  14040
tgcagcaaat gcctgagcgg ttgtaagttc cgcaataacg tcggcaactt tggcggcttc  14100
ctttccatta acaaactttc gcagtaaatc ccatgacaca gacagaatca gcgattctgg  14160
cgcacgcccg gcgatgtgcg ccagcggagt cgtgcggctt cgtggtaagc acgccggagg  14220
gggaaagata tttcccctgc gtgaatatct ccggtgagcc ggaggctatt tccgtatgtc  14280
gccggaagac tggctgcagg cagaaatgca gggtgagatt gtggcgctgg tccacagcca  14340
ccccggtggt ctgccctggc tgagtgaggc cgaccggcgg ctgcaggtgc agagtgattt  14400
gccgtggtgg ctggtctgcc gggggacgat tcataagttc cgctgtgtgc cgcatctcac  14460
cgggcggcgc tttgagcacg gtgtgacgga ctgttacaca ctgttccggg atgcttatca  14520
tctggcgggg attgagatgc cggactttca tcgtgaggat gactggtggc gtaacggcca  14580
gaatctctat ctggataatc tggaggcgac ggggctgtat caggtgccgt tgtcagcggc  14640
acagccgggc gatgtgctgc tgtgctgttt tggttcatca gtgccgaatc acgccgcaat  14700
ttactgcggc gacggcgagc tgctgcacca tattcctgaa caactgagca aacgagagag  14760
gtacaccgac aaatggcagc gacgcacaca ctccctctgg cgtcaccggg catggcgcgc  14820
atctgccttt acggggattt acaacgattt ggtcgccgca tcgaccttcg tgtgaaaacg  14880
ggggctgaag ccatccgggc actggccaca cagctcccgg cgtttcgtca gaaactgagc  14940
```

gacggctggt atcaggtacg gattgccggg cgggacgtca gcacgtccgg gttaacggcg 15000
cagttacatg agactctgcc tgatggcgct gtaattcata ttgttcccag agtcgccggg 15060
gccaagtcag gtggcgtatt ccagattgtc ctgggggctg ccgccattgc cggatcattc 15120
tttaccgccg gagccaccct tgcagcatgg ggggcagcca ttggggccgg tggtatgacc 15180
ggcatcctgt tttctctcgg tgccagtatg gtgctcggtg gtgtggcgca gatgctggca 15240
ccgaaagcca gaactccccg tatacagaca acggataacg gtaagcagaa cacctatttc 15300
tcctcactgg ataacatggt tgcccagggc aatgttctgc ctgttctgta cggggaaatg 15360
cgcgtggggt cacgcgtggt ttctcaggag atcagcacgg cagacgaagg ggacggtggt 15420
caggttgtgg tgattggtcg ctgatgcaaa atgttttatg tgaaaccgcc tgcgggcggt 15480
tttgtcattt atggagcgtg aggaatgggt aaaggaagca gtaaggggca taccccgcgc 15540
gaagcgaagg acaacctgaa gtccacgcag ttgctgagtg tgatcgatgc catcagcgaa 15600
gggccgattg aaggtccggt ggatggctta aaaagcgtgc tgctgaacag tacgccggtg 15660
ctggacactg aggggaatac caacatatcc ggtgtcacgg tggtgttccg ggctggtgag 15720
caggagcaga ctccgccgga gggatttgaa tcctccggct ccgagacggt gctgggtacg 15780
gaagtgaaat atgacacgcc gatcacccgc accattacgt ctgcaaacat cgaccgtctg 15840
cgctttacct tcggtgtaca ggcactggtg gaaaccacct caaagggtga caggaatccg 15900
tcggaagtcc gcctgctggt tcagatacaa cgtaacggtg gctgggtgac ggaaaaagac 15960
atcaccatta agggcaaaac cacctcgcag tatctggcct cggtggtgat gggtaacctg 16020
ccgccgcgcc cgtttaatat ccggatgcgc aggatgacgc cggacagcac cacagaccag 16080
ctgcagaaca aaacgctctg gtcgtcatac actgaaatca tcgatgtgaa acagtgctac 16140
ccgaacacgg cactggtcgg cgtgcaggtg gactcggagc agttcggcag ccagcaggtg 16200
agccgtaatt atcatctgcg cgggcgtatt ctgcaggtgc cgtcgaacta taacccgcag 16260
acgcggcaat acagcggtat ctgggacgga acgtttaaac cggcatacag caacaacatg 16320
gcctggtgtc tgtgggatat gctgacccat ccgcgctacg gcatggggaa acgtcttggt 16380
gcggcggatg tggataaatg ggcgctgtat gtcatcggcc agtactgcga ccagtcagtg 16440
ccggacggct ttggcggcac ggagccgcgc atcacctgta atgcgtacct gaccacacag 16500
cgtaaggcgt gggatgtgct cagcgatttc tgctcggcga tgcgctgtat gccggtatgg 16560
aacgggcaga cgctgacgtt cgtgcaggac cgaccgtcgg ataagacgtg gacctataac 16620
cgcagtaatg tggtgatgcc ggatgatggc gcgccgttcc gctacagctt cagcgccctg 16680
aaggaccgcc ataatgccgt tgaggtgaac tggattgacc cgaacaacgg ctgggagacg 16740
gcgacagagc ttgttgaaga tacgcaggcc attgcccgtt acggtcgtaa tgttacgaag 16800
atggatgcct ttggctgtac cagccggggg caggcacacc gcgccgggct gtggctgatt 16860
aaaacagaac tgctggaaac gcagaccgtg gatttcagcg tcggcgcaga agggcttcgc 16920
catgtaccgg gcgatgttat tgaaatctgc gatgatgact atgccggtat cagcaccggt 16980
ggtcgtgtgc tggcggtgaa cagccagacc cggacgctga cgctcgaccg tgaaatcacg 17040
ctgccatcct ccggtaccgc gctgataagc ctggttgacg gaagtggcaa tccggtcagc 17100
gtggaggttc agtccgtcac cgacggcgtg aaggtaaaag tgagccgtgt tcctgacggt 17160
gttgctgaat acagcgtatg ggagctgaag ctgccgacgc tgcgccagcg actgttccgc 17220
tgcgtgagta tccgtgagaa cgacgacggc acgtatgcca tcaccgccgt gcagcatgtg 17280
ccggaaaaag aggccatcgt ggataacggg gcgcactttg acggcgaaca gagtggcacg 17340
gtgaatggtg tcacgccgcc agcggtgcag cacctgaccg cagaagtcac tgcagacagc 17400
ggggaatatc aggtgctggc gcgatgggac acaccgaagg tggtgaaggg cgtgagtttc 17460
ctgctccgtc tgaccgtaac agcggacgac ggcagtgagc ggctggtcag cacggcccgg 17520
acgacggaaa ccacataccg cttcacgcaa ctggcgctgg ggaactacag gctgacagtc 17580
cgggcggtaa atgcgtgggg gcagcagggc gatccggcgt cggtatcgtt ccggattgcc 17640
gcaccggcag caccgtcgag gattgagctg acgccgggct attttcagat aaccgccacg 17700
ccgcatcttg ccgtttatga cccgacggta cagtttgagt tctggttctc ggaaaagcag 17760
attgcggata tcagacaggt tgaaaccagc acgcgttatc ttggtacggc gctgtactgg 17820
atagccgcca gtatcaatat caaaccgggc catgattatt acttttatat ccgcagtgtg 17880
aacaccgttg gcaaatcggc attcgtggag gccgtcggtc gggcgagcga tgatgcggaa 17940
ggttacctgg atttttcaa aggcaagata accgaatccc atctcggcaa ggagctgctg 18000
gaaaaagtcg agctgacgga ggataacgcc agcagactgg aggagttttc gaaagagtgg 18060
aaggatgcca gtgataagtg gaatgccatg tgggctgtca aaattgagca gaccaaagac 18120
ggcaaacatt atgtcgcggg tattggcctc agcatggagg acacggagga aggcaaactg 18180
agccagtttc tggttgccgc caatcgtatc gcatttattg acccggcaaa cgggaatgaa 18240
acgccgatgt ttgtggcgca gggcaaccag atattcatga acgacgtgtt cctgaagcgc 18300
ctgacggccc ccaccattac cagcggcggc aatcctccgg ccttttccct gacaccggac 18360
ggaaagctga ccgctaaaaa tgcggatatc agtggcagtg tgaatgcgaa ctccgggacg 18420
ctcagtaatg tgacgatagc tgaaaactgt acgataaacg gtacgctgag ggcggaaaaa 18480
atcgtcgggg acattgtaaa ggcggcgagc gcggcttttc cgcgccagcg tgaaagcagt 18540
gtggactggc cgtcaggtac ccgtactgtc accgtgaccg atgaccatcc ttttgatcgc 18600
cagatagtgg tgcttccgct gacgtttcgc ggaagtaagc gtactgtcag cggcaggaca 18660
acgtattcga tgtgttatct gaaagtactg atgaacggtg cggtgattta tgatggcgcg 18720
gcgaacgagg cggtacaggt gttctcccgt attgttgaca tgccagcggg tcggggaaac 18780
gtgatcctga cgttcacgct tacgtccaca cggcattcgg cagatattcc gccgtatacg 18840
tttgccagcg atgtgcaggt tatggtgatt aagaaacagg cgctgggcat cagcgtggtc 18900
tgagtgtgtt acagaggttc gtccgggaac gggcgtttta ttataaaaca gtgagaggtg 18960
aacgatgcgt aatgtgtgta ttgccgttgc tgtctttgcc gcacttgcgg tgacagtcac 19020
tccggcccgt gcggaaggtg gacatggtac gtttacggtg ggctattttc aagtgaaacc 19080
gggtacattg ccgtcgttgt cgggcgggga taccggtgtg agtcatctga aagggattaa 19140
cgtgaagtac cgttatgagc tgacggacag tgtgggggtg atggcttccc tggggttcgc 19200
cgcgtcgaaa aagagcagca cagtgatgac cggggaggat acgtttcact atgagagcct 19260
gcgtggacgt tatgtgagcg tgatggccgg accggtttta caaatcagta agcaggtcag 19320
tgcgtacgcc atggccggag tggctcacag tcggtggtcc ggcagtacaa tggattaccg 19380
taagacggaa atcactcccg ggtatatgaa agagacgacc actgccaggg acgaaagtgc 19440
aatgcggcat acctcagtgg cgtggagtgc aggtatacag attaatccgg cagcgtccgt 19500
cgttgttgat attgcttatg aaggctccgg cagtggcgac tggcgtactg acggattcat 19560
cgttggggtc ggttataaat tctgattagc caggtaacac agtgttatga cagcccgccg 19620
gaaccggtgg gctttttgt ggggtgaata tggcagtaaa gatttcagga gtcctgaaag 19680

-continued acggcacagg aaaaccggta cagaactgca ccattcagct gaaagccaga cgtaacagca 19740
ccacggtggt ggtgaacacg gtgggctcag agaatccgga tgaagccggg cgttacagca 19800
tggatgtgga gtacggtcag tacagtgtca tcctgcaggt tgacggtttt ccaccatcgc 19860
acgccgggac catcaccgtg tatgaagatt cacaaccggg gacgctgaat gattttctct 19920
gtgccatgac ggaggatgat gcccggccgg aggtgctgcg tcgtcttgaa ctgatggtgg 19980
aagaggtggc gcgtaacgcg tccgtggtgg cacagagtac ggcagacgcg aagaaatcag 20040
ccggcgatgc cagtgcatca gctgctcagg tcgcggccct tgtgactgat gcaactgact 20100
cagcacgcgc cgccagcacg tccgccggac aggctgcatc gtcagctcag gaagcgtcct 20160
ccggcgcaga agcggcatca gcaaaggcca ctgaagcgga aaaaagtgcc gcagccgcag 20220
agtcctcaaa aaacgcggcg gccaccagtg ccggtgcggc gaaaacgtca gaaacgaatg 20280
ctgcagcgtc acaacaatca gccgccacgt ctgcctccac cgcggccacg aaagcgtcag 20340
aggccgccac ttcagcacga gatgcggtgg cctcaaaaga ggcagcaaaa tcatcagaaa 20400
cgaacgcatc atcaagtgcc ggtcgtgcag cttcctcggc aacggcggca gaaaattctg 20460
ccagggcggc aaaaacgtcc gagacgaatg ccaggtcatc tgaaacagca gcggaacgga 20520
gcgcctctgc cgcggcagac gcaaaaacag cggcggcggg gagtgcgtca acggcatcca 20580
cgaaggcgac agaggctgcg ggaagtgcgg tatcagcatc gcagagcaaa agtgcggcag 20640
aagcggcggc aatacgtgca aaaaattcgg caaaaacgtgc agaagatata gcttcagctg 20700
tcgcgcttga ggatgcggac acaacgagaa aggggatagt gcagctcagc agtgcaacca 20760
acagcacgtc tgaaacgctt gctgcaacgc caaaggcggt taaggtggta atggatgaaa 20820
cgaacagaaa agcccactgg acagtccggc actgaccgga acgccaacag caccaaccgc 20880
gctcagggga acaaacaata cccagattgc gaacaccgct tttgtactgg ccgcgattgc 20940
agatgttatc gacgcgtcac ctgacgcact gaatacgctg aatgaactgg ccgcagcgct 21000
cgggaatgat ccagattttg ctaccaccat gactaacgcg cttgcgggta aacaaccgaa 21060
gaatgcgaca ctgacggcgc tggcagggct ttccacggcg aaaaataaat taccgtattt 21120
tgcggaaaat gatgccgcca gcctgactga actgactcag gttggcaggg atattctggc 21180
aaaaaattcc gttgcagatg ttcttgaata ccttggggcc ggtgagaatt cggcctttcc 21240
ggcaggtgcg ccgatcccgt ggccatcaga tatcgttccg tctggctacg tcctgatgca 21300
ggggcaggcg tttgacaaat cagcctaccc aaaacttgct gtcgcgtatc catcgggtgt 21360
gcttcctgat atgcgaggct ggacaatcaa ggggaaaccc gccagcggtc gtgctgtatt 21420
gtctcaggaa caggatggaa ttaagtcgca cacccacagt gccagtgcat ccggtacgga 21480
tttggggacg aaaaccacat cgtcgtttga ttacgggacg aaaacaacag gcagtttcga 21540
ttacggcacc aaatcgacga ataacacggg ggctcatgct cacagtctga gcggttcaac 21600
aggggccgcg ggtgctcatg cccacacaag tggtttaagg atgaacagtt ctggctggag 21660
tcagtatgga acagcaacca ttacaggaag tttatccaca gttaaaggaa ccagcacaca 21720
gggtattgct tatttatcga aaacggacag tcagggcagc cacagtcact cattgtccgg 21780
tacagccgtg agtgccggtg cacatgcgca tacagttggt attggtgcgc accagcatcc 21840
ggttgttatc ggtgctcatg cccattcttt cagtattggt tcacacggac acaccatcac 21900
cgttaacgct gcgggtaacg cggaaaacac cgtcaaaaac attgcattta actatattgt 21960
gaggcttgca taatggcatt cagaatgagt gaacaaccac ggaccataaa aatttataat 22020
ctgctggccg gaactaatga atttattggt gaaggtgacg catatattcc gcctcatacc 22080
ggtctgcctg caaacagtac cgatattgca ccgccagata ttccggctgg ctttgtggct 22140
gttttcaaca gtgatgaggc atcgtggcat ctcgttgaag accatcgggg taaaaccgtc 22200
tatgacgtgg cttccggcga cgcgttattt atttctgaac tcggtccgtt accggaaaat 22260
tttacctggt tatcgccggg aggggaatat cagaagtgga acggcacagc ctgggtgaag 22320
gatacggaag cagaaaaact gttccggatc cgggaggcgg aagaaacaaa aaaaagcctg 22380
atgcaggtag ccagtgagca tattgcgccg cttcaggatg ctgcagatct ggaaattgca 22440
acgaaggaag aaacctcgtt gctggaagcc tggaagaagt atcgggtgtt gctgaaccgt 22500
gttgatacat caactgcacc tgatattgag tggcctgctg tccctgttat ggagtaatcg 22560
ttttgtgata tgccgcagaa acgttgtatg aaataacgtt ctgcggttag ttagtatatt 22620
gtaaagctga gtattggttt atttggcgat tattatcttc aggagaataa tggaagttct 22680
atgactcaat tgttcatagt gtttacatca ccgccaattg cttttaagac tgaacgcatg 22740
aaatatggtt tttcgtcatg ttttgagtct gctgttgata tttctaaagt cggttttttt 22800
tcttcgtttt ctctaactat tttccatgaa atacattttt gattattatt tgaatcaatt 22860
ccaattacct gaagtctttc atctataatt ggcattgtat gtattggttt attggagtag 22920
atgcttgctt ttctgagcca tagctctgat atccaaatga agccataggc atttgttatt 22980
ttggctctgt cagctgcata acgccaaaaa atatatttat ctgcttgatc ttcaaatgtt 23040
gtattgatta aatcaattgg atggaattgt ttatcataaa aaattaatgt ttgaatgtga 23100
taaccgtcct ttaaaaaagt cgtttctgca agcttggctg tatagtcaac taactcttct 23160
gtcgaagtga tatttttagg cttatctacc agttttagac gctctttaat atcttcagga 23220
attattttat tgtcatattg tatcatgcta aatgacaatt tgcttatgga gtaatctttt 23280
aattttaaat aagttattct cctggcttca tcaaataaag agtcgaatga tgttggcgaa 23340
atcacatcgt cacccattgg attgtttatt tgtatgccaa gagagttaca gcagttatac 23400
attctgccat agattatagc taaggcatgt aataattcgt aatcttttag cgtattagcg 23460
acccatcgtc tttctgattt aataatagat gattcagtta aatatgaagg taatttcttt 23520
tgtgcaagtc tgactaactt ttttatacca atgtttaaca tactttcatt tgtaataaac 23580
tcaatgtcat tttcttcaat gtaagatgaa ataagagtag cctttgcctc gctatacatt 23640
tctaaatcgc cttgttttc tatcgtattg cgagaatttt tagcccaagc cattaatgga 23700
tcatttttcc atttttcaat aacattattg ttataccaaa tgtcatatcc tataatctgg 23760
tttttgtttt tttgaataat aaatgttact gttcttgcgg tttggaggaa ttgattcaaa 23820
ttcaagcgaa ataattcagg gtcaaaatat gtatcaatgc agcatttgag caagtgcgat 23880
aaatctttaa gtcttctttc ccatggtttt ttagtcataa aactctccat tttgataggt 23940
tgcatgctag atgctgatat attttagagg tgataaaatt aactgcttaa ctgtcaatgt 24000
aatacaagtt gtttgatctt tgcaatgatt cttatcagaa accatatagt aaattagtta 24060
cacaggaaat ttttaatatt attattatca ttcattatgt attaaaatta gagttgtggc 24120
ttggctctgc taacacgttg ctcataggag atatggtaga gccgcagaca cgtcgtatgc 24180
aggaacgtgc tgcggctggc tggtgaactt ccgatagtgc gggtgttgaa tgatttccag 24240
ttgctaccga ttttacatat tttttgcatg agagaatttg taccacctcc caccgaccat 24300
ctatgactgt acgccactgt ccctaggact gctatgtgcc ggagcggaca ttacaaacgt 24360
ccttctcggt gcatgccact gttgccaatg acctgcctag gaattggtta gcaagttact 24420

-continued

```
accggatttt gtaaaaacag ccctcctcat ataaaaagta ttcgttcact tccgataagc  24480
gtcgtaattt tctatctttc atcatattct agatccctct gaaaaaatct tccgagtttg  24540
ctaggcactg atacataact cttttccaat aattggggaa gtcattcaaa tctataatag  24600
gtttcagatt tgcttcaata aattctgact gtagctgctg aaacgttgcg gttgaactat  24660
atttccttat aacttttacg aaagagtttc tttgagtaat cacttcactc aagtgcttcc  24720
ctgcctccaa acgatacctg ttagcaatat ttaatagctt gaaatgatga agagctctgt  24780
gtttgtcttc ctgcctccag ttcgccgggc attcaacata aaaactgata gcacccggag  24840
ttccggaaac gaaatttgca tatacccatt gctcacgaaa aaaaatgtcc ttgtcgatat  24900
agggatgaat cgcttggtgt acctcatcta ctgcgaaaac ttgacctttc tctcccatat  24960
tgcagtcgcg gcacgatgga actaaattaa taggcatcac cgaaaattca ggataatgtg  25020
caataggaag aaaatgatct atatttttg tctgtcctat atcaccacaa aatggacatt  25080
tttcacctga tgaaacaagc atgtcatcgt aatatgttct agcgggtttg tttttatctc  25140
ggagattatt ttcataaagc ttttctaatt taacctttgt caggttacca actactaagg  25200
ttgtaggctc aagagggtgt gtcctgtcgt aggtaaataa ctgacctgtc gagcttaata  25260
ttctatattg ttgttctttc tgcaaaaaag tggggaagtg agtaatgaaa ttatttctaa  25320
catttatctg catcatacct tccgagcatt tattaagcat ttcgctataa gttctcgctg  25380
gaagaggtag ttttttcatt gtactttacc ttcatctctg ttcattatca tcgcttttaa  25440
aacggttcga ccttctaatc ctatctgacc attataattt tttagaatgg tttcataaga  25500
aagctctgaa tcaacggact gcgataataa gtggtggtat ccagaatttg tcacttcaag  25560
taaaaacacc tcacgagtta aaacacctaa gttctcaccg aatgtctcaa tatccggacg  25620
gataatattt attgcttctc ttgaccgtag gactttccac atgcaggatt ttggaacctc  25680
ttgcagtact actggggaat gagttgcaat tattgctaca ccattgcgtg catcgagtaa  25740
gtcgcttaat gttcgtaaaa aagcagagag caaaggtgga tgcagatgaa cctctggttc  25800
atcgaataaa actaatgact tttcgccaac gacatctact aatcttgtga tagtaaataa  25860
aacaattgca tgtccagagc tcattcgaag cagatatttc tggatattgt cataaaacaa  25920
tttagtgaat ttatcatcgt ccacttgaat ctgtggttca ttacgtctta actcttcata  25980
tttagaaatg aggctgatga gttccatatt tgaaaagttt tcatcactac ttagtttttt  26040
gatagcttca agccagagtt gtctttttct atctactctc atacaaccaa taaatgctga  26100
aatgaattct aagcggagat cgcctagtga ttttaaacta ttgctggcag cattcttgag  26160
tccaatataa aagtattgtg taccttttgc tgggtcaggt tgttctttag gaggagtaaa  26220
aggatcaaat gcactaaacg aaactgaaac aagcgatcga aaatatccct ttgggattct  26280
tgactcgata agtctattat tttcagagaa aaaatattca ttgttttctg ggttggtgat  26340
tgcaccaatc attccattca aaattgttgt tttaccacac ccattccgcc cgataaaagc  26400
atgaatgttc gtgctgggca tagaattaac cgtcacctca aaaggtatag ttaaatcact  26460
gaatccggga gcactttttc tattaaatga aaagtggaaa tctgacaatt ctggcaaacc  26520
atttaacaca cgtgcgaact gtccatgaat ttctgaaaga gttacccctc taagtaatga  26580
ggtgttaagg acgctttcat tttcaatgtc ggctaatcga tttggccata ctactaaatc  26640
ctgaatagct ttaagaaggt tatgtttaaa accatcgctt aatttgctga gattaacata  26700
gtagtcaatg ctttcaccta aggaaaaaaa catttcaggg agttgactga attttttatc  26760
tattaatgaa taagtgctta cttcttcttt ttgacctaca aaaccaattt taacatttcc  26820
```

gatatcgcat ttttcaccat gctcatcaaa gacagtaaga taaaacattg taacaaagga 26880
atagtcattc caaccatctg ctcgtaggaa tgccttattt ttttctactg caggaatata 26940
cccgcctctt tcaataacac taaactccaa catatagtaa cccttaattt tattaaaata 27000
accgcaattt atttggcggc aacacaggat ctctctttta agttactctc tattacatac 27060
gttttccatc taaaaattag tagtattgaa cttaacgggg catcgtattg tagttttcca 27120
tatttagctt tctgcttcct tttggataac ccactgttat tcatgttgca tggtgcactg 27180
tttataccaa cgatatagtc tattaatgca tatatagtat cgccgaacga ttagctcttc 27240
aggcttctga agaagcgttt caagtactaa taagccgata gatagccacg gacttcgtag 27300
ccatttttca taagtgttaa cttccgctcc tcgctcataa cagacattca ctacagttat 27360
ggcggaaagg tatgcatgct gggtgtgggg aagtcgtgaa agaaaagaag tcagctgcgt 27420
cgtttgacat cactgctatc ttcttactgg ttatgcaggt cgtagtgggt ggcacacaaa 27480
gctttgcact ggattgcgag gctttgtgct tctctggagt gcgacaggtt tgatgacaaa 27540
aaattagcgc aagaagacaa aaatcacctt gcgctaatgc tctgttacag gtcactaata 27600
ccatctaagt agttgattca tagtgactgc atatgttgtg ttttacagta ttatgtagtc 27660
tgttttttat gcaaaatcta atttaatata ttgatattta tatcatttta cgtttctcgt 27720
tcagcttttt tatactaagt tggcattata aaaaagcatt gcttatcaat ttgttgcaac 27780
gaacaggtca ctatcagtca aaataaaatc attatttgat ttcaattttg tcccactccc 27840
tgcctctgtc atcacgatac tgtgatgcca tggtgtccga cttatgcccg agaagatgtt 27900
gagcaaactt atcgcttatc tgcttctcat agagtcttgc agacaaactg cgcaactcgt 27960
gaaaggtagg cggatcccct tcgaaggaaa gacctgatgc ttttcgtgcg cgcataaaat 28020
accttgatac tgtgccggat gaaagcggtt cgcgacgagt agatgcaatt atggtttctc 28080
cgccaagaat ctctttgcat ttatcaagtg tttccttcat tgatattccg agagcatcaa 28140
tatgcaatgc tgttgggatg gcaattttta cgcctgtttt gctttgctcg acataaagat 28200
atccatctac gatatcagac cacttcattt cgcataaatc accaactcgt tgcccggtaa 28260
caacagccag ttccattgca agtctgagcc aacatggtga tgattctgct gcttgataaa 28320
ttttcaggta ttcgtcagcc gtaagtcttg atctccttac ctctgatttt gctgcgcgag 28380
tggcagcgac atggtttgtt gttatatggc cttcagctat tgcctctcgg aatgcatcgc 28440
tcagtgttga tctgattaac ttggctgacg ccgccttgcc ctcgtctatg tatccattga 28500
gcattgccgc aatttctttt gtggtgatgt cttcaagtgg agcatcaggc agacccctcc 28560
ttattgcttt aattttgctc atgtaattta tgagtgtctt ctgcttgatt cctctgctgg 28620
ccaggatttt ttcgtagcga tcaagccatg aatgtaacgt aacggaatta tcactgttga 28680
ttctcgctgt cagaggcttg tgtttgtgtc ctgaaaataa ctcaatgttg gcctgtatag 28740
cttcagtgat tgcgattcgc ctgtctctgc ctaatccaaa ctctttaccc gtccttgggt 28800
ccctgtagca gtaatatcca ttgtttctta tataaaggtt agggggtaaa tcccggcgct 28860
catgacttcg ccttcttccc atttctgatc ctcttcaaaa ggccacctgt tactggtcga 28920
tttaagtcaa cctttaccgc tgattcgtgg aacagatact ctcttccatc cttaaccgga 28980
ggtgggaata tcctgcattc ccgaacccat cgacgaactg tttcaaggct tcttggacgt 29040
cgctggcgtg cgttccactc ctgaagtgtc aagtacatcg caaagtctcc gcaattacac 29100
gcaagaaaaa accgccatca ggcggcttgg tgttctttca gttcttcaat tcgaatattg 29160

-continued

```
gttacgtctg catgtgctat ctgcgcccat atcatccagt ggtcgtagca gtcgttgatg  29220
ttctccgctt cgataactct gttgaatggc tctccattcc attctcctgt gactcggaag  29280
tgcatttatc atctccataa aacaaaaccc gccgtagcga gttcagataa aataaatccc  29340
cgcgagtgcg aggattgtta tgtaatattg ggtttaatca tctatatgtt ttgtacagag  29400
agggcaagta tcgtttccac cgtactcgtg ataataattt tgcacggtat cagtcatttc  29460
tcgcacattg cagaatgggg atttgtcttc attagactta taaaccttca tggaatattt  29520
gtatgccgac tctatatcta taccttcatc tacataaaca ccttcgtgat gtctgcatgg  29580
agacaagaca ccggatctgc acaacattga taacgcccaa tctttttgct cagactctaa  29640
ctcattgata ctcatttata aactccttgc aatgtatgtc gtttcagcta aacggtatca  29700
gcaatgttta tgtaaagaaa cagtaagata atactcaacc cgatgtttga gtacggtcat  29760
catctgacac tacagactct ggcatcgctg tgaagacgac gcgaaattca gcattttcac  29820
aagcgttatc ttttacaaaa ccgatctcac tctcctttga tgcgaatgcc agcgtcagac  29880
atcatatgca gatactcacc tgcatcctga acccattgac ctccaacccc gtaatagcga  29940
tgcgtaatga tgtcgatagt tactaacggg tcttgttcga ttaactgccg cagaaactct  30000
tccaggtcac cagtgcagtg cttgataaca ggagtcttcc caggatggcg aacaacaaga  30060
aactggtttc cgtcttcacg gacttcgttg ctttccagtt tagcaatacg cttactccca  30120
tccgagataa caccttcgta atactcacgc tgctcgttga gttttgattt tgctgtttca  30180
agctcaacac gcagtttccc tactgttagc gcaatatcct cgttctcctg gtcgcggcgt  30240
ttgatgtatt gctggtttct ttcccgttca tccagcagtt ccagcacaat cgatggtgtt  30300
accaattcat ggaaaaggtc tgcgtcaaat ccccagtcgt catgcattgc ctgctctgcc  30360
gcttcacgca gtgcctgaga gttaatttcg ctcacttcga acctctctgt ttactgataa  30420
gttccagatc ctcctggcaa cttgcacaag tccgacaacc ctgaacgacc aggcgtcttc  30480
gttcatctat cggatcgcca cactcacaac aatgagtggc agatatagcc tggtggttca  30540
ggcggcgcat tttattgct gtgttgcgct gtaattcttc tatttctgat gctgaatcaa  30600
tgatgtctgc catctttcat taatccctga actgttggtt aatacgcttg agggtgaatg  30660
cgaataataa aaaaggagcc tgtagctccc tgatgatttt gcttttcatg ttcatcgttc  30720
cttaaagacg ccgtttaaca tgccgattgc caggcttaaa tgagtcggtg tgaatcccat  30780
cagcgttacc gtttcgcggt gcttcttcag tacgctacgg caaatgtcat cgacgttttt  30840
atccggaaac tgctgtctgg ctttttttga tttcagaatt agcctgacgg gcaatgctgc  30900
gaagggcgtt ttcctgctga ggtgtcattg aacaagtccc atgtcggcaa gcataagcac  30960
acagaatatg aagcccgctg ccagaaaaat gcattccgtg gttgtcatac ctggtttctc  31020
tcatctgctt ctgctttcgc caccatcatt tccagctttt gtgaaaggga tgcggctaac  31080
gtatgaaatt cttcgtctgt ttctactggt attggcacaa acctgattcc aatttgagca  31140
aggctatgtg ccatctcgat actcgttctt aactcaacag aagatgcttt gtgcatacag  31200
cccctcgttt attatttatc tcctcagcca gccgctgtgc tttcagtgga tttcggataa  31260
cagaaaggcc gggaaatacc cagcctcgct ttgtaacgga gtagacgaaa gtgattgcgc  31320
ctacccggat attatcgtga ggatgcgtca tcgccattgc tccccaaata caaaaccaat  31380
ttcagccagt gcctcgtcca ttttttcgat gaactccggc acgatctcgt caaaactcgc  31440
catgtacttt tcatcccgct caatcacgac ataatgcagg ccttcacgct tcatacgcgg  31500
gtcatagttg gcaaagtacc aggcattttt tcgcgtcacc cacatgctgt actgcacctg  31560
```

ggccatgtaa gctgacttta tggcctcgaa accaccgagc cggaacttca tgaaatcccg 31620
ggaggtaaac gggcatttca gttcaaggcc gttgccgtca ctgcataaac catcgggaga 31680
gcaggcggta cgcatacttt cgtcgcgata gatgatcggg gattcagtaa cattcacgcc 31740
ggaagtgaat tcaaacaggg ttctggcgtc gttctcgtac tgttttcccc aggccagtgc 31800
tttagcgtta acttccggag ccacaccggt gcaaacctca gcaagcaggg tgtggaagta 31860
ggacattttc atgtcaggcc acttctttcc ggagcggggt tttgctatca cgttgtgaac 31920
ttctgaagcg gtgatgacgc cgagccgtaa tttgtgccac gcatcatccc cctgttcgac 31980
agctctcaca tcgatcccgg tacgctgcag gataatgtcc ggtgtcatgc tgccaccttc 32040
tgctctgcgg ctttctgttt caggaatcca agagctttta ctgcttcggc ctgtgtcagt 32100
tctgacgatg cacgaatgtc gcggcgaaat atctgggaac agagcggcaa taagtcgtca 32160
tcccatgttt tatccagggc gatcagcaga gtgttaatct cctgcatggt ttcatcgtta 32220
accggagtga tgtcgcgttc cggctgacgt tctgcagtgt atgcagtatt ttcgacaatg 32280
cgctcggctt catccttgtc atagatacca gcaaatccga aggccagacg ggcacactga 32340
atcatggctt tatgacgtaa catccgtttg ggatgcgact gccacggccc cgtgatttct 32400
ctgccttcgc gagttttgaa tggttcgcgg cggcattcat ccatccattc ggtaacgcag 32460
atcggatgat tacggtcctt gcggtaaatc cggcatgtac aggattcatt gtcctgctca 32520
aagtccatgc catcaaactg ctggttttca ttgatgatgc gggaccagcc atcaacgccc 32580
accaccggaa cgatgccatt ctgcttatca ggaaaggcgt aaatttcttt cgtccacgga 32640
ttaaggccgt actggttggc aacgatcagt aatgcgatga actgcgcatc gctggcatca 32700
cctttaaatg ccgtctggcg aagagtggtg atcagttcct gtgggtcgac agaatccatg 32760
ccgacacgtt cagccagctt cccagccagc gttgcgagtg cagtactcat tcgttttata 32820
cctctgaatc aatatcaacc tggtggtgag caatggtttc aaccatgtac cggatgtgtt 32880
ctgccatgcg ctcctgaaac tcaacatcgt catcaaacgc acgggtaatg gatttttttgc 32940
tggccccgtg gcgttgcaaa tgatcgatgc atagcgattc aaacaggtgc tggggcaggc 33000
ctttttccat gtcgtctgcc agttctgcct ctttctcttc acgggcgagc tgctggtagt 33060
gacgcgccca gctctgagcc tcaagacgat cctgaatgta ataagcgttc atggctgaac 33120
tcctgaaata gctgtgaaaa tatcgcccgc gaaatgccgg gctgattagg aaaacaggaa 33180
agggggttag tgaatgcttt tgcttgatct cagtttcagt attaatatcc atttttttata 33240
agcgtcgacg gcttcacgaa acatcttttc atcgccaata aaagtggcga tagtgaattt 33300
agtctggata gccataagtg tttgatccat tctttgggac tcctggctga ttaagtatgt 33360
cgataaggcg tttccatccg tcacgtaatt tacgggtgat tcgttcaagt aaagattcgg 33420
aagggcagcc agcaacaggc caccctgcaa tggcatattg catggtgtgc tccttattta 33480
tacataacga aaaacgcctc gagtgaagcg ttattggtat gcggtaaaac cgcactcagg 33540
cggccttgat agtcatatca tctgaatcaa atattcctga tgtatcgata tcggtaattc 33600
ttattccttc gctaccatcc attggaggcc atccttcctg accatttcca tcattccagt 33660
cgaactcaca cacaacacca tatgcattta agtcgcttga aattgctata agcagagcat 33720
gttgcgccag catgattaat acagcattta atacagagcc gtgtttattg agtcggtatt 33780
cagagtctga ccagaaatta ttaatctggt gaagtttttc ctctgtcatt acgtcatggt 33840
cgatttcaat ttctattgat gctttccagt cgtaatcaat gatgtatttt ttgatgtttg 33900
acatctgttc atatcctcac agataaaaaa tcgccctcac actggagggc aaagaagatt 33960
tccaataatc agaacaagtc ggctcctgtt tagttacgag cgacattgct ccgtgtattc 34020
actcgttgga atgaatacac agtgcagtgt ttattctgtt atttatgcca aaaataaagg 34080
ccactatcag gcagctttgt tgttctgttt accaagttct ctggcaatca ttgccgtcgt 34140
tcgtattgcc catttatcga catatttccc atcttccatt acaggaaaca tttcttcagg 34200
cttaaccatg cattccgatt gcagcttgca tccattgcat cgcttgaatt gtccacacca 34260
ttgattttta tcaatagtcg tagtcatacg gatagtcctg gtattgttcc atcacatcct 34320
gaggatgctc ttcgaactct tcaaattctt cttccatata tcaccttaaa tagtggattg 34380
cggtagtaaa gattgtgcct gtcttttaac cacatcaggc tcggtggttc tcgtgtaccc 34440
ctacagcgag aaatcggata aactattaca acccctacag tttgatgagt atagaaatgg 34500
atccactcgt tattctcgga cgagtgttca gtaatgaacc tctggagaga accatgtata 34560
tgatcgttat ctgggttgga cttctgcttt taagcccaga taactggcct gaatatgtta 34620
atgagagaat cggtattcct catgtgtggc atgttttcgt ctttgctctt gcattttcgc 34680
tagcaattaa tgtgcatcga ttatcagcta ttgccagcgc cagatataag cgatttaagc 34740
taagaaaacg cattaagatg caaaacgata aagtgcgatc agtaattcaa aaccttacag 34800
aagagcaatc tatggttttg tgcgcagccc ttaatgaagg caggaagtat gtggttacat 34860
caaaacaatt cccatacatt agtgagttga ttgagcttgg tgtgttgaac aaaacttttt 34920
cccgatggaa tggaaagcat atattattcc ctattgagga tatttactgg actgaattag 34980
ttgccagcta tgatccatat aatattgaga taaagccaag gccaatatct aagtaactag 35040
ataagaggaa tcgattttcc cttaattttc tggcgtccac tgcatgttat gccgcgttcg 35100
ccaggcttgc tgtaccatgt gcgctgattc ttgcgctcaa tacgttgcag gttgctttca 35160
atctgtttgt ggtattcagc cagcactgta aggtctatcg gatttagtgc gctttctact 35220
cgtgatttcg gtttgcgatt cagcgagaga atagggcggt taactggttt tgcgcttacc 35280
ccaaccaaca ggggatttgc tgctttccat tgagcctgtt tctctgcgcg acgttcgcgg 35340
cggcgtgttt gtgcatccat ctggattctc ctgtcagtta gctttggtgg tgtgtggcag 35400
ttgtagtcct gaacgaaaac cccccgcgat tggcacattg gcagctaatc cggaatcgca 35460
cttacggcca atgcttcgtt tcgtatcaca caccccaaag ccttctgctt tgaatgctgc 35520
ccttcttcag ggcttaattt ttaagagcgt caccttcatg gtggtcagtg cgtcctgctg 35580
atgtgctcag tatcaccgcc agtggtattt atgtcaacac cgccagagat aatttatcac 35640
cgcagatggt tatctgtatg tttttttatat gaatttattt tttgcagggg ggcattgttt 35700
ggtaggtgag agatctgaat tgctatgttt agtgagttgt atctatttat ttttcaataa 35760
atacaattgg ttatgtgttt tgggggcgat cgtgaggcaa agaaaacccg gcgctgaggc 35820
cgggttattc ttgttctctg gtcaaattat atagttggaa aacaaggatg catatatgaa 35880
tgaacgatgc agaggcaatg ccgatggcga tagtgggtat catgtagccg cttatgctgg 35940
aaagaagcaa taacccgcag aaaaacaaag ctccaagctc aacaaaacta agggcataga 36000
caataactac cgatgtcata tacccatact ctctaatctt ggccagtcgg cgcgttctgc 36060
ttccgattag aaacgtcaag gcagcaatca ggattgcaat catggttcct gcatatgatg 36120
acaatgtcgc cccaagacca tctctatgag ctgaaaaaga aacaccagga atgtagtggc 36180
ggaaaaggag atagcaaatg cttacgataa cgtaaggaat tattactatg taaacaccag 36240
gcatgattct gttccgcata attactcctg ataattaatc cttaactttg cccacctgcc 36300

```
ttttaaaaca ttccagtata tcacttttca ttcttgcgta gcaatatgcc atctcttcag  36360
ctatctcagc attggtgacc ttgttcagag gcgctgagag atggcctttt tctgatagat  36420
aatgttctgt taaaatatct ccggcctcat cttttgcccg caggctaatg tctgaaaatt  36480
gaggtgacgg gttaaaaata atatccttgg caaccttttt tatatccctt ttaaattttg  36540
gcttaatgac tatatccaat gagtcaaaaa gctccccttc aatatctgtt gcccctaaga  36600
cctttaatat atcgccaaat acaggtagct tggcttctac cttcaccgtt gttcggccga  36660
tgaaatgcat atgcataaca tcgtctttgg tggttcccct catcagtggc tctatctgaa  36720
cgcgctctcc actgcttaat gacattcctt tcccgattaa aaaatctgtc agatcggatg  36780
tggtcggccc gaaaacagtt ctggcaaaac caatggtgtc gccttcaaca aacaaaaaag  36840
atgggaatcc caatgattcg tcatctgcga ggctgttctt aatatcttca actgaagctt  36900
tagagcgatt tatcttctga accagactct tgtcatttgt tttggtaaag agaaaagttt  36960
ttccatcgat tttatgaata tacaaataat tggagccaac ctgcaggtga tgattatcag  37020
ccagcagaga attaaggaaa acagacaggt ttattgagcg cttatctttc cctttatttt  37080
tgctgcggta agtcgcataa aaaccattct tcataattca atccatttac tatgttatgt  37140
tctgagggga gtgaaaattc ccctaattcg atgaagattc ttgctcaatt gttatcagct  37200
atgcgccgac cagaacacct tgccgatcag ccaaacgtct cttcaggcca ctgactagcg  37260
ataactttcc ccacaacgga acaactctca ttgcatggga tcattgggta ctgtgggttt  37320
agtggttgta aaaacacctg accgctatcc ctgatcagtt tcttgaaggt aaactcatca  37380
cccccaagtc tggctatgca gaaatcacct ggctcaacag cctgctcagg gtcaacgaga  37440
attaacattc cgtcaggaaa gcttggcttg gagcctgttg gtgcggtcat ggaattacct  37500
tcaacctcaa gccagaatgc agaatcactg gctttttttgg ttgtgcttac ccatctctcc  37560
gcatcacctt tggtaaaggt tctaagctta ggtgagaaca tccctgcctg aacatgagaa  37620
aaaacagggt actcatactc acttctaagt gacggctgca tactaaccgc ttcatacatc  37680
tcgtagattt ctctggcgat tgaagggcta aattcttcaa cgctaacttt gagaattttt  37740
gtaagcaatg cggcgttata agcatttaat gcattgatgc cattaaataa agcaccaacg  37800
cctgactgcc ccatccccat cttgtctgcg acagattcct gggataagcc aagttcattt  37860
ttcttttttt cataaattgc tttaaggcga cgtgcgtcct caagctgctc ttgtgttaat  37920
ggtttctttt ttgtgctcat acgttaaatc tatcaccgca agggataaat atctaacacc  37980
gtgcgtgttg actattttac ctctggcggt gataatggtt gcatgtacta aggaggttgt  38040
atggaacaac gcataaccct gaaagattat gcaatgcgct ttgggcaaac caagacagct  38100
aaagatctcg gcgtatatca aagcgcgatc aacaaggcca ttcatgcagg ccgaaagatt  38160
tttttaacta taaacgctga tggaagcgtt tatgcggaag aggtaaagcc cttcccgagt  38220
aacaaaaaaa caacagcata aataaccccg ctcttacaca ttccagccct gaaaaagggc  38280
atcaaattaa accacaccta tggtgtatgc atttatttgc atacattcaa tcaattgtta  38340
tctaaggaaa tacttacata tggttcgtgc aaacaaacgc aacgaggctc tacgaatcga  38400
gagtgcgttg cttaacaaaa tcgcaatgct tggaactgag aagacagcgg aagctgtggg  38460
cgttgataag tcgcagatca gcaggtggaa gagggactgg attccaaagt tctcaatgct  38520
gcttgctgtt cttgaatggg gggtcgttga cgacgacatg gctcgattgg cgcgacaagt  38580
tgctgcgatt ctcaccaata aaaaacgccc ggcggcaacc gagcgttctg aacaaatcca  38640
```

-continued

```
gatggagttc tgaggtcatt actggatcta tcaacaggag tcattatgac aaatacagca  38700
aaaatactca acttcggcag aggtaacttt gccggacagg agcgtaatgt ggcagatctc  38760
gatgatggtt acgccagact atcaaatatg ctgcttgagg cttattcggg cgcagatctg  38820
accaagcgac agtttaaagt gctgcttgcc attctgcgta aaacctatgg gtggaataaa  38880
ccaatggaca gaatcaccga ttctcaactt agcgagatta caaagttacc tgtcaaacgg  38940
tgcaatgaag ccaagttaga actcgtcaga atgaatatta tcaagcagca aggcggcatg  39000
tttggaccaa ataaaaacat ctcagaatgg tgcatccctc aaaacgaggg aaaatcccct  39060
aaaacgaggg ataaaacatc cctcaaattg ggggattgct atccctcaaa acagggggac  39120
acaaaagaca ctattacaaa agaaaaaaga aaagattatt cgtcagagaa ttctggcgaa  39180
tcctctgacc agccagaaaa cgacctttct gtggtgaaac cggatgctgc aattcagagc  39240
ggcagcaagt gggggacagc agaagacctg accgccgcag agtggatgtt tgacatggtg  39300
aagactatcg caccatcagc cagaaaaccg aattttgctg ggtgggctaa cgatatccgc  39360
ctgatgcgtg aacgtgacgg acgtaaccac cgcgacatgt gtgtgctgtt ccgctgggca  39420
tgccaggaca acttctggtc cggtaacgtg ctgagcccgg ccaaactccg cgataagtgg  39480
acccaactcg aaatcaaccg taacaagcaa caggcaggcg tgacagccag caaaccaaaa  39540
ctcgacctga caaacacaga ctggatttac ggggtggatc tatgaaaaac atcgccgcac  39600
agatggttaa ctttgaccgt gagcagatgc gtcggatcgc caacaacatg ccggaacagt  39660
acgacgaaaa gccgcaggta cagcaggtag cgcagatcat caacggtgtg ttcagccagt  39720
tactggcaac tttcccggcg agcctggcta accgtgacca gaacgaagtg aacgaaatcc  39780
gtcgccagtg ggttctggct tttcgggaaa acgggatcac cacgatggaa caggttaacg  39840
caggaatgcg cgtagcccgt cggcagaatc gaccatttct gccatcaccc gggcagtttg  39900
ttgcatggtg ccgggaagaa gcatccgtta ccgccggact gccaaacgtc agcgagctgg  39960
ttgatatggt ttacgagtat tgccggaagc gaggcctgta tccggatgcg gagtcttatc  40020
cgtggaaatc aaacgcgcac tactggctgg ttaccaacct gtatcagaac atgcgggcca  40080
atgcgcttac tgatgcggaa ttacgccgta aggccgcaga tgagcttgtc catatgactg  40140
cgagaattaa ccgtggtgag gcgatccctg aaccagtaaa acaacttcct gtcatgggcg  40200
gtagacctct aaatcgtgca caggctctgg cgaagatcgc agaaatcaaa gctaagttcg  40260
gactgaaagg agcaagtgta tgacgggcaa agaggcaatt attcattacc tggggacgca  40320
taatagcttc tgtgcgccgg acgttgccgc gctaacaggc gcaacagtaa ccagcataaa  40380
tcaggccgcg gctaaaatgg cacgggcagg tcttctggtt atcgaaggta aggtctggcg  40440
aacggtgtat taccggtttg ctaccaggga agaacgggaa ggaaagatga gcacgaacct  40500
ggtttttaag gagtgtcgcc agagtgccgc gatgaaacgg gtattggcgg tatatggagt  40560
taaaagatga ccatctacat tactgagcta ataacaggcc tgctggtaat cgcaggcctt  40620
tttatttggg ggagagggaa gtcatgaaaa aactaacctt tgaaattcga tctccagcac  40680
atcagcaaaa cgctattcac gcagtacagc aaatccttcc agacccaacc aaaccaatcg  40740
tagtaaccat tcaggaacgc aaccgcagct tagaccaaaa caggaagcta tgggcctgct  40800
taggtgacgt ctctcgtcag gttgaatggc atggtcgctg gctggatgca gaaagctgga  40860
agtgtgtgtt taccgcagca ttaaagcagc aggatgttgt tcctaacctt gccgggaatg  40920
gctttgtggt aataggccag tcaaccagca ggatgcgtgt aggcgaattt gcggagctat  40980
tagagcttat acaggcattc ggtacagagc gtggcgttaa gtggtcagac gaagcgagac  41040
```

-continued

```
tggctctgga gtggaaagcg agatggggag acagggctgc atgataaatg tcgttagttt  41100
ctccggtggc aggacgtcag catatttgct ctggctaatg gagcaaaagc gacgggcagg  41160
taaagacgtg cattacgttt tcatggatac aggttgtgaa catccaatga catatcggtt  41220
tgtcagggaa gttgtgaagt tctgggatat accgctcacc gtattgcagg ttgatatcaa  41280
cccggagctt ggacagccaa atggttatac ggtatgggaa ccaaaggata ttcagacgcg  41340
aatgcctgtt ctgaagccat ttatcgatat ggtaaagaaa tatggcactc catacgtcgg  41400
cggcgcgttc tgcactgaca gattaaaact cgttcccttc accaaatact gtgatgacca  41460
tttcgggcga gggaattaca ccacgtggat tggcatcaga gctgatgaac cgaagcggct  41520
aaagccaaag cctggaatca gatatcttgc tgaactgtca gactttgaga aggaagatat  41580
cctcgcatgg tggaagcaac aaccattcga tttgcaaata ccggaacatc tcggtaactg  41640
catattctgc attaaaaaat caacgcaaaa aatcggactt gcctgcaaag atgaggaggg  41700
attgcagcgt gtttttaatg aggtcatcac gggatcccat gtgcgtgacg gacatcggga  41760
aacgccaaag gagattatgt accgaggaag aatgtcgctg gacggtatcg cgaaaatgta  41820
ttcagaaaat gattatcaag ccctgtatca ggacatggta cgagctaaaa gattcgatac  41880
cggctcttgt tctgagtcat gcgaaatatt tggagggcag cttgatttcg acttcgggag  41940
ggaagctgca tgatgcgatg ttatcggtgc ggtgaatgca aagaagataa ccgcttccga  42000
ccaaatcaac cttactggaa tcgatggtgt ctccggtgtg aaagaacacc aacaggggtg  42060
ttaccactac cgcaggaaaa ggaggacgtg tggcgagaca gcgacgaagt atcaccgaca  42120
taatctgcga aaactgcaaa taccttccaa cgaaacgcac cagaaataaa cccaagccaa  42180
tcccaaaaga atctgacgta aaaaccttca actacacggc tcacctgtgg gatatccggt  42240
ggctaagacg tcgtgcgagg aaaacaaggt gattgaccaa aatcgaagtt acgaacaaga  42300
aagcgtcgag cgagctttaa cgtgcgctaa ctgcggtcag aagctgcatg tgctggaagt  42360
tcacgtgtgt gagcactgct gcgcagaact gatgagcgat ccgaatagct cgatgcacga  42420
ggaagaagat gatggctaaa ccagcgcgaa gacgatgtaa aaacgatgaa tgccgggaat  42480
ggtttcaccc tgcattcgct aatcagtggt ggtgctctcc agagtgtgga accaagatag  42540
cactcgaacg acgaagtaaa gaacgcgaaa aagcggaaaa agcagcagag aagaaacgac  42600
gacgagagga gcagaaacag aaagataaac ttaagattcg aaaactcgcc ttaaagcccc  42660
gcagttactg gattaaacaa gcccaacaag ccgtaaacgc cttcatcaga gaaagagacc  42720
gcgacttacc atgtatctcg tgcggaacgc tcacgtctgc tcagtgggat gccggacatt  42780
accggacaac tgctgcggca cctcaactcc gatttaatga acgcaatatt cacaagcaat  42840
gcgtggtgtg caaccagcac aaaagcggaa atctcgttcc gtatcgcgtc gaactgatta  42900
gccgcatcgg gcaggaagca gtagacgaaa tcgaatcaaa ccataaccgc catcgctgga  42960
ctatcgaaga gtgcaaggcg atcaaggcag agtaccaaca gaaactcaaa gacctgcgaa  43020
atagcagaag tgaggccgca tgacgttctc agtaaaaacc attccagaca tgctcgttga  43080
aacatacgga aatcagacag aagtagcacg cagactgaaa tgtagtcgcg gtacggtcag  43140
aaaatacgtt gatgataaag acgggaaaat gcacgccatc gtcaacgacg ttctcatggt  43200
tcatcgcgga tggagtgaaa gagatgcgct attacgaaaa aattgatggc agcaaatacc  43260
gaaatatttg ggtagttggc gatctgcacg gatgctacac gaacctgatg aacaaactgg  43320
atacgattgg attcgacaac aaaaaagacc tgcttatctc ggtgggcgat ttggttgatc  43380
```

-continued

```
gtggtgcaga gaacgttgaa tgcctggaat taatcacatt cccctggttc agagctgtac  43440
gtggaaacca tgagcaaatg atgattgatg gcttatcaga gcgtggaaac gttaatcact  43500
ggctgcttaa tggcggtggc tggttcttta atctcgatta cgacaaagaa attctggcta  43560
aagctcttgc ccataaagca gatgaacttc cgttaatcat cgaactggtg agcaaagata  43620
aaaaatatgt tatctgccac gccgattatc cctttgacga atacgagttt ggaaagccag  43680
ttgatcatca gcaggtaatc tggaaccgcg aacgaatcag caactcacaa aacgggatcg  43740
tgaaagaaat caaaggcgcg gacacgttca tctttggtca tacgccagca gtgaaaccac  43800
tcaagtttgc caaccaaatg tatatcgata ccggcgcagt gttctgcgga aacctaacat  43860
tgattcaggt acagggagaa ggcgcatgag actcgaaagc gtagctaaat ttcattcgcc  43920
aaaaagcccg atgatgagcg actcaccacg ggccacggct tctgactctc tttccggtac  43980
tgatgtgatg gctgctatgg ggatggcgca atcacaagcc ggattcggta tggctgcatt  44040
ctgcggtaag cacgaactca gccagaacga caaacaaaag gctatcaact atctgatgca  44100
atttgcacac aaggtatcgg ggaaataccg tggtgtggca aagcttgaag gaaatactaa  44160
ggcaaaggta ctgcaagtgc tcgcaacatt cgcttatgcg gattattgcc gtagtgccgc  44220
gacgccgggg gcaagatgca gagattgcca tggtacaggc cgtgcggttg atattgccaa  44280
aacagagctg tgggggagag ttgtcgagaa agagtgcgga agatgcaaag gcgtcggcta  44340
ttcaaggatg ccagcaagcg cagcatatcg cgctgtgacg atgctaatcc caaaccttac  44400
ccaacccacc tggtcacgca ctgttaagcc gctgtatgac gctctggtgg tgcaatgcca  44460
caaagaagag tcaatcgcag acaacatttt gaatgcggtc acacgttagc agcatgattg  44520
ccacggatgg caacatatta acggcatgat attgacttat tgaataaaat tgggtaaatt  44580
tgactcaacg atgggttaat tcgctcgttg tggtagtgag atgaaaagag gcggcgctta  44640
ctaccgattc cgcctagttg gtcacttcga cgtatcgtct ggaactccaa ccatcgcagg  44700
cagagaggtc tgcaaaatgc aatcccgaaa cagttcgcag gtaatagtta gagcctgcat  44760
aacggtttcg ggattttta tatctgcaca acaggtaaga gcattgagtc gataatcgtg  44820
aagagtcggc gagcctggtt agccagtgct ctttccgttg tgctgaatta agcgaatacc  44880
ggaagcagaa ccggatcacc aaatgcgtac aggcgtcatc gccgcccagc aacagcacaa  44940
cccaaactga gccgtagcca ctgtctgtcc tgaattcatt agtaatagtt acgctgcggc  45000
cttttacaca tgaccttcgt gaaagcgggt ggcaggaggt cgcgctaaca acctcctgcc  45060
gttttgcccg tgcatatcgg tcacgaacaa atctgattac taaacacagt agcctggatt  45120
tgttctatca gtaatcgacc ttattcctaa ttaaatagag caaatcccct tattgggggt  45180
aagacatgaa gatgccagaa aaacatgacc tgttggccgc cattctcgcg gcaaaggaac  45240
aaggcatcgg ggcaatcctt gcgtttgcaa tggcgtacct tcgcggcaga tataatggcg  45300
gtgcgtttac aaaaacagta atcgacgcaa cgatgtgcgc cattatcgcc tagttcattc  45360
gtgaccttct cgacttcgcc ggactaagta gcaatctcgc ttatataacg agcgtgttta  45420
tcggctacat cggtactgac tcgattggtt cgcttatcaa acgcttcgct gctaaaaaag  45480
ccggagtaga agatggtaga aatcaataat caacgtaagg cgttcctcga tatgctggcg  45540
tggtcggagg gaactgataa cggacgtcag aaaaccagaa atcatggtta tgacgtcatt  45600
gtaggcggag agctatttac tgattactcc gatcaccctc gcaaacttgt cacgctaaac  45660
ccaaaactca aatcaacagg cgccggacgc taccagcttc tttcccgttg gtgggatgcc  45720
taccgcaagc agcttggcct gaaagacttc tctccgaaaa gtcaggacgc tgtggcattg  45780
```

-continued cagcagatta aggagcgtgg cgctttacct atgattgatc gtggtgatat ccgtcaggca 45840
atcgaccgtt gcagcaatat ctgggcttca ctgccgggcg ctggttatgg tcagttcgag 45900
cataaggctg acagcctgat tgcaaaattc aaagaagcgg gcggaacggt cagagagatt 45960
gatgtatgag cagagtcacc gcgattatct ccgctctggt tatctgcatc atcgtctgcc 46020
tgtcatgggc tgttaatcat taccgtgata acgccattac ctacaaagcc cagcgcgaca 46080
aaaatgccag agaactgaag ctggcgaacg cggcaattac tgacatgcag atgcgtcagc 46140
gtgatgttgc tgcgctcgat gcaaaataca cgaaggagtt agctgatgct aaagctgaaa 46200
atgatgctct gcgtgatgat gttgccgctg gtcgtcgtcg gttgcacatc aaagcagtct 46260
gtcagtcagt gcgtgaagcc accaccgcct ccggcgtgga taatgcagcc tccccccgac 46320
tggcagacac cgctgaacgg gattatttca ccctcagaga gaggctgatc actatgcaaa 46380
aacaactgga aggaacccag aagtatatta atgagcagtg cagatagagt tgcccatatc 46440
gatgggcaac tcatgcaatt attgtgagca atacacacgc gcttccagcg gagtataaat 46500
gcctaaagta ataaaaccga gcaatccatt tacgaatgtt tgctgggttt ctgttttaac 46560
aacattttct gcgccgccac aaattttggc tgcatcgaca gttttcttct gcccaattcc 46620
agaaacgaag aaatgatggg tgatggtttc ctttggtgct actgctgccg gtttgttttg 46680
aacagtaaac gtctgttgag cacatcctgt aataagcagg gccagcgcag tagcgagtag 46740
catttttttc atggtgttat tcccgatgct ttttgaagtt cgcagaatcg tatgtgtaga 46800
aaattaaaca aaccctaaac aatgagttga aatttcatat tgttaatatt tattaatgta 46860
tgtcaggtgc gatgaatcgt cattgtattc ccggattaac tatgtccaca gccctgacgg 46920
ggaacttctc tgcgggagtg tccgggaata attaaaacga tgcacacagg gtttagcgcg 46980
tacacgtatt gcattatgcc aacgccccgg tgctgacacg gaagaaaccg gacgttatga 47040
tttagcgtgg aaagatttgt gtagtgttct gaatgctctc agtaaatagt aatgaattat 47100
caaaggtata gtaatatctt ttatgttcat ggatatttgt aacccatcgg aaaactcctg 47160
ctttagcaag attttccctg tattgctgaa atgtgatttc tcttgatttc aacctatcat 47220
aggacgtttc tataagatgc gtgtttcttg agaatttaac atttacaacc tttttaagtc 47280
cttttattaa cacggtgtta tcgttttcta acacgatgtg aatattatct gtggctagat 47340
agtaaatata atgtgagacg ttgtgacgtt ttagttcaga ataaaacaat tcacagtcta 47400
aatcttttcg cacttgatcg aatatttctt taaaaatggc aacctgagcc attggtaaaa 47460
ccttccatgt gatacgaggg cgcgtagttt gcattatcgt ttttatcgtt tcaatctggt 47520
ctgacctcct tgtgttttgt tgatgattta tgtcaaatat taggaatgtt ttcacttaat 47580
agtattggtt gcgtaacaaa gtgcggtcct gctggcattc tggagggaaa tacaaccgac 47640
agatgtatgt aaggccaacg tgctcaaatc ttcatacaga aagatttgaa gtaatatttt 47700
aaccgctaga tgaagagcaa gcgcatggag cgacaaaatg aataaagaac aatctgctga 47760
tgatccctcc gtggatctga ttcgtgtaaa aaatatgctt aatagcacca tttctatgag 47820
ttaccctgat gttgtaattg catgtataga acataaggtg tctctggaag cattcagagc 47880
aattgaggca gcgttggtga agcacgataa taatatgaag gattattccc tggtggttga 47940
ctgatcacca taactgctaa tcattcaaac tatttagtct gtgacagagc caacacgcag 48000
tctgtcactg tcaggaaagt ggtaaaactg caactcaatt actgcaatgc cctcgtaatt 48060
aagtgaattt acaatatcgt cctgttcgga gggaagaacg cgggatgttc attcttcatc 48120

-continued acttttaatt gatgtatatg ctctcttttc tgacgttagt ctccgacggc aggcttcaat 48180
gacccaggct gagaaattcc cggacccttt ttgctcaaga gcgatgttaa tttgttcaat 48240
catttggtta ggaaagcgga tgttgcgggt tgttgttctg cgggttctgt tcttcgttga 48300
catgaggttg ccccgtattc agtgtcgctg atttgtattg tctgaagttg tttttacgtt 48360
aagttgatgc agatcaatta atacgatacc tgcgtcataa ttgattattt gacgtggttt 48420
gatggcctcc acgcacgttg tgatatgtag atgataatca ttatcacttt acgggtcctt 48480
tccggtgatc cgacaggtta cg 48502

<210> SEQ ID NO 32
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 32
tttttttttt tt 12

<210> SEQ ID NO 33
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 33
ggttgtttct gttggtgctg atattgcggc gtctgcttgg gtgtttaacc t 51

<210> SEQ ID NO 34
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 34
ggttaaacac ccaagcagac gccgcaatat cagcaccaac agaaacaacc tttgaggcga 60
gcggtcaa 68

<210> SEQ ID NO 35
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 35
ttgaccgctc gcctc 15

<210> SEQ ID NO 36
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 36
gatctgaagc ggcgcacgaa aaacgcgaaa gcgtttcacg ataatgcgaa aac 53

<210> SEQ ID NO 37
<211> LENGTH: 54

-continued

```
<212> TYPE: DNA
<213> ORGANISM: Artificial Sequence
<220> FEATURE:
<223> OTHER INFORMATION: Synthetic polynucleotide

<400> SEQUENCE: 37

ttttgttttc gcatttatcg tgaaacgctt tcgcgttttt cgtgcgccgc ttca          54
```

METHOD FOR MODIFYING A TEMPLATE DOUBLE STRANDED POLYNUCLEOTIDE USING A MUA TRANSPOSASE

This Application is a national stage filing under 35 U.S.C. § 371 of PCT International Application No. PCT/GB2015/050461, which has an international filing date of Feb. 18, 2015, and claims foreign priority benefits under 35 U.S.C. § 119(a)-(d) or 35 U.S.C. § 365(b) of British application number 1418159.8, filed Oct. 14, 2014. The contents of the aforementioned applications are herein incorporated by reference in their entireties.

FIELD OF THE INVENTION

The invention relates to a method for modifying a template double stranded polynucleotide, especially for characterisation using nanopore sequencing. The method produces from the template a plurality of modified double stranded polynucleotides. These modified polynucleotides can then be characterised.

BACKGROUND OF THE INVENTION

There are many commercial situations which require the preparation of a nucleic acid library. This is frequently achieved using a transposase. Depending on the transposase which is used to prepare the library it may be necessary to repair the transposition events in vitro before the library can be used, for example in sequencing.

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identity of the nucleotides are derived. Strand sequencing can involve the use of a polynucleotide binding protein to control the movement of the polynucleotide through the pore.

SUMMARY OF THE INVENTION

The inventors have surprisingly demonstrated that it is possible to modify a template double stranded polynucleotide to produce a plurality of shorter, modified double stranded polynucleotides. The modified double stranded polynucleotides may include, for instance, a hairpin loop or a single stranded leader sequence. These modifications can be designed such that the modified double stranded polynucleotides are each easier to characterise, such as by strand sequencing, than the original template polynucleotide. Subsequent characterisation of the modified polynucleotides allows the character of the template polynucleotide to be more easily determined.

The modification method of the invention uses a MuA transposase, a population of MuA substrates and a polymerase and is summarised in FIG. 1. The MuA substrates comprise an overhang and a hairpin loop on opposite strands. The MuA transposase is capable of fragmenting the template polynucleotide and producing fragments with overhangs at both ends. The MuA transposase is also capable of ligating a substrate to the overhang at one or both ends of the double stranded fragments. The strand of the substrate without an overhang is typically ligated to the strand of the fragment with an overhang. This leaves a single stranded gap in the resulting double stranded construct. The double stranded construct also has a hairpin loop on the opposite strand from the gap.

The polymerase is capable of using the strand comprising the hairpin loop as a template and displacing the strand containing the single stranded gap. The resulting double stranded construct contains two complementary strands containing a fragment of the template polynucleotide. The two strands in this construct can be separated and, preferably simultaneously, used as templates to produce two double stranded constructs which comprise a fragment of the template polynucleotide and in which the two strands are linked by a hairpin loop.

Accordingly, the invention provides a method for modifying a template double stranded polynucleotide, comprising:

(a) contacting the template polynucleotide with a MuA transposase and a population of double stranded MuA substrates each comprising (i) at least one overhang and (ii) at least one hairpin loop in the opposite strand from the strand comprising the at least one overhang such that the transposase fragments the template polynucleotide and ligates a substrate to one or both ends of the double stranded fragments and thereby produces a plurality of fragment/substrate constructs;

(b) contacting the fragment/substrate constructs with a polymerase such that the polymerase displaces the strands comprising the overhangs and replaces them with strands which complement the strands comprising the hairpin loops and thereby produces a plurality of double stranded constructs each comprising a double stranded fragment of the template polynucleotide; and (c) separating the two strands of the double stranded constructs and using the strands as templates to form a plurality of modified double stranded polynucleotides each comprising two complementary strands linked by at least one hairpin loop.

The invention also provides:

a plurality of modified double stranded polynucleotides produced using the method of the invention;

a population of double stranded polynucleotide MuA substrates for modifying a template polynucleotide, wherein the substrates are as defined above;

a method of characterising at least one polynucleotide modified using a method of the invention, comprising:

a) contacting the modified polynucleotide with a transmembrane pore such that at least one strand of the polynucleotide moves through the pore; and b) taking one or more measurements as the at least one strand moves with respect to the pore wherein the measurements are indicative of one or more characteristics of the at least one strand and thereby characterising the modified polynucleotide;

a method of characterising a template polynucleotide, comprising:

a) modifying the template polynucleotide using the method of the invention to produce a plurality of modified polynucleotides;

b) contacting each modified polynucleotide with a transmembrane pore such that at least one strand of each polynucleotide moves through the pore; and c) taking one or more measurements as each polynucleotide moves with respect to the pore wherein the measurements are indicative of one or more characteristics of each polynucleotide and thereby characterising the template polynucleotide; and a kit for modifying a template double stranded polynucleotide comprising (a) a population of MuA substrates as defined above, (b) a MuA transposase and (c) a polymerase.

DESCRIPTION OF THE FIGURES

FIG. 5 is identical to FIG. 1, except that each substrate comprises a leader sequence (labelled i) separated from the hairpin loop by a spacer (xxx; labelled h). The leader sequence was not used as a template because the polymerase (labelled e) could not move past the spacer.

DESCRIPTION OF THE SEQUENCE LISTING

Figure 1:
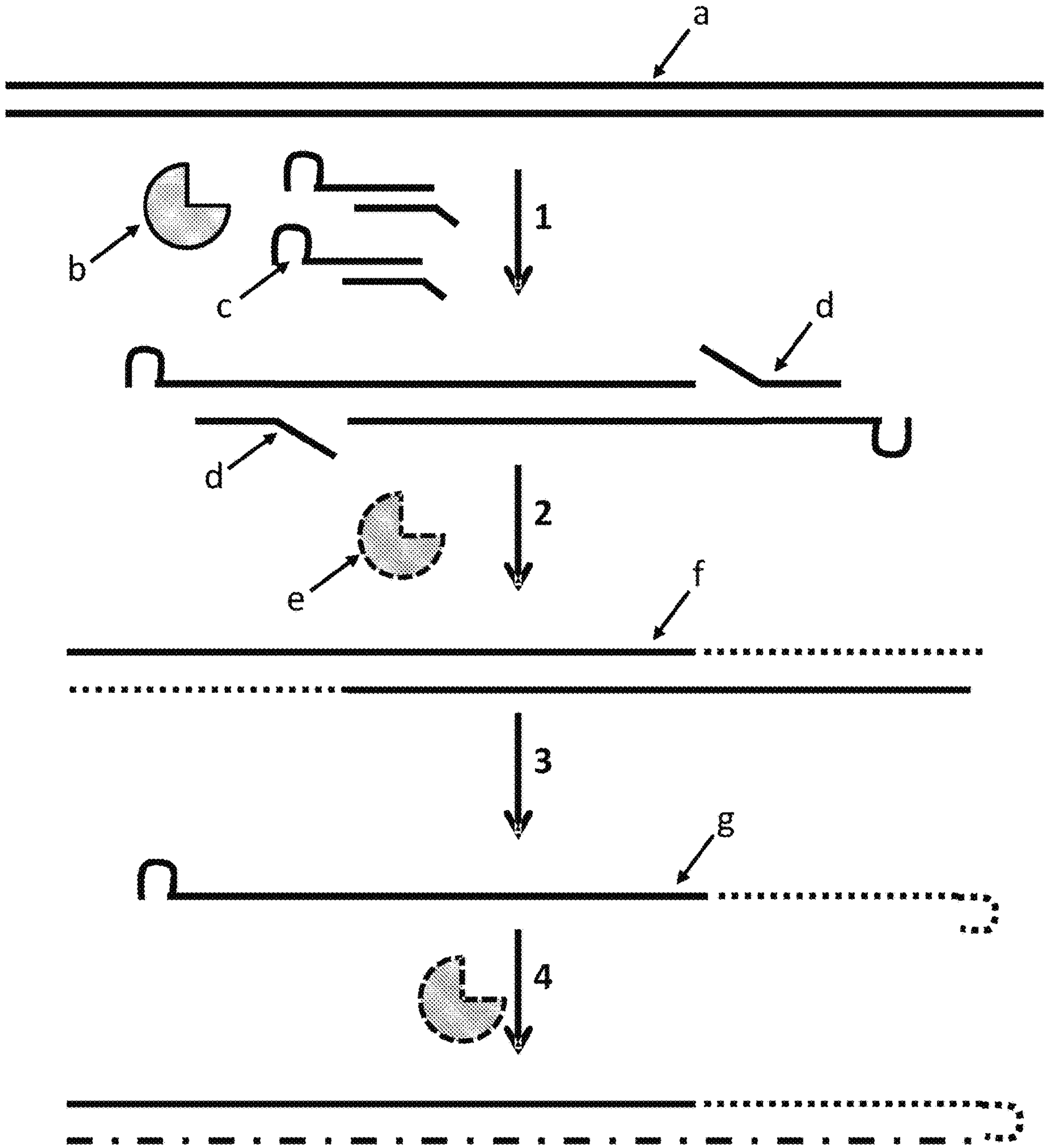
FIG. 1 shows a cartoon representation of a method of modifying a template double-stranded polynucleotide (labelled a). Step 1 involved contacting a template double-stranded polynucleotide with a MuA transposase (labelled b) and a population of double-stranded MuA substrates (labelled c, the double stranded MuA substrates each contained a 5' hairpin loop) so that the MuA transposase fragmented the template double-stranded polynucleotide and inserted the MuA substrates at each side of the point of fragmentation. Step 2 involved treating the template strand with a polymerase (labelled e) and dNTPs which displaced the DNA fragments labelled d and produced complementary strands to the DNA 5' hairpin loop. Step 3 involved heat treatment of the double-stranded DNA construct labelled f so that the strands were denatured into single-stranded DNA (labelled g). Finally, step 4 involved a DNA polymerase forming the complementary strand.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli.*

SEQ ID NO: 11 shows the amino acid sequence of exonuclease I enzyme (EcoExo I) from *E. coli.*

SEQ ID NO: 12 shows the codon optimised polynucleotide sequence derived from the xthA gene from *E. coli*. It encodes the exonuclease III enzyme from *E. coli.*

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NOs: 26 to 28 show the sequences of preferred MuA substrates of the invention.

SEQ ID NO: 29 shows a polynucleotide sequence used in Example 1.

SEQ ID NO: 30 shows a polynucleotide sequence used in Example 1. This sequence has the following polynucleotide sequence attached at its 5' end—GATCU.

SEQ ID NO: 31 shows the polynucleotide sequence, used in Example 1, of the Enterobacteria phage λ. The sequence contains an additional 12 base overhang attached at the 5' end of the template strand. The sequence shown here is that of the template strand only (the template complement is not shown).

SEQ ID NO: 32 shows a polynucleotide sequence used in Example 1.

SEQ ID NO: 33 shows a polynucleotide sequence used in Example 1.

SEQ ID NO: 34 shows a polynucleotide sequence used in Example 1.

SEQ ID NO: 35 shows a polynucleotide sequence used in Example 1.

SEQ ID NO: 36 shows a polynucleotide sequence used in Example 2.

SEQ ID NO: 37 shows a polynucleotide sequence used in Example 2.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes "polynucleotides", reference to "a substrate" includes two or more such substrates, reference to "a transmembrane protein pore" includes two or more such pores, and the like.

All publications, patents and patent applications cited herein, whether supra or infra, are hereby incorporated by reference in their entirety.

Modification Method of the Invention

The present invention provides a method of modifying a template polynucleotide. The template may be modified for any purpose. The method is preferably for modifying a template polynucleotide for characterisation, such as for strand sequencing. The template polynucleotide is typically the polynucleotide that will ultimately be characterised, or sequenced, in accordance with the invention. This is discussed in more detail below.

The method involves the formation of a plurality of modified double stranded polynucleotides. These modified double stranded polynucleotides are typically easier to characterise than the template polynucleotide, especially using strand sequencing. The plurality of modified double stranded polynucleotides may themselves be characterised in order to facilitate the characterisation of the template polynucleotide. For instance, the sequence of the template polynucleotide can be determined by sequencing each of the modified double stranded polynucleotides.

The modified double stranded polynucleotides are typically shorter than the template polynucleotide and so it is more straightforward to characterise them using strand sequencing. The modified double stranded polynucleotides also includes double the amount of information as discussed below.

The modified double strand polynucleotides can be selectively labelled by including the labels in the MuA substrates. Suitable labels include, but are not limited to, calibration sequences, coupling moieties and adaptor bound enzymes.

In some embodiments, the method introduces into the double stranded polynucleotides modifications which facilitate their characterisation using strand sequencing. It is well-established that coupling a polynucleotide to the membrane containing the nanopore lowers by several orders of magnitude the amount of polynucleotide required to allow its characterisation or sequencing. This is discussed in International Application No. PCT/GB2012/051191 (published as WO 2012/164270). The method of the invention allows the production of a plurality of double stranded polynucleotides each of which includes a means for coupling the polynucleotides to a membrane. This is discussed in more detail below.

The characterisation of double stranded polynucleotides using a nanopore typically requires the presence of a leader sequence designed to preferentially thread into the nanopore. The method of the invention allows the production of a plurality of double stranded polynucleotides each of which includes a single stranded leader sequence. This is discussed in more detail below.

It is also well established that linking the two strands of a double stranded polynucleotide by a bridging moiety, such as hairpin loop, allows both strands of the polynucleotide to be characterised or sequenced by a nanopore. This is advantageous because it doubles the amount of information obtained from a single double stranded polynucleotide. Moreover, because the sequence in the template complement strand is necessarily orthogonal to the sequence of the template strand, the information from the two strands can be combined informatically. Thus, this mechanism provides an orthogonal proof-reading capability that provides higher confidence observations. This is discussed in International Application No. PCT/GB2012/051786 (published as WO 2013/014451). The method of the invention allows the production of a plurality of modified double stranded polynucleotides in which the two strands of each polynucleotide are linked using a hairpin loop.

Template Polynucleotide

The method of the invention modifies a template double stranded polynucleotide, preferably for characterisation. The template polynucleotide is typically the polynucleotide that will ultimately be characterised, or sequenced, in accordance with the invention. It may also be called the target double stranded polynucleotide or the double stranded polynucleotide of interest.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide is double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated using the invention. For instance, the invention may concern characterising 2, 3, 4, 5, 6, 7, 8, 9, 10, 20, 30, 50, 100 or more polynucleotides. If two or more polynucleotides are characterized, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

The template polynucleotide is typically present in any suitable sample. The invention is typically carried out on a sample that is known to contain or suspected to contain the template polynucleotide. Alternatively, the invention may be carried out on a sample to confirm the identity of one or more template polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

MuA and Conditions

The template polynucleotide is contacted with a MuA transposase. This contacting occurs under conditions which allow the transposase to function, i.e. to fragment the template polynucleotide and to ligate MuA substrates to the one or both ends of the fragments. MuA transposase is commercially available, for instance from Thermo Scientific (Catalogue Number F-750C, 20 μL, (1.1 μg/μL)). Conditions under which MuA transposase will function are known in the art. Suitable conditions are described in the Examples.

Population of Substrates

The template polynucleotide is contacted with a population of double stranded MuA substrates. The double stranded substrates are polynucleotide substrates and may be formed from any of the nucleotides or nucleic acids discussed above. The substrates are typically formed from the same nucleotides as the template polynucleotide.

The population of substrates is typically homogenous (i.e. typically contains a plurality of identical substrates). The population of substrates may be heterogeneous (i.e. may contain a plurality of different substrates).

Suitable substrates for a MuA transposase are known in the art (Saariaho and Savilahti, Nucleic Acids Research, 2006; 34(10): 3139-3149 and Lee and Harshey, J. Mol. Biol., 2001; 314: 433-444).

Each substrate typically comprises a double stranded portion which provides its activity as a substrate for MuA transposase. The double stranded portion is typically the same in each substrate. The population of substrates may comprise different double stranded portions.

The double stranded portion in each substrate is typically at least 50 nucleotide pairs in length, such as at least 55, at least 60 or at least 65 nucleotide pairs in length. The double stranded portion in each substrate preferably comprises a dinucleotide comprising deoxycytidine (dC) and deoxyadenosine (dA) at the 3' end of each strand. The dC and dA are typically in different orientations in the two strands of the double stranded portion, i.e. one strand has dC/dA and the other strand has dA/dC at the 3' end when reading from 5' to 3'.

One strand of the double stranded portion preferably comprises the sequence shown in SEQ ID NO: 26 and the other strand of the double stranded portion preferably comprises the sequence shown in SEQ ID NO: 27.

```
                                              (SEQ 26)
5'-GTTTTCGCATTTATCGTGAAACGCTTTCGCGTTTTTCGTGCGCCGCT
TCA-3'

                                              (SEQ 27)
3'-CAAAAGCGTAAATAGCACTTTGCGAAAGCGCAAAAAGCACGCGGCGA
AGT-5'
```

Each substrate comprises at least one overhang. The overhang is typically a nucleotide overhang. There may be an overhang at one or both ends of each substrate. If the double stranded portion in each substrate comprises the sequence shown in SEQ ID NO: 26 hybridised to the sequence shown in SEQ ID NO: 27, the at least one overhang is preferably at the 5' end of the sequence shown in SEQ ID NO: 27.

Each substrate may comprise two overhangs, i.e. one at both ends of each substrate. If there is an overhang at both ends of a substrate, each overhang is typically on different strands of the double stranded polynucleotide portion. Overhangs are preferably located at the 5' end of a strand of the double stranded portion.

Each substrate preferably comprises only one overhang. The only one overhang is preferably at the 5' end of one strand of the double stranded portion.

The overhang may be at least 3, at least 4, at least 5, at least 6 or at least 7 nucleotides in length. The overhang is preferably 5 nucleotides in length.

In a preferred embodiment, one strand of the substrate comprises the sequence shown in SEQ ID NO: 26 and the other strand of the substrate comprises the sequence shown in SEQ ID NO: 28 (see below).

(SEQ 26)
```
5'-GTTTTCGCATTTATCGTGAAACGCTTTCGCGTTTTTCGTGCGCCGCT
TCA-3'
```

(SEQ 28)
```
3'-CAAAAGCGTAAATAGCACTTTGCGAAAGCGCAAAAAGCACGCGGCGA
AGTCTAG-5'
```

The substrates in the population may have any of the structures disclosed in International Application No. PCT/GB2014/052505.

Each substrate comprises at least one hairpin loop in the opposite strand from the strand comprising the at least one overhang. The hairpin loop typically does not link the two strands of the substrate. The hairpin loop may be an internal hairpin loop, i.e. not at the end of the opposite strand from the strand comprising the at least one overhang. Internal hairpin loops are preferably adjacent to a spacer past which any polymerase used in the method of the invention cannot move. The spacer may be located on either side of the hairpin loop. Any of the spacers discussed below, such as one or more iSpC3 groups (i.e. nucleotides which lack sugar and a base), one or more spacer 9 (iSp9) groups or one or more spacer 18 (iSp18) groups, may be used. Internal hairpin loops are preferably adjacent to non-natural nucleotides, such as nitroindoles, past which any polymerase used in the method of the invention cannot move. Any of the different nucleotide species discussed below may be used.

The hairpin loop is preferably at or near the end of the opposite strand from the strand comprising the at least one overhang. The hairpin loop is near the end of the opposite strand from the strand comprising the at least one overhang if it is 20 nucleotides or fewer, 15 nucleotides or fewer, 10 nucleotides or fewer or 5 nucleotides or fewer from the end of the opposite strand from the strand comprising the at least one overhang. The hairpin loop is 20 nucleotides or fewer from the end of the strand if there are 20 nucleotides or fewer between the last nucleotide forming the stem part (hybridised part) of the end of the strand. The hairpin loop is preferably at the end of the opposite strand from the strand comprising the at least one overhang. There may be a hairpin loop at one or both ends of each substrate. The hairpin loop is preferably at the opposite end of the substrate from the at least one overhang.

The hairpin loop is typically a nucleotide hairpin loop. If the double stranded portion in each substrate comprises the sequence shown in SEQ ID NO: 26 hybridised to the sequence shown in SEQ ID NO: 27, the at least one hairpin loop is preferably at the 5' end of the sequence shown in SEQ ID NO: 26.

Each substrate may comprise two hairpin loops, i.e. one in both strands of each substrate or one at both ends of each substrate. If there is a hairpin loop at both ends of a substrate, each hairpin loop is typically on different strands of the double stranded polynucleotide portion. Hairpin loops are preferably located at the 5' end of a strand of the double stranded portion.

Each substrate preferably comprises only one hairpin loop. The only one hairpin loop is preferably in the opposite strand from the strand comprising the at least one overhang. The only one hairpin loop is preferably at the opposite end of the substrate from the at least one overhang and in the opposite strand from the strand comprising the at least one overhang. The only one hairpin loop is preferably at the 5' end of one strand of the double stranded portion and in the opposite strand from the strand comprising the at least one overhang.

In a preferred embodiment, each substrate comprises one overhang at the 5' end of one strand of the double stranded portion and a hairpin loop at the 5' end of the other strand of the double stranded portion. In a most preferred embodiment, one strand of the substrate comprises the sequence shown in SEQ ID NO: 26 and the other strand of the substrate comprises the sequence shown in SEQ ID NO: 28 (see above) and the hairpin loop is at the 5' end of the sequence shown in SEQ ID NO: 26.

Suitable hairpin loops can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length.

The hairpin loop may be formed from any of the nucleotides discussed above. The hairpin loop may be formed from the same nucleotides as the double stranded portion. The hairpin loop is preferably formed from nucleotides which result in the hairpin loop having a lower melting temperature (Tm) than the double stranded portion. Melting temperature can be measured using routine techniques. If the double stranded portion comprises RNA, the hairpin is preferably formed from nucleotides containing adenosine (A), uridine (U), inosine (I) and zebularine (Z). If the double stranded portion comprises DNA, the hairpin is preferably formed from nucleotides containing deoxyadenosine (dA), thymidine (dT), deoxyinosine (dI) and deoxyzebularine (dZ). The replacement of guanosine (G)/deoxyguanosine (dG) with inosine (I)/deoxyinosine (dI) and the replacement of cytidine (C)/deoxycytidine (dC) with zebularine (Z)/deoxyzebularine (dZ) reduces the Tm of the hairpin compared with the double stranded portion. I/dI and Z/dZ only form two hydrogen bonds whereas G/dG and C/dC form three hydrogen bonds. In the method of the invention, the polymerase replaces the overhang strands with new strands which complement the strands comprising the hairpin loops. The hairpin loops having a lower Tm may be used to form complementary hairpins having a higher Tm, i.e. hairpins formed from nucleotides having a higher Tm. The polymerase may replace the overhang strands with new strands which complement the strands comprising the hairpin loops, wherein the new strands comprise hairpin loops having a higher Tm than the hairpin loops in the template strands. For instance, a hairpin loop formed from nucleotides containing adenosine (A)/deoxyadenosine (dA), uridine (U)/thymidine (dT), inosine(I)/deoxyinosine (dI) and zebularine (Z)/deoxyzebularine (dZ) may be used to form a complementary RNA or DNA hairpin loop. The difference in Tm between the two hairpins means that they are more stable as individual hairpins than hybridised together. This means that the two hairpin loops form their respective loops rather than hybridise together. This facilitates the last step of the method in which the two strands of the double stranded constructs are separated and used as templates to form a plurality of modified double stranded polynucleotides each comprising two complementary strands linked by at least one hairpin loop. For instance, the separation may be performed at room temperature.

Each substrate may comprise a selectable binding moiety. If present, the selectable binding moiety is preferably in the hairpin loop. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a nucleic acid sequence, antibodies, antibody fragments, such as Fab and ScSv, antigens, nucleic acid binding proteins, poly histidine tails and GST tags. The most preferred selective binding moieties are biotin and a selectable nucleic acid sequence. Biotin specifically binds to a surface coated with avidins. Selectable nucleic acid sequences specifically bind (i.e. hybridize) to a surface coated with homologous sequences. Alternatively, selectable nucleic acid sequences specifically bind to a surface coated with nucleic acid binding proteins.

Figure 5:
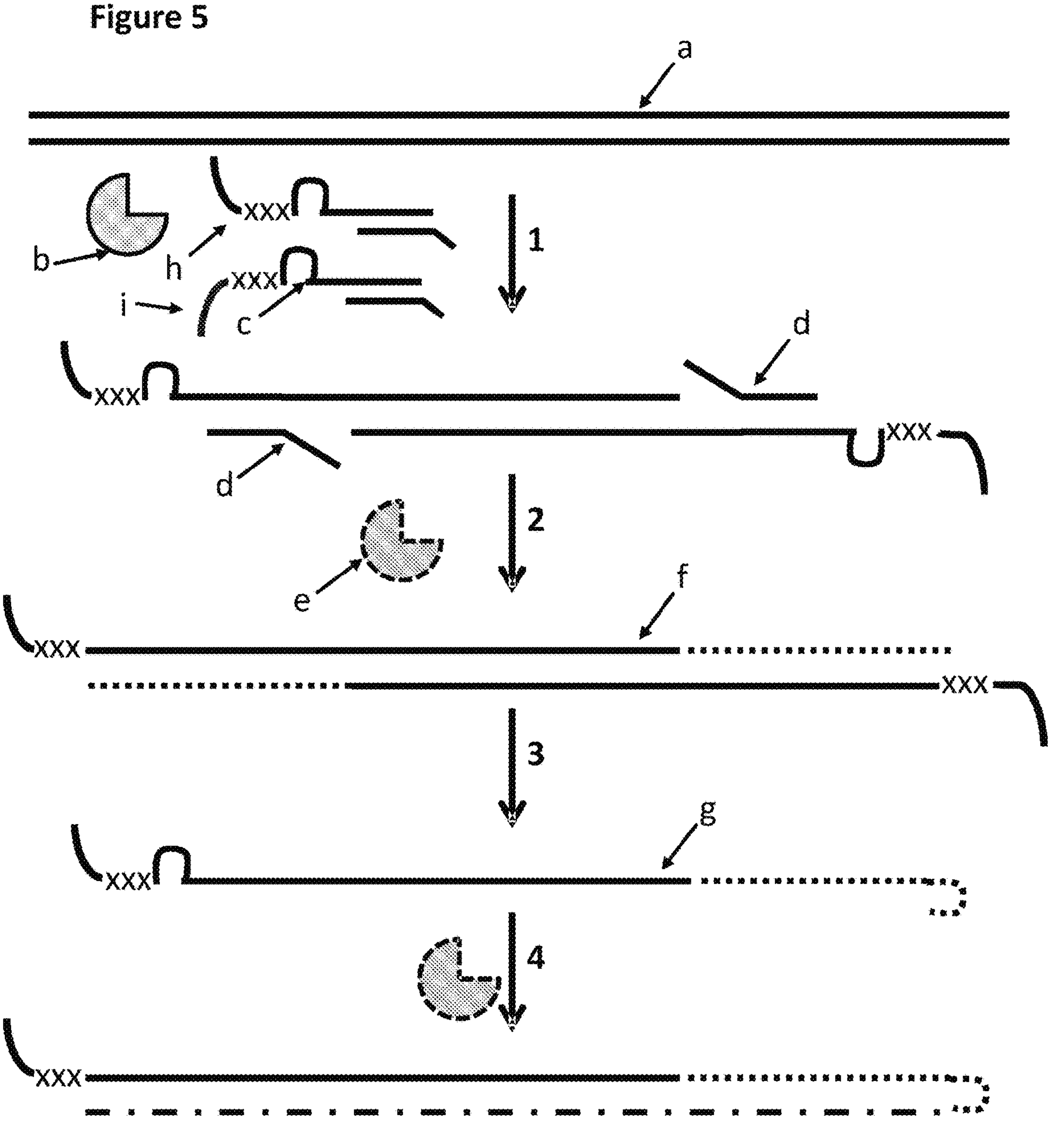
FIG. 5 shows a cartoon representation of a preferred method of modifying a template double-stranded polynucleotide (labelled a).

Each substrate may comprise a leader sequence. The leader sequences is typically on the same strand as the at least one hairpin loop. The leader sequence is typically at the same end of the substrate as the hairpin loop. The leader sequence is typically located at the end of the strand comprising the at least one hairpin loop (i.e. the hairpin loop is located between the terminal leader sequence and the rest of the substrate). The leader sequence is typically separated from the hairpin loop by a spacer past which any polymerase used in the method of the invention cannot move. Any of the spacers discussed below, such as one or more iSpC3 groups (i.e. nucleotides which lack sugar and a base), one or more spacer 9 (iSp9) groups or one or more spacer 18 (iSp18) groups, may be used. The spacer means that the leader sequence is not used as a template in steps (b) and (c) and so remains single stranded at the end of the method. This allows the leader sequence to perform its function. An example of this is shown in FIG. 5.

The leader sequence preferentially threads into the pore. The leader sequence facilitates the characterisation method of the invention. The leader sequence is designed to preferentially thread into the pore and thereby facilitate the movement of polynucleotide through the pore. The leader sequence can also be used to link the polynucleotide to the one or more anchors as discussed below. The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises one or more spacers.

The leader sequence can be any length, but is typically 10 to 150 nucleotides in length, such as from 20 to 150 nucleotides in length. The length of the leader typically depends on the transmembrane pore used in the method.

Fragmentation

The transposase fragments the template double stranded polynucleotide to form a plurality of double stranded fragments. The transposase also ligates a substrate to one or both ends of the double stranded fragments and thereby produces a plurality of fragment/substrate constructs. The transposase preferably ligates a substrate to both ends of the double stranded fragments and thereby produces a plurality of fragment/substrate constructs each having a hairpin loop at both ends. An example of this can be seen in FIG. 1.

Polymerase

The fragment/substrate constructs produced by the transposase are contacted with a polymerase. Any of the polymerases discussed below may be used. The polymerase is preferably Klenow or 9° North. The polymerase is more preferably LongAmp® Taq DNA Polymerase (which is commercially available from New England Biolabs® Inc.), Phusion® High-Fidelity DNA Polymerase (which is commercially available from New England Biolabs® Inc.) or KAPA HiFi (which is commercially available from KAPA Biosystems).

The constructs are contacted with the polymerase under conditions in which the polymerase can displace the overhang strands and form complement polynucleotides. Such conditions are known in the art. For instance, the constructs are typically contacted with the polymerase in commercially available polymerase buffer, such as buffer from New England Biolabs® or KAPA Biosystems. The temperature is preferably from 20 to 37° C. for Klenow or from 60 to 75° C. for 9° North, LongAmp® Taq DNA Polymerase, Phusion® High-Fidelity DNA Polymerase or KAPA HiFi.

The polymerase displaces the strands comprising the overhangs from the fragment/substrate constructs. The polymerase replaces the overhang strands with new strands which complement the strands comprising the hairpin loops. This produces a plurality of double stranded constructs each comprising a double stranded fragment of the template polynucleotide. Part of the new strands formed by the polymerase are typically complementary to the hairpin loop. This means that the hairpin loops typically form part of the double stranded polynucleotide in the constructs. An example of this can be seen in FIG. 1.

The polymerase may form new strands comprising any of the nucleotides discussed above and below. The polymerase is provided with a population of free nucleotides which complement the nucleotides in the strands comprising the hairpin loops. The polymerase may use the free nucleotides to form the new strands.

Separation/Replication

The two strands of the double stranded constructs are separated and the strands are used as templates to form a plurality of modified double stranded polynucleotides each comprising two complementary strands linked by at least one hairpin loop. An example of this is shown in FIG. 1.

The two strands may be completely separated before they are used as templates. The two strands may be separated and used as templates at the same time (i.e. simultaneously). In other words, the two strands do not need to be completely separated or the two strands may be partially separated before they are used as templates.

The two strands may be separated in any manner. The method preferably comprises separating the two strands of the double stranded constructs by increasing one or more of pH, temperature and ionic strength. An increased temperature is preferred. The method preferably comprises increasing the temperature to 95° C. The method preferably comprises increasing the temperature to 95° C. and then decreasing the temperature to 55° C. The method preferably comprises increasing the temperature to 95° C., decreasing the temperature to 55° C. and increasing the temperature to 68° C. The method most preferably comprises incubating the double stranded constructs for 2 minutes at 95° C., 30 seconds at 55° C. and 30 minutes at 68° C. Increases in pH may be achieved using formamide or sodium hydroxide (NaOH). Enzymes, such as a helicase or one that digests the template strand (e.g. USER if that strand had dU instead of dT), may also be used to separate the strands. Any of the helicases discussed below may be used.

As discussed in more detail below, the two strands may be separated using a polymerase. The polymerase may be any of those discussed above or below.

Any method may be used to form new polynucleotides using the separated strands as templates. The method preferably comprises contacting the strands with a polymerase such that the polymerase uses the strands as templates to form the plurality of modified double stranded polynucleotides. Any of the polymerases discussed above or below may be used.

Alternatively, the method may comprise (i) contacting the plurality of strands with a population of nucleotide oligomers which comprises every possible combination of nucleotides which are complementary to all of the nucleotides in the strands under conditions in which the oligomers are capable of hybridising to the strands and (ii) ligating together those oligomers that hybridise to the strands to form the plurality of modified double stranded polynucleotides. Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a wash in from 1× (0.1650 M Na+) to 2× (0.33 M Na+) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na+) to 1× (0.1650 M Na+) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na+) SSC at 60° C. Preferred conditions are preferably 10 uM oligomers in 10 mM Tris-HCl, 50 mM NaCl, pH 7 and heat to 98° C. before cooling to 18° C. at 2° C. per minute.

The oligomers in the population typically have from 2 to 16 nucleotides. All of the oligomers in the population may have 2, 3, 4, 5, 6, 7, 8, 9, 10, 11, 12, 13, 14, 15 or 16 nucleotides. The oligomers in the population may have different lengths. All of the oligomers in the population preferably have the same length. The oligomers may comprise any of the nucleotides discussed above. The nucleotides are complementary to the nucleotides in the strands to which the oligomers hybridise. It is straightforward for a person skilled in the art to identify nucleotides that are complementary to those nucleotides. A nucleotide is complementary to another nucleotide if it hybridises through base pairing, preferably Watson and Crick base pairing, to the nucleotide. A complementary nucleotide may hybridise to other nucleotides with which it is not complementary, but to a smaller degree than it hybridises to the nucleotide with which it is complementary. N preferably comprises the nucleobases adenine (A), uracil (U), guanine (G) or cytosine (C). Alternatively, N preferably comprises the nucleobases A, thymine (T), G or C. A is complementary to T or U and vice versa. G is complementary to C and vice versa.

The population comprises every possible combination of nucleotides which are complementary to all of the nucleotides in the strands. This means that the oligomers will hybridise to most, if not all, of the strands whatever their sequences. For instance, if N comprises the nucleobases adenine (A), uracil (U), guanine (G) or cytosine (C), the population comprises every possible combination of A, U, G and C. Similarly, if N comprises the nucleobases A, thymine (T), G or C, the population comprises every possible combination of A, T, G and C.

It is straightforward to design and obtain a population of oligomers having the requisite combination. For instance, if all of the oligomers in the population comprise or consist of NN and N is A, T, G or C, then the population comprises AT, AG, AC, TA, TG, TC, GA, GT, GC, CA, CT and CG. Similarly, if all of the oligomers in the population comprise or consist of NNN and N is A, T, G or C, then the population comprises ATG, ATC, AGT, AGC, ACT, ACG, TAG, TAC, TGA, TGC, TCA, TCG, GAT, GAC, GTA, GTC, GCA, GCT, CAT, CAG, CTA, CTG, CGA and CGT. Once the generic formula, such as NN or NNN has been designed, populations comprising all of the possible combinations of N are commercially available, for instance from Intergrated DNA Technologies (IDT), Sigma and Invitrogen.

The oligomers are capable of being ligated together in accordance with the invention. All of the oligomers in the population preferably have a phosphate group or an adenylate group at the 5' end.

The hybridised oligomers may be ligated together using any method known in the art. The oligomers are preferably ligated using a ligase, such as T4 DNA ligase, *E. coli* DNA ligase, Taq DNA ligase, Tma DNA ligase and 9° N DNA ligase.

The oligomers may also be chemically ligated if reactive groups are present on the ends of the oligomers. In such embodiments, steps need to be taken to prevent the oligomers from ligating to each other in solution. The ligation reaction is typically initiated using the hairpin on a strand as a primer.

In a preferred embodiment, the method preferably comprises contacting the plurality of double stranded constructs with a polymerase such that the polymerase simultaneously separates the two strands of the double stranded constructs and uses the strands as templates to form the plurality of modified double stranded polynucleotides. Any of the polymerases discussed above or below may be used. The polymerase may form new strands comprising any of the nucleotides discussed above and below. The polymerase is provided with a population of free nucleotides which complement the nucleotides in the template strands. The polymerase may use the free nucleotides to form the new strands.

Modified Polynucleotides

If the polymerase uses the strands as templates to form a plurality of modified double stranded polynucleotides, the method may comprise contacting the strands with a polymerase and a population of free nucleotides under conditions in which the polymerase uses the strands as templates to form a plurality of modified double stranded polynucleotides, wherein the polymerase replaces one or more of the nucleotide species in the strands with a different nucleotide species when forming the modified double stranded polynucleotides. The polymerase may be used to simultaneously separate the strands as discussed above. This type of modification is described in UK Application No. 1403096.9. Any of the polymerases discussed above or below may be used. The polymerase is preferably Klenow or 9° North. Suitable conditions are discussed above.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the strands with different nucleotide species in the new strands (i.e. the strands produced using the polymerase) of the modified double stranded polynucleotides, the new strands contain k-mers which differ from those in the template strands. The different k-mers in the new strands are capable of producing different current measurements from the k-mers in the template strands and so the new strands provide different information from the template strands. The additional information from the new strands can make it easier to characterise the modified double stranded polynucleotides and hence the template polynucleotide. In some instances, the modified double stranded polynucleotides themselves may be easier to characterise. For instance, the modified double stranded polynucleotides may be designed to include k-mers with an increased separation or a clear separation between their current measurements or k-mers which have a decreased noise.

The polymerase preferably replaces two or more of the nucleotide species in the template strands with different nucleotide species when forming the modified double stranded polynucleotides. The polymerase may replace each of the two or more nucleotide species in the template strands with a distinct nucleotide species. The polymerase may replace each of the two or more nucleotide species in the template strands with the same nucleotide species.

If the template strands are DNA, the different nucleotide species typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the template strands are RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcytidine.

The different nucleotide species may be a universal nucleotide. A universal nucleotide is one which will hybridise or bind to some degree to all of the nucleotides in the template strands. A universal nucleotide is preferably one which will hybridise or bind to some degree to nucleotides comprising the nucleosides adenosine (A), thymine (T), uracil (U), guanine (G) and cytosine (C). The universal nucleotide may hybridise or bind more strongly to some nucleotides than to others. For instance, a universal nucleotide (I) comprising the nucleoside, 2'-deoxyinosine, will show a preferential order of pairing of I-C>I-A>I-G approximately=I-T. The polymerase will replace a nucleotide species with a universal nucleotide if the universal nucleotide takes the place of the nucleotide species in the population. For instance, the polymerase will replace dGMP with a universal nucleotide, if it is contacted with a population of free dAMP, dTMP, dCMP and the universal nucleotide.

The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyino sine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The different nucleotide species preferably comprises a chemical atom or group absent from the nucleotide species it is replacing. The chemical group is preferably a propynyl group, a thio group, an oxo group, a methyl group, a hydroxymethyl group, a formyl group, a carboxy group, a carbonyl group, a benzyl group, a propargyl group or a propargylamine group. The chemical group or atom may be or may comprise a fluorescent molecule, biotin, digoxigenin, DNP (dinitrophenol), a photo-labile group, an alkyne, DBCO, azide, free amino group, a redox dye, a mercury atom or a selenium atom.

Commercially available nucleosides comprising chemical groups which are absent from naturally-occurring nucleosides include, but are not limited to, 6-Thio-2'-deoxyguanosine, 7-Deaza-2'-deoxyadenosine, 7-Deaza-2'-deoxyguanosine, 7-Deaza-2'-deoxyxanthosine, 7-Deaza-8-aza-2'-deoxyadenosine, 8-5'(5'S)-Cyclo-2'-deoxyadenosine, 8-Amino-2'-deoxyadenosine, 8-Amino-2'-deoxyguanosine, 8-Deuterated-2'-deoxyguanosine, 8-Oxo-2'-deoxyadenosine, 8-Oxo-2'-deoxyguanosine, Etheno-2'-deoxyadenosine, N6-Methyl-2'-deoxyadenosine, 06-Methyl-2'-deoxyguanosine, O6-Phenyl-2'deoxyinosine, 2'-Deoxypseudouridine, 2-Thiothymidine, 4-Thio-2'-deoxyuridine, 4-Thiothymidine, 5' Aminothymidine, 5-(1-Pyrenylethynyl)-2'-deoxyuridine, 5-(C2-EDTA)-2'-deoxyuridine, 5-(Carboxy)vinyl-2'-deoxyuridine, 5,6-Dihydro-2'-deoxyuridine, 5.6-Dihydrothymidine, 5-Bromo-2'-deoxycytidine, 5-Bromo-2'-deoxyuridine, 5-Carboxy-2'-deoxycytidine, 5-Fluoro-2'-deoxyuridine, 5-Formyl-2'-deoxycytidine, 5-Hydroxy-2'-deoxycytidine, 5-Hydroxy-2'-deoxyuridine, 5-Hydroxymethyl-2'-deoxycytidine, 5-Hydroxymethyl-2'-deoxyuridine, 5-Iodo-2'-deoxycytidine, 5-Iodo-2'-deoxyuridine, 5-Methyl-2'-deoxycytidine, 5-Methyl-2'-deoxyisocytidine, 5-Propynyl-2'-deoxycytidine, 5-Propynyl-2'-deoxyuridine, 6-O-(TMP)-5-F-2'-deoxyuridine, C4-(1,2,4-

Triazol-1-yl)-2'-deoxyuridine, C8-Alkyne-thymidine, dT-Ferrocene, N4-Ethyl-2'-deoxycytidine, 04-Methylthymidine, Pyrrolo-2'-deoxycytidine, Thymidine Glycol, 4-Thiouridine, 5-Methylcytidine, 5-Methyluridine, Pyrrolocytidine, 3-Deaza-5-Aza-2'-O-methylcytidine, 5-Fluoro-2'-O-Methyluridine, 5-Fluoro-4-O-TMP-2'-O-Methyluridine, 5-Methyl-2'-O-Methylcytidine, 5-Methyl-2'-O-Methylthymidine, 2',3'-Dideoxyadenosine, 2',3'-Dideoxycytidine, 2',3'-Dideoxyguanosine, 2',3'-Dideoxythymidine, 3'-Deoxyadenosine, 3'-Deoxycytidine, 3'-Deoxyguanosine, 3'-Deoxythymidine and 5'-O-Methylthymidine. The different nucleotide species may comprise any of these nucleosides.

Alternatively, the different nucleotide species preferably lacks a chemical group or atom present in the nucleotide species it is replacing.

The different nucleotide species preferably has an altered electronegativity compared with the one or more nucleotides being replaced. The different nucleotide species having an altered electronegativity preferably comprises a halogen atom. The halogen atom may be attached to any position on the different nucleotide species, such as the nucleobase and/or the sugar. The halogen atom is preferably fluorine (F), chlorine (Cl), bromine (Br) or iodine (I). The halogen atom is most preferably F or I.

Commercially available nucleosides comprising a halogen include, but are not limited to, 8-Bromo-2'-deoxyadenosine, 8-Bromo-2'-deoxyguanosine, 5-Bromouridine, 5-Iodouridine, 5-Bromouridine, 5-Iodouridine, 5'-Iodothymidine and 5-Bromo-2'-O-methyluridine. The different nucleotide species may comprise any of these nucleosides.

The method preferably further comprises selectively removing the nucleobases from the one or more different nucleotides species in the modified double stranded polynucleotides. This results in abasic nucleotides in the modified double stranded polynucleotides. An abasic nucleotide is a nucleotide that lacks a nucleobase. The abasic nucleotide typically contains a sugar and at least one phosphate group. The sugar is typically a pentose sugar, such as ribose and deoxyribose. The abasic nucleotide is typically an abasic ribonucleotide or an abasic deoxyribonucleotide. The abasic nucleotide typically contains a monophosphate, diphosphate or triphosphate. Phosphates may be attached on the 5' or 3' side of an abasic nucleotide.

The nucleobases may be selectively removed using any method known in the art. For instance, certain DNA repair proteins, such as human alkyladenine DNA glycosylase (hAAG), are capable of selectively removing 3-methyl adenine, 7-methyl guanine, 1, N6-ethenoadenine and hypoxanthine from nucleotides. Also, dUMP can be selectively removed using uracil DNA glycosylase.

Additional Polymerase Step

Figure 8:
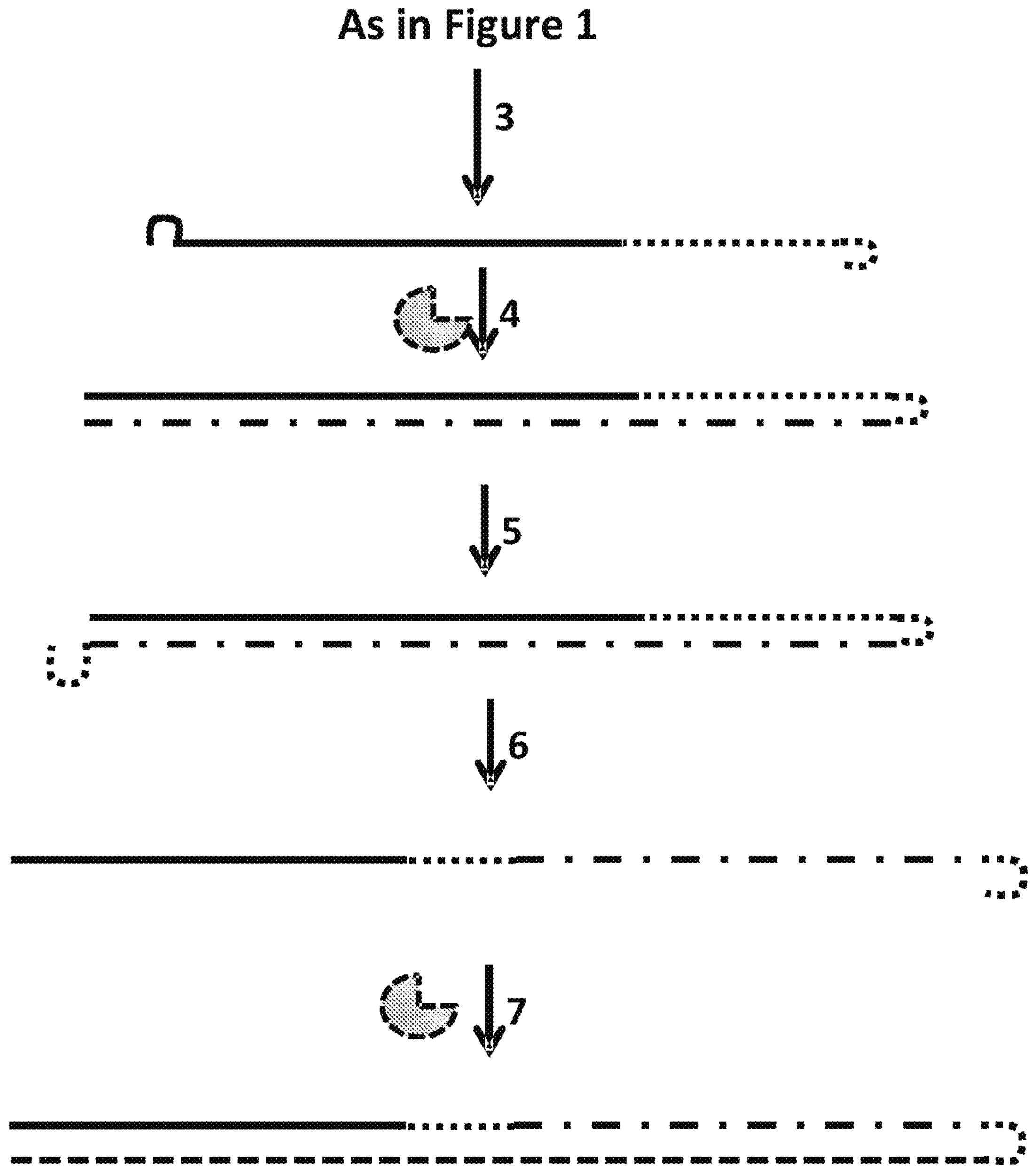
FIG. 8 shows a cartoon representation of a preferred method of the invention. Steps 1 to 4 were the same as in FIG. 1. Step 5 involved adding a hairpin loop to the construct formed in FIG. 1. Step 6 involved heat treatment of the modified double-stranded polynucleotide so that the strands were denatured into single-stranded construct. Finally, step 7 involved a DNA polymerase forming the complementary strand.

In another preferred embodiment, the amount of information in the modified double stranded polynucleotides is doubled to facilitate characterisation of the template polynucleotide. An example of this is shown in FIG. 8. The method preferably comprises (d) separating the two strands of the modified double stranded polynucleotides and using the strands as templates to form a plurality of adapted double stranded polynucleotides each comprising two complementary strands linked by at least one hairpin loop, wherein each complementary strand comprises two complementary sequences. One of the two complementary sequences in each complementary strand is derived from the template double stranded polynucleotide. Step (d) typically comprises before separation attaching a hairpin loop to the modified double stranded polynucleotides at the other end of the modified double stranded polynucleotides from the at least one hairpin loop which links the complementary strands. This hairpin loop preferably does not link the strands of the modified double stranded polynucleotides. The hairpin may form a nucleation point for the polymerase. When the separated strands of the modified double stranded polynucleotides are used as templates, the attached hairpin loop is also used as a template and links the two complementary strands of the adapted double stranded polynucleotides, i.e links the template strands from the modified double stranded polynucleotides and the new strands formed from the templates.

Step (d) may be carried out in any of the ways discussed above. For instance, step (d) may comprises separating the two strands of the modified double stranded polynucleotides by increasing one or more of pH, temperature and ionic strength. Step (d) may comprise contacting the separated strands with a polymerase such that the polymerase uses the strands as templates to form the plurality of adapted double stranded polynucleotides. Step (d) may comprise (i) contacting the plurality of separated strands with a population of nucleotide oligomers which comprises every possible combination of nucleotides which are complementary to all of the nucleotides in the strands under conditions in which the oligomers are capable of hybridising to the strands and (ii) ligating together those oligomers that hybridise to the strands to form the plurality of adapted double stranded polynucleotides. Step (d) may comprise contacting the plurality of modified double stranded polynucleotides with a polymerase such that the polymerase simultaneously separates the two strands of the modified double stranded polynucleotides and uses the strands as templates to the plurality of adapted double stranded polynucleotides. Any of the embodiments discussed above may apply to step (d). For instance, step (d) may comprise replacing one or more nucleotide species in the template strands with different nucleotide species in the new strands.

Y Adaptors

If each substrate does not comprise a leader sequence, the method preferably further comprises attaching Y adaptors to the plurality of modified double stranded polynucleotides at the opposite ends from the hairpin loops. The Y adaptors are typically polynucleotide adaptors. They may be formed from any of the polynucleotides discussed above. The Y adaptors typically comprise (a) a double stranded region and (b) a single stranded region or a region that is not complementary at the other end. The Y adaptors may be described as having an overhang if it comprises a single stranded region. The presence of a non-complementary region in the Y adaptors gives them their Y shape since the two strands typically do not hybridise to each other unlike the double stranded portion. The Y adaptors may comprise one or more anchors as discussed in more detail below.

The Y adaptors may be ligated to the modified double stranded polynucleotides. Ligation may be carried out using any method known in the art. For instance, the Y adaptors may be ligated using a ligase, such as T4 DNA ligase, *E. coli* DNA ligase, Taq DNA ligase, Tma DNA ligase and 9° N DNA ligase.

Products of the Invention

The invention also provides a population of double stranded MuA substrates for modifying a template polynucleotide, wherein each substrate comprises at least one overhang of universal nucleotides. The invention also provides a population of double stranded MuA substrates for modifying a template polynucleotide, wherein each substrate comprises (i) at least one overhang and (ii) at least one hairpin loop in the opposite strand from the strand comprising the at least one overhang. The substrates may be any of those described above. The substrates preferably comprise a double stranded portion as defined above. The double stranded portion preferably comprises SEQ ID NOs: 26 and 27 as discussed above. The double stranded portion more preferably comprises SEQ ID NOs: 26 and 28 as discussed above. Preferred populations of the invention are those in which each substrate comprises an overhang at one end and a hairpin loop at the other end.

The invention also provides a plurality of polynucleotides modified using the method of the invention. The plurality of polynucleotides may be in any of the forms discussed above. The modified double stranded polynucleotides comprise two complementary strands comprising a double stranded fragment of the template polynucleotide linked by a hairpin loop.

The population or plurality may be isolated, substantially isolated, purified or substantially purified. A population or plurality is isolated or purified if it is completely free of any other components, such as the template polynucleotide, lipids or pores. A population or plurality is substantially isolated if it is mixed with carriers or diluents which will not interfere with its intended use. For instance, a population or plurality is substantially isolated or substantially purified if it is present in a form that comprises less than 10%, less than 5%, less than 2% or less than 1% of other components, such as lipids or pores.

Characterisation Methods

The invention also provides methods of characterising at least one polynucleotide modified using a method of the invention. The modified polynucleotide is contacted with a transmembrane pore such that at least one strand of the polynucleotide moves through the pore. One or more measurements are taken as the at least one strand moves with respect to the pore. The measurements are indicative of one or more characteristics of the at least one strand and this allows characterisation of the modified polynucleotide.

The invention also provides methods of characterising a template polynucleotide. The template polynucleotide is modified using the invention to produce a plurality of modified polynucleotides. Each modified polynucleotide is contacted with a transmembrane pore such that at least one strand of each polynucleotide moves through the pore. One or more measurements are taken as each polynucleotide moves with respect to the pore. The measurements are indicative of one or more characteristics of each polynucleotide this allows the template polynucleotide to be characterised.

In a preferred embodiment, both strands of the/each modified polynucleotide move through the pore. If both strands move through the pore, the two strands are typically separated. The two strands may be separated using any method known in the art. For instance, they may be separated by a polynucleotide binding protein or using conditions which favour dehybridisation (examples of conditions which favour dehybridisation include, but are not limited to, high temperature, high pH and the addition of agents that can disrupt hydrogen bonding or base pairing, such as formamide and urea).

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

The one or more selectively amplified probes or one or more amplification products are preferably characterised by (i) contacting the probes or amplification products with a transmembrane pore such that the probes or amplification products move through the pore and (ii) taking one or more measurements as the probes or amplification products move with respect to the pore wherein the measurements are indicative of one or more characteristics of the probes or amplification products and thereby characterising the probes or amplification products.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β pore forming toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP), and other pores, such as lysenin. α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp, such as MspA, or from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4.

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. Suitable variants are disclosed in International Application No. PCT/GB2012/050301 (published as WO 2012/107778) and UK Application No. 1407809.1 (ONT IP 057). A preferred variant of SEQ ID NO: 2 comprises N93D. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Characterisation

The method may involve measuring two, three, four or five or more characteristics of the modified or template polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The polynucleotide is contacted with a transmembrane pore. The pore is typically present in a membrane. Suitable membranes are discussed below. The method may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in International Application No. PCT/GB08/000562 (WO 2008/102120).

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The method may involve measuring the current passing through the pore as the polynucleotide moves with respect to the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The method is typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Polynucleotide Binding Protein

The method preferably comprises contacting the/each polynucleotide with a polynucleotide binding protein such that the protein controls the movement of at least one strand of the/each polynucleotide through the pore.

More preferably, the method comprises (a) contacting the/each polynucleotide with the pore and a polynucleotide binding protein such that the protein controls the movement of at least one strand of the/each polynucleotide through the pore and (b) taking one or more measurements as the/each polynucleotide moves with respect to the pore, wherein the measurements are indicative of one or more characteristics of the/each polynucleotide, and thereby characterising the modified or template polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The protein may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Tga (SEQ ID NO: 20), Hel308 Mhu (SEQ ID NO: 21), TraI Eco (SEQ ID NO: 22), XPD Mbu (SEQ ID NO: 23) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736.

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises (a) E94C and A360C or (b) E94C, A360C, C109A and C136A and then optionally (ΔM1)G1G2 (i.e. deletion of M1 and then addition G1 and G2).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

Helicase(s) and Molecular Brake(s)

In a preferred embodiment, the method comprises:

(i) providing the/each polynucleotide with one or more helicases and one or more molecular brakes attached to the/each polynucleotide;

(b) contacting the/each polynucleotide with a transmembrane pore and applying a potential across the pore such that the one or more helicases and the one or more molecular brakes are brought together and both control the movement of at least one strand of the/each polynucleotide through the pore;

(c) taking one or more measurements as the/each polynucleotide moves with respect to the pore wherein the measurements are indicative of one or more characteristics of the polynucleotide and thereby characterising the modified or template polynucleotide.

This type of method is discussed in detail in the International Application PCT/GB2014/052737.

Spacers

The one or more helicases may be stalled at one or more spacers as discussed in International Application No. PCT/GB2014/050175 (published as WO2014/135838). Any configuration of one or more helicases and one or more spacers disclosed in the International Application may be used in this invention.

When a part of the polynucleotide enters the pore and moves through the pore along the field resulting from the applied potential, the one or more helicases are moved past the spacer by the pore as the polynucleotide moves through the pore. This is because the polynucleotide (including the one or more spacers) moves through the pore and the one or more helicases remain on top of the pore.

The one or more spacers are preferably part of the polynucleotide, for instance they interrupt(s) the polynucleotide sequence. The one or more spacers are preferably not part of one or more blocking molecules, such as speed bumps, hybridised to the polynucleotide.

There may be any number of spacers in the polynucleotide, such as 1, 2, 3, 4, 5, 6, 7, 8, 9, 10 or more spacers. There are preferably two, four or six spacers in the polynucleotide. The one or more spacers are preferably in the Y adaptor or leader sequence. There may be one or more spacers in different regions of the polynucleotide, such as one or more spacers in the Y adaptor and/or hairpin loop adaptor.

The one or more spacers each provides an energy barrier which the one or more helicases cannot overcome even in the active mode. The one or more spacers may stall the one or more helicases by reducing the traction of the helicase (for instance by removing the bases from the nucleotides in the polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the polynucleotide. It is straightforward to determine whether or not the one or more helicases are stalled at one or more spacers in the absence of a transmembrane pore and an applied potential. For instance, the ability of a helicase to move past a spacer and displace a complementary strand of DNA can be measured by PAGE.

The one or more spacers typically comprise a linear molecule, such as a polymer. The one or more spacers typically have a different structure from the polynucleotide. For instance, if the polynucleotide is DNA, the one or more spacers are typically not DNA. In particular, if the polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA) or a synthetic polymer with nucleotide side chains. The one or more spacers may comprise one or more nucleotides in the opposite direction from the polynucleotide. For instance, the one or more spacers may comprise one or more nucleotides in the 3' to 5' direction when the polynucleotide is in the 5' to 3' direction. The nucleotides may be any of those discussed above.

The one or more helicases may be stalled by (i.e. before) or on each linear molecule spacers. If linear molecule spacers are used, the polynucleotide is preferably provided with a double stranded region of polynucleotide adjacent to the end of each spacer past which the one or more helicases are to be moved. If linear molecule spacers are used, the polynucleotide is preferably provided with a blocking molecule at the end of each spacer opposite to the end past which the one or more helicases are to be moved. This can help to ensure that the one or more helicases remain stalled on each spacer. It may also help retain the one or more helicases on the polynucleotide in the case that it/they diffuse(s) off in solution. The blocking molecule may be any of the chemical groups discussed below which physically cause the one or more helicases to stall. The blocking molecule may be a double stranded region of polynucleotide. The blocking molecule may be BNA.

The method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths may be increased 1.5 fold, 2 fold, 2.5 fold or 3 fold.

Membrane

The pore used in the invention may be present in a membrane. In the method of the invention, the polynucleotide is typically contacted with the pore in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is preferably a triblock copolymer membrane.

The membrane is most preferably one of the membranes disclosed in International Application No. PCT/GB2013/052766 or PCT/GB2013/052767.

The amphiphilic molecules may be chemically-modified or functionalised to facilitate coupling of the polynucleotide.

Coupling

The/each modified polynucleotide is preferably coupled to the membrane comprising the pore. The method may comprise coupling the/each polynucleotide to the membrane comprising the pore. The polynucleotide is preferably coupled to the membrane using one or more anchors. The polynucleotide may be coupled to the membrane using any known method.

Each anchor comprises a group which couples (or binds) to the polynucleotide and a group which couples (or binds) to the membrane. Each anchor may covalently couple (or bind) to the polynucleotide and/or the membrane. The polynucleotide is preferably coupled to the membrane using the Y adaptor or leader sequence and/or the hairpin loop.

The polynucleotide may be coupled to the membrane using any number of anchors, such as 2, 3, 4 or more anchors. For instance, a polynucleotide may be coupled to the membrane using two anchors each of which separately couples (or binds) to both the polynucleotide and membrane.

The one or more anchors may comprise the one or more helicases and/or the one or more molecular brakes.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalized, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used to couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The use of a linker is preferred in the sequencing embodiments discussed below. If a polynucleotide is permanently coupled directly to the membrane in the sense that it does not uncouple when interacting with the pore (i.e. does not uncouple in step (b) or (e)), then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

Suitable methods of coupling are disclosed in International Application No. PCT/GB12/05119 1 (published as WO 2012/164270) and UK Application No. 1406155.0.

Uncoupling

The method of the invention may involve characterising multiple modified double stranded polynucleotides and uncoupling of the at least the first modified double stranded polynucleotide.

In a preferred embodiment, the invention involves characterising two or more modified double stranded polynucleotides. The method comprises:

(a) providing a first modified double stranded polynucleotide in a first sample;
(b) providing a second modified double stranded polynucleotide in a second sample;
(c) coupling the first polynucleotide in the first sample to a membrane using one or more anchors;
(d) contacting the first polynucleotide with a transmembrane pore such that at least one strand of the first polynucleotide moves through the pore;
(e) taking one or more measurements as the first polynucleotide moves with respect to the pore wherein the measurements are indicative of one or more characteristics of the first polynucleotide and thereby characterising the first polynucleotide;
(f) uncoupling the first polynucleotide from the membrane;
(g) coupling the second polynucleotide in the second sample to the membrane using one or more anchors;
(h) contacting the second polynucleotide with the pore such that at least one strand of the second polynucleotide moves through the pore; and
(i) taking one or more measurements as the second polynucleotide moves with respect to the pore wherein the measurements are indicative of one or more characteristics of the second polynucleotide and thereby characterising the second polynucleotide.

This type of method is discussed in detail in the UK Application No. 1406155.0.

Other Characterisation Method

In another embodiment, the/each modified double stranded polynucleotide is characterised by detecting labelled species that are released as a polymerase incorporates nucleotides into the polynucleotide. The polymerase uses the polynucleotide as a template. Each labelled species is specific for each nucleotide. The/each polynucleotide is contacted with a transmembrane pore, a polymerase and labelled nucleotides such that phosphate labelled species are sequentially released when nucleotides are added to the polynucleotide(s) by the polymerase, wherein the phosphate species contain a label specific for each nucleotide. The polymerase may be any of those discussed above. The phosphate labelled species are detected using the pore and thereby characterising the polynucleotide. This type of method is disclosed in European Application No. 13187149.3 (published as EP 2682460). Any of the embodiments discussed above equally apply to this method.

Kits

The present invention also provides a kit for modifying a template polynucleotide. The kit comprises (a) a population of MuA substrates of the invention and (b) a MuA transposase and (c) a polymerase. Any of the embodiments discussed above with reference to the methods and products of the invention equally apply to the kits.

The kit may further comprise the components of a membrane, such as the components of an amphiphilic layer or a lipid bilayer. The kit may further comprise a transmembrane pore or the components of a transmembrane pore. The kit may further comprise a polynucleotide binding protein. Suitable membranes, pores and polynucleotide binding proteins are discussed above.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention.

Example 1

This example describes a method for modifying a template double stranded polynucleotide, especially for characterisation using nanopore sequencing. This example shows that MuA transposase was able to insert MuA substrates which contained a hairpin loop. The gaps in the construct were then filled using a polymerase and the double-stranded construct was then heated in order to melt the double-stranded DNA. This resulted in single-stranded DNA which had a hairpin from which a polymerase produced a complement. This construct was then ligated to an adaptor with a pre-bound enzyme and finally hybridised to a tether. This DNA construct then exhibited helicase controlled DNA movement through a nanopore.

Figure 2:
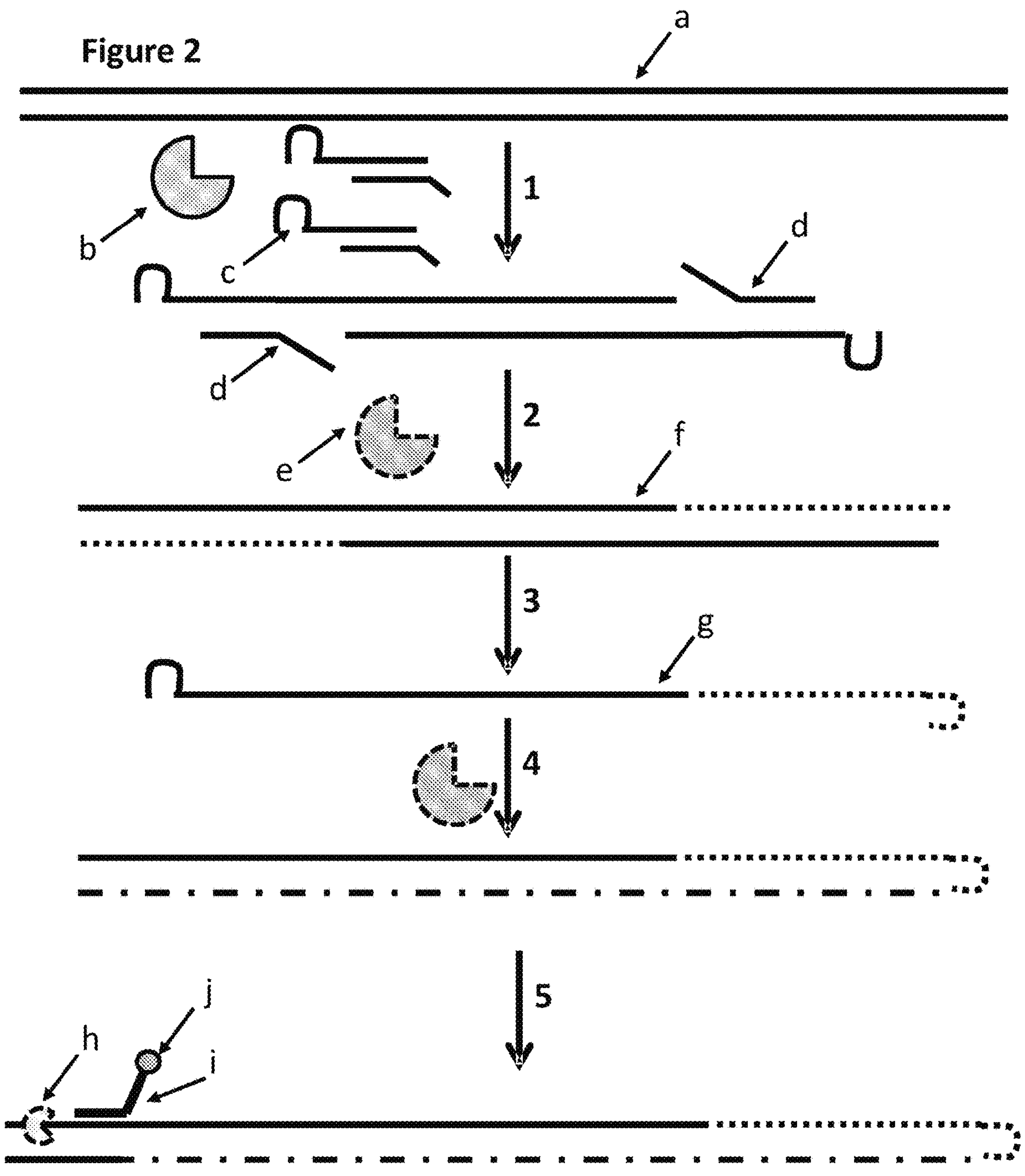
FIG. 2 shows a cartoon representation of the method of modifying a template double-stranded polynucleotide (labelled a) outlined in Example 1. Step 1 involved contacting a template double-stranded polynucleotide with a MuA transposase (labelled b) and a population of double-stranded MuA substrates (labelled c, the double stranded MuA substrates each contained a 5' hairpin loop) so that the MuA transposase fragmented the template double-stranded polynucleotide and inserted the MuA substrates at each side of the point of fragmentation. Step 2 involved treating the template strand with a polymerase (labelled e) and dNTPs which displaced the DNA fragments labelled d and produced complementary strands to the DNA 5' hairpin loop. Step 3 involved heat treatment of the double-stranded DNA construct labelled f so that the strands were denatured into single-stranded DNA (labelled g). Step 4 involved a second treatment with a DNA polymerase which formed the complementary strand. Finally, step 5 involved dA-tailing of the double-stranded DNA construct produced in step 4, ligation of an adapter which had an enzyme (labelled h) pre-bound and hybridisation of a DNA strand (labelled i) which contained a cholesterol tether (labelled j). This produced the final DNA construct which was tested in the nanopore system described in Example 1.

Materials and Methods 1.1—Fragmentation of the DNA Template Using the MuA Transposase The MuA adapter X that was used in this example had a 5' 21 bp hairpin (adapter labelled c in FIG. 2, upper strand=SEQ ID NO: 29, lower strand=SEQ ID NO: 30 attached at its 5' end to the 3' end of the sequence GATCU). The upper and lower strands of the adapter were annealed at 10 uM, from 95° C. at 2° C. min-1, in 10 mM Tris pH 7.5, 50 mM NaCl.

The MuA fragmentation reactions (10 μL) were set up as described in Table 1 below and incubated for 1 hour at 30° C. The MuA enzyme was then heat inactivated by heating at 75° C. for 15 minutes. Finally, the resultant DNA was 1.5×SPRI purified and eluted in nuclease free water (42 μL, Sample 1).

TABLE 1

| Reagent | Components |
|---|---|
| Lambda DNA (SEQ ID NO: 31) | 50 ng $\mu L^{-1}$ |
| MuA adapter X | 200 nM |
| MuA (Thermo) | 50 nM |
| Buffer | 25 mM Tris-HCl pH 8.0, 10 mM MgCl2, 110 mM NaCl, 0.05% Triton X-100, 10% glycerol |

1.2—Incubation of the DNA Template with DNA Polymerase

Following the MuA fragmentation procedure, the purified DNA was then incubated with a DNA polymerase in order to copy the upper strand hairpin.

The DNA polymerase reactions (50 uL) were set up as described in Table 2 below and incubated at 68° C. for 10 minutes. Finally, the resultant DNA was 1.5×SPRI purified and eluted in nuclease free water (42 μL, Sample 2).

TABLE 2

| Reagent | Components |
|---|---|
| Sample 1 | 39 μl |
| 10x ThermoPol Buffer | 5 μl of 200 mM Tris-HCl pH 8.8, 100 mM $(NH_4)_2SO_4$, 100 mM KCl, 20 mM $MgSO_4$, 1.0% Triton ® X-100 |
| 9°N Polymerase (NEB) | 5 μL |
| dNTPs | 1 μL of 10 mM (Final concentration 0.2 mM) |

1.3—Heat Denaturation and Polymerase Fill-in

Following the hairpin copying stage sample 2 was then treated to a single denaturation step and polymerase fill-in. For the polymerase fill-in reaction the polymerase was provided with dCTP/dGTP/dATP but the standard dTTP was replaced with a different nucleotide species 5-propynyl-dU. The reactions (50μ) were set up as described in Table 3 below and incubated for 2 minutes at 95° C., 30 seconds at 55° C. and 30 minutes at 68° C. Finally, the resultant DNA was 1.5×SPRI purified and eluted in nuclease free water (45 μL, Sample 3).

TABLE 3

| Reagent | Components |
|---|---|
| Sample 2 | 39 μl |
| 10x ThermoPol Buffer | 5 μl of 200 mM Tris-HCl pH 8.8, 100 mM $(NH_4)_2SO_4$, 100 mM KCl, 20 mM $MgSO_4$, 1.0% Triton ® X-100 |
| 9°N Polymerase (NEB) | 5 μL |
| dNTPs-(5-propynyl-dU/dCTP/dGTP/dATP) | 1 μL of 10 mM (Final concentration 0.2 mM) |

1.4—dA Tailing Reaction

Sample 3 was then dA-tailed as described in Table 4 below and incubated for 30 minutes at 37° C. The resultant DNA was 1.5×SPRI purified and eluted in nuclease free water (20 μL, Sample 4).

TABLE 4

| Reagent | Components |
|---|---|
| Sample 3 | 42 μl |
| 10x NEB dA-tailing buffer | 5 μl |
| Klenow $exo^-$ | 3 μL |

1.5—Ligation of Adapter with Pre-Loaded Enzyme

Sample 4 was then ligated to Y-adapter 1 (upper strand=20 iSpC3 spacers attached at the 3' end to SEQ ID NO: 32 which was attached at the 3' end to four iSp18 spacers which were attached at the 3' end to SEQ ID NO: 33, bottom strand=SEQ ID NO: 34 which had a 5' phosphate attached) with pre-loaded enzyme (T4 Dda—E94C/A360C/C109A/C136A (SEQ ID NO: 24 with mutations E94C/A360C/C114A/C171A/C421D and then (ΔM1)G1G2)) as described in Table 5 below and incubated for 20 minutes at room temperature. The resultant DNA was 0.4×SPRI purified and washed with buffer (200 μL of 750 mM NaCl, 10% PEG 8000, 50 mM Tris.HCl pH8) and eluted in buffer (20 μL of 40 mM CAPS pH 10, 40 mM KCl Sample 5).

TABLE 5

| Reagent | Components |
|---|---|
| Sample 4 | 20 μl |
| Y-adapter 1 | 5 μl |
| NEB Blunt TA MM (2x) | 25 μL |

1.6—Annealing of Tether

The DNA analytes present in Sample 5 were then annealed to a tether. Sample 5 was incubated with the DNA tether (the sequence AACAACCT was attached at its 5' end to three iSp18 spacers, two thymines and a 5' cholesterol TEG and the sequence AACAACCT was attached at its 3' end to three iSp18 spacers which are attached at the 3' end to SEQ ID NO: 35), 500 nM, 5 μL) for 10 minutes at room temperature. The resultant sample was known as Sample 6.

1.7—Electrophysiology Testing

Prior to setting up the experiment, DNA sample 6 (a quarter of the total volume of sample 6) was added to buffer (25 mM Potassium Phosphate buffer (pH 7.5), 500 mM KCl), MgCl2 (1 mM) and ATP (2 mM) which gave a total volume of 150 μL.

Electrical measurements were acquired from single MspA nanopores inserted in block copolymer in buffer (25 mM K Phosphate buffer, 150 mM Potassium Ferrocyanide (II), and 150 mM Potassium Ferricyanide (III), pH 8.0). After achieving a single pore inserted in the block copolymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. The enzyme (T4 Dda—E94C/C109A/C136A/A360C, 10 nM final concentration), DNA sample 6 and fuel (MgCl2 2 mM final concentration, ATP 2 mM final concentration) pre-mix (150 μL total) was then flowed into the single nanopore experimental system. The experiment was run at 120 mV and helicase-controlled DNA movement monitored for 6 hours.

Results

Figure 3:
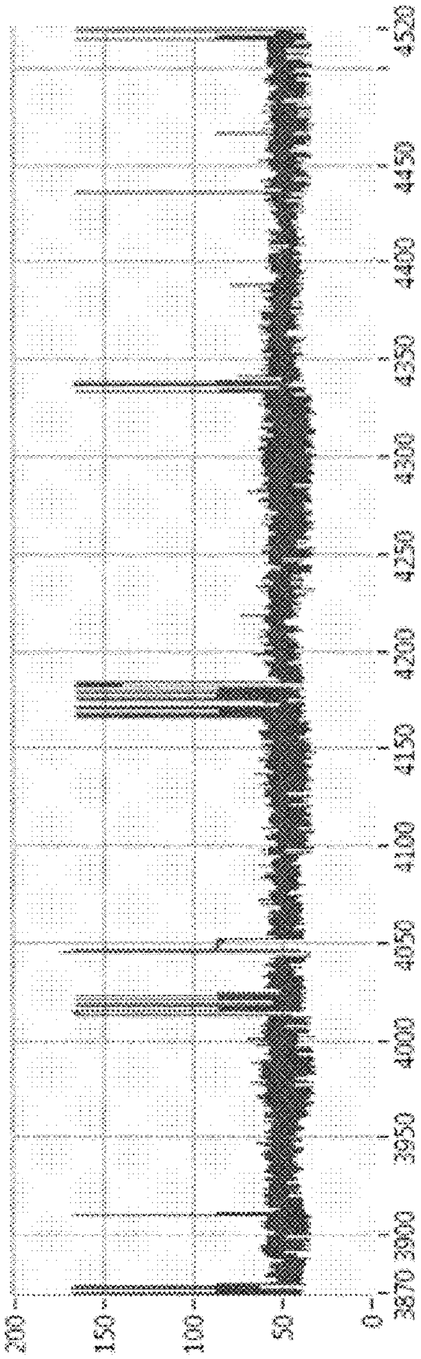
FIG. 3 shows an example current trace (y-axis label=Current (pA), x-axis label=Time (s)) of when a helicase (T4 Dda—E94C/C109A/C136A/A360C (SEQ ID NO: 24 with mutations E94C/C109A/C136A/A360C)) controlled the translocation of DNA sample 6 through an MspA nanopore.

Helicase controlled DNA movement of the DNA produced at the end of the sample preparation procedure (sample 6) was observed. FIG. 3 shows an example of a helicase controlled DNA movement.

Figure 4:
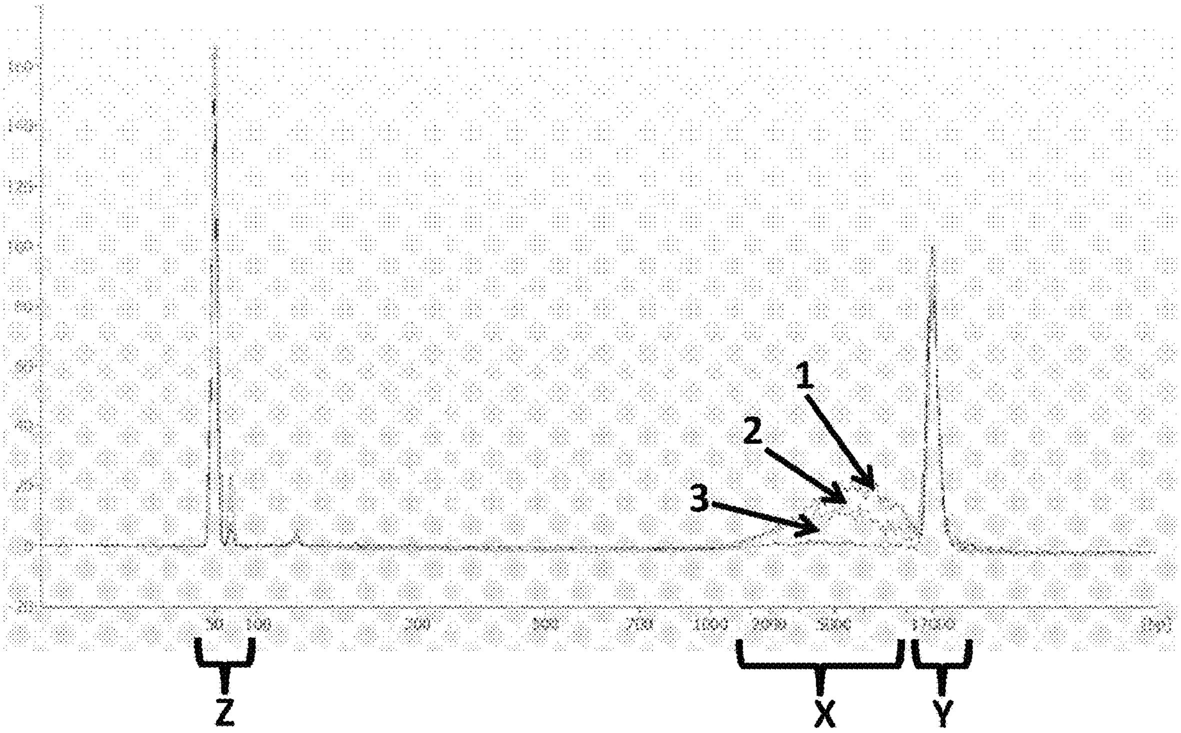
FIG. 4 shows an Agilent 12,000 DNA chip trace. The line labelled 1 was the untreated MuA fragmented DNA input material, the line labelled 2 was the analyte that had the 68° C. incubation step (in 1.2 of Example 1) and subsequently had undergone all of step 1.3 of Example 1 and the line labelled 3 did not have the 68° C. incubation in step 1.2 of Example 1 but had undergone all of step 1.3 of Example 1. Region X corresponded to the double-stranded DNA library, region Y corresponded to the upper marker of the Agilent 12,000 and region Z corresponded to the lower marker of the Agilent 12,000 chip.

The sample preparation procedure was also analysed using an Agilent 12,000 DNA chip trace. If there was no pre-incubation at 68° C., prior to step 1.2 (where the 5' hairpin was transcribed), then following strand dissociation (heat denaturation step 1.3) no synthetic complement was made (shown as a dash/dotted line after step 4 of FIG. 2), as the strands lacked the necessary 3' hairpin from which the polymerase was initiated. This was observed in the Agilent 12,000 DNA chip trace shown in FIG. 4, where the line labelled 1 was the untreated MuA fragmented DNA input material, the line labelled 2 was the analyte that had the 68° C. incubation step (in 1.2 above) and subsequently had undergone all of step 1.3 and the line labelled 3 did not have the 68° C. incubation in step 1.2 but had undergone all of step 1.3. As such, for line 3 no dsDNA was made and, therefore, a flat line (region labelled X) was observed on the Agilent trace as there was no hairpin copied before strand dissociation at 95° C. However, for line 2 the hairpin was transcribed and as such on strand dissociation the polymerase initiated fill-in from the new 3' hairpin. This meant that line 2 shown a peak in region X which corresponded to the dsDNA product that was made from the copied hairpin.

Figure 6:
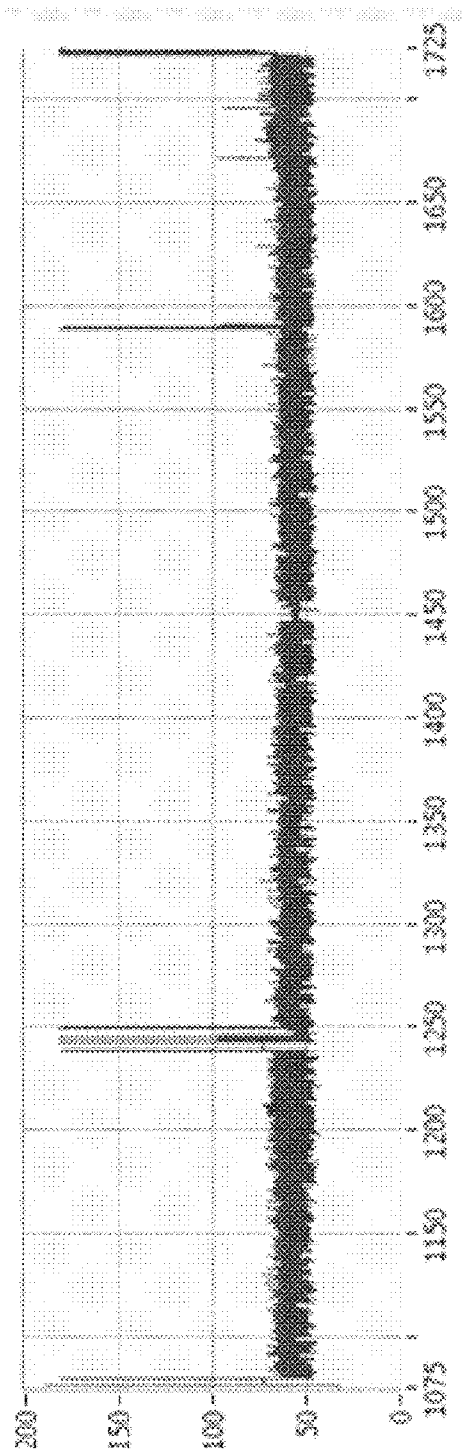
FIG. 6 shows an example current trace (y-axis label=Current (pA), x-axis label=Time (s)) of when a helicase (T4 Dda—E94C/C109A/C136A/A360C) controlled the translocation of DNA sample 7 through an MspA nanopore.

The above procedure was repeated as described above however in step 1.3 the polymerase was provided with the standard DNA dNTP's—dCTP/dATP/dGTP/dTTP rather than 5-propynyl-dU, which produced DNA Sample 7. FIG. 6 shows example helicase-controlled DNA movement for DNA Sample 7 (which was produced using standard DNA dNTP's in step 1.3). The sample preparation procedure was successful and helicase controlled DNA movements were observed for this sample.

Example 2

Figure 7:
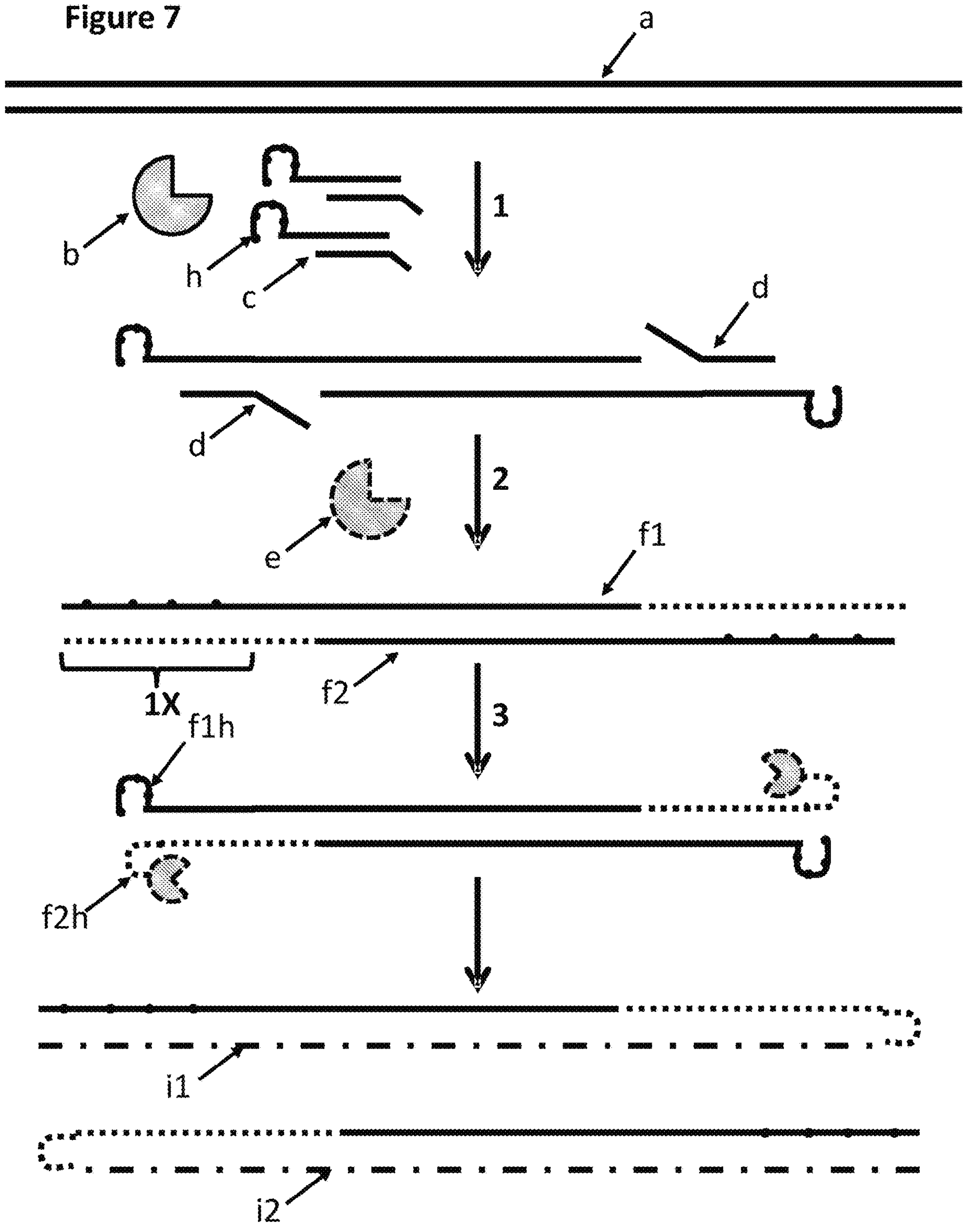
FIG. 7 shows a cartoon representation of a method of modifying a template double stranded polynucleotide (labelled a). Step 1 involved contacting a template double-stranded polynucleotide with a MuA transposase (labelled b) and a population of double-stranded MuA substrates (labelled C, where the double stranded MuA substrates each contained a 5' hairpin loop which contained I/Z's in the hairpin (labelled h and shown as black circles) which replaced the G/C's) so that the MuA transposase fragmented the template double-stranded polynucleotide and inserted the MuA substrates at each side of the point of fragmentation. Step 2 involved treating the template strand with a polymerase (labelled e) and dNTPs which displaced the DNA fragments labelled d and produced complementary strands to the DNA 5' hairpin loop (dsDNA produced was labelled f). The double stranded region (labelled 1X) formed by the polymerase is made up of two strands which are both capable of forming a hairpin loop. The hairpin loop formed by strand F2 has a higher Tm than the Tm of the double stranded region 1X, this is because strand F2's hairpin loop is made up of C/T/A/G and the double stranded region 1X is strand f2 hybridised to strand f1 where strand F1 is made up of Z/T/A/I (and Z and I only form two hydrogen bonds whereas C/G form 3 hydrogen bonds). Therefore, F2 forms a hairpin loop (labelled f2h) and F1 forms a hairpin loop (labelled f1h), the hairpin loop formed by strand F1 has a higher Tm than the hairpin loop formed by strand F2. The DNA polymerase was then able to produce complementary strands shown as a dash/dotted line (the entire dsDNA construct labelled i1 and i2). Therefore, the polymerase was able to form a complementary strand (shown as a dashed/dotted line) without needing to heat the dsDNA produced in step 2 (and labelled f1 hybridised to f2).

This example describes a method for modifying a template double stranded polynucleotide, especially for characterisation using nanopore sequencing. FIG. 7 shows a cartoon representation of the sample preparation steps described in steps 2.1 and 2.2 below. This example shows that MuA transposase was able to insert MuA substrates which contained a hairpin loop which contained analogues of dG and dC in the hairpin loop of the MuA adapter (dG was replaced with deoxyinosine and dC was replaced deoxyzebularine). The gaps in the construct were then filled using a polymerase which replaced the overhang strands with new strands which complemented the strands comprising the hairpin loops. The new strand, which complemented the strand comprising the hairpin loop, was also capable of forming a hairpin loop. The hairpin loop of the new strand had a higher Tm than the double stranded region formed between the complementary strand and the hairpin loop which was made of A/T/Z/I (labelled 1X in FIG. 7). Therefore, the hairpin in the new strand formed (labelled f2h in FIG. 7) and the hairpin loop made of A/T/Z/I also formed (labelled f1h in FIG. 7). The polymerase then used the hairpin loop as a primer to make the complementary strands. Therefore, there was no need for an additional heating step to separate the dsDNA construct produced after step 2 of FIG. 7.

2.1—Fragmentation of the DNA Template Using the MuA Transposase

The MuA adapter used in this example had a 5' 7 bp hairpin with dG replaced for dInosine and dC replaced for dZebularine. The upper strands (the modified polynucleotide sequence IZITAZ (where I is an deoxyinosine and Z is deoxyzebularine) is attached to the 5' end of non-modified polynucleotide sequence TTTTTA which is attached at the 3' end to the modified polynucleotide sequence ITAZIZ (where I is an deoxyinosine and Z is deoxyzebularine) which is attached to the 5' end of SEQ ID NO: 39) and lower strands (SEQ ID NO: 38) of the adapter P were annealed at 10 uM, from 95° C. at 2° C. min-1, in 10 mM Tris pH 7.5, 50 mM NaCl.

The MuA fragmentation reactions (10 μL) were set up as described in Table 1 above using adapter P instead of adapter X and incubated for 1 hour at 30° C. The MuA enzyme was then heat inactivated by heating at 75° C. for 15 minutes. Finally, the resultant DNA was 1.5×SPRI purified and eluted in nuclease free water (42 μL).

2.2—Incubation of the DNA Template with DNA Polymerase

Following the MuA fragmentation procedure, the purified DNA was then incubated with a DNA polymerase in order to copy the upper strand hairpin (which had G/C replaced with I/Z).

It was during this step that the new strand, which complemented the strand comprising the hairpin loop, formed a hairpin loop. This was owing to the fact that the hairpin loop formed by the new strand had a higher Tm than the double-stranded region formed between the complementary strand and the hairpin loop which contained analogues of dZ and dI. Therefore, there was no need to heat the double-stranded DNA, to separate it into ssDNA, as the hairpin loop with the higher Tm was formed preferentially and the polymerase then used this hairpin loop as a primer to make the complementary strand.

The DNA polymerase reaction (50 uL) was set up as described in the Table below and incubated at 37° C. for 30 minutes. Finally, the resultant DNA was 1.5×SPRI purified and eluted in nuclease free water (42 μL).

TABLE 6

| Reagent | Components |
|---|---|
| Sample 1 | 39 μl |
| 10x NEBuffer | 5 μl of 100 mM Tris-HCl (pH 7.9), 500 mM $NaCl_2$, 100 mM $MgCl_2$, 10 mM DTT |
| Klenow Fragment (NEB) | 2.5 μL |
| SSB (Promega) | 2.5 μL |
| dNTPs | 1 μL of 10 mM (Final concentration 0.2 mM) |

This strand could be further modified by dA tailing, ligating an adapter with an enzyme pre-loaded and hybridising a tether (as described in Example 1.4-1.6) in order to produce a strand which could be characterised using a nanopore system (as described in Example 1.7).

The invention claimed is:

1. A method for modifying a template double stranded polynucleotide, comprising:
   (a) contacting the template polynucleotide with a MuA transposase and a population of double stranded MuA substrates each comprising (i) at least one overhang and (ii) at least one hairpin loop in the opposite strand from the strand comprising the at least one overhang such that the transposase fragments the template polynucleotide and ligates a substrate to one or both ends of the double stranded fragments and thereby produces a plurality of fragment/substrate constructs;
   (b) contacting the fragment/substrate constructs with a polymerase such that the polymerase displaces the strands comprising the overhangs and replaces them with strands which complement the strands comprising the hairpin loops and thereby produces a plurality of double stranded constructs each comprising a double stranded fragment of the template polynucleotide; and
   (c) separating the two strands of the double stranded constructs and using the strands as templates to form a plurality of modified double stranded polynucleotides each comprising two complementary strands linked by at least one hairpin loop.

2. A method according to claim 1, wherein step (c) comprises separating the two strands of the double stranded constructs by increasing one or more of pH, temperature and ionic strength.

3. A method according to claim 1, wherein step (c) comprises contacting the separated strands with a polymerase such that the polymerase uses the strands as templates to form the plurality of modified double stranded polynucleotides.

4. A method according to claim 1, wherein step (c) comprises (i) contacting the plurality of separated strands with a population of nucleotide oligomers which comprises every possible combination of nucleotides which are complementary to all of the nucleotides in the strands under conditions in which the oligomers are capable of hybridising to the strands and (ii) ligating together those oligomers that hybridise to the strands to form the plurality of modified double stranded polynucleotides.

5. A method according to claim 1, wherein step (c) comprises contacting the plurality of double stranded constructs with a polymerase such that the polymerase simultaneously separates the two strands of the double stranded constructs and uses the strands as templates to form the plurality of modified double stranded polynucleotides.

6. A method according to claim 1, wherein the at least one hairpin loop does not link the two strands of each substrate.

7. A method according to claim 1, wherein the at least one overhang is 4, 5 or 6 nucleotides in length.

8. A method according to claim 1, wherein each substrate comprises a selectable binding moiety.

9. A method according to claim 1, wherein each substrate comprises a leader sequence which is capable of threading through a transmembrane pore.

10. A method according to claim 1, wherein the method further comprises (d) attaching Y adaptors to the plurality of modified double stranded polynucleotides at the opposite ends from the hairpin loops and wherein the Y adaptors optionally comprise a leader sequence which is capable of threading through a transmembrane pore.

11. A method according to claim 1, wherein the method further comprises binding one or more polynucleotide binding proteins to the plurality of modified double stranded polynucleotides.

12. A method of characterising at least one polynucleotide modified using a method according to claim 1, comprising:
   a) contacting the modified polynucleotide with a transmembrane pore such that at least one strand of the polynucleotide moves through the pore; and
   b) taking one or more measurements as the at least one strand moves with respect to the pore wherein the measurements are indicative of one or more characteristics of the at least one strand and thereby characterising the modified polynucleotide.

13. A method of characterising a template polynucleotide, comprising:
   a) modifying the template polynucleotide using a method according to claim 1 to produce a plurality of modified polynucleotides;
   b) contacting each modified polynucleotide with a transmembrane pore such that at least one strand of each polynucleotide moves through the pore; and
   c) taking one or more measurements as each polynucleotide moves with respect to the pore wherein the measurements are indicative of one or more characteristics of each polynucleotide and thereby characterising the template polynucleotide.

14. A method according to claim 12, wherein both strands of the/each modified polynucleotide move through the pore.

15. A method according to claim 12, wherein the one or more characteristics are selected from (i) the length of the polynucleotide, (ii) the identity of the polynucleotide, (iii) the sequence of the polynucleotide, (iv) the secondary structure of the polynucleotide and (v) whether or not the polynucleotide is modified.

16. A method according to claim 12, wherein contacting step (a) or contacting step (b) further comprises contacting the/each modified polynucleotide with a polynucleotide binding protein such that the protein controls the movement of the/each polynucleotide through the pore.

17. A method according to claim 16, wherein the method comprises
   (i) contacting the/each modified polynucleotide with a transmembrane pore and one or more polynucleotide binding proteins such that at least one strand of the/each polynucleotide moves through the pore and the one or more proteins control the movement of the/each polynucleotide through the pore; and (ii) measuring the current passing through the pore as the/each polynucleotide moves with respect to the pore wherein the current is indicative of one or more characteristics of the/each polynucleotide and thereby characterising the polynucleotide.

18. A method according to claim 17, wherein the one or more polynucleotide binding proteins are bound to the/each modified polynucleotide before it is/they are contacted with the transmembrane pore.

19. A method according to claim 17, wherein the one or more polynucleotide binding proteins are one or more helicases.

* * * * *